United States Patent
Uber, III et al.

(10) Patent No.: US 11,141,535 B2
(45) Date of Patent: Oct. 12, 2021

(54) FLUID PATH IMPEDANCE ASSESSMENT FOR IMPROVING FLUID DELIVERY PERFORMANCE

(71) Applicant: BAYER HEALTHCARE LLC, Whippany, NJ (US)

(72) Inventors: Arthur Uber, III, Pittsburgh, PA (US); Chelsea Marsh, Pittsburgh, PA (US); William Barone, Pittsburgh, PA (US); Michael McDermott, Pittsburgh, PA (US); Timothy Newing, Thornleigh (AU); Michael Spohn, Fenelton, PA (US); Vince Delbrugge, Indiana, PA (US); Ralph Schriver, Tarentum, PA (US); Kevin Cowan, Allison Park, PA (US); Barry Tucker, Verona, PA (US); Ronald Heller, Monroeville, PA (US); David Griffiths, Pittsburgh, PA (US); Matthew Schrauder, Mars, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 16/621,822

(22) PCT Filed: Aug. 28, 2018

(86) PCT No.: PCT/US2018/048338
§ 371 (c)(1),
(2) Date: Dec. 12, 2019

(87) PCT Pub. No.: WO2019/046299
PCT Pub. Date: Mar. 7, 2019

(65) Prior Publication Data
US 2020/0121860 A1 Apr. 23, 2020

Related U.S. Application Data

(60) Provisional application No. 62/552,447, filed on Aug. 31, 2017, provisional application No. 62/552,570,
(Continued)

(51) Int. Cl.
A61M 5/315 (2006.01)
G16H 20/17 (2018.01)
A61M 5/32 (2006.01)

(52) U.S. Cl.
CPC .... *A61M 5/31535* (2013.01); *A61M 5/31596* (2013.01); *A61M 5/3221* (2013.01);
(Continued)

(58) Field of Classification Search
CPC .......... A61M 5/31535; A61M 5/31596; A61M 5/3221; A61M 5/16827; A61M 5/16831;
(Continued)

(56) References Cited

U.S. PATENT DOCUMENTS 383,858 A 6/1888 Campbell
508,584 A 11/1893 Stevens
(Continued)

FOREIGN PATENT DOCUMENTS

CA 2045070 A1 2/1992
CA 2077712 A1 12/1993
(Continued)

OTHER PUBLICATIONS

Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).
(Continued)

*Primary Examiner* — Laura A Bouchelle
*Assistant Examiner* — Anh Bui
(74) *Attorney, Agent, or Firm* — David Schramm; Joseph L. Kent; James R. Stevenson

(57) ABSTRACT

A fluid injector system for delivering a multi-phase fluid injection to a patient and methods of fluid delivery is disclosed. Methods of creating and using a multi-aspect fluid path impedance model of the injector system are used. Modeling and adjustment of factors that affect impedance and prevent or reduce backflow, reduce the likelihood of fluid flow rate spikes and provide more accurate flow rates and mixing ratios of fluids may be repeated or happen essentially continuously during an injection. The adjust-
(Continued)

ments may be determined before the injection or determined and/or adjusted during the injection. The determination may include sensor feedback commonly used in injectors such as pressure and position feedback as well as other sensors. In all cases, the user can be notified of adjustments through on-screen notices and/or through the recordation of the injection data by a control device of the injector at the conclusion of the injection.

18 Claims, 43 Drawing Sheets

Related U.S. Application Data filed on Aug. 31, 2017, provisional application No. 62/552,631, filed on Aug. 31, 2017.

(52) U.S. Cl.
CPC ..... *G16H 20/17* (2018.01); *A61M 2205/3334* (2013.01); *A61M 2205/3341* (2013.01); *A61M 2205/3396* (2013.01)

(58) Field of Classification Search
CPC ...... A61M 5/16886; A61M 2205/3334; A61M 2205/3341; A61M 2205/3396; G16H 20/17
See application file for complete search history.

(56) References Cited

U.S. PATENT DOCUMENTS

| | | |
|---|---|---|
| 945,143 A | 1/1910 | Iacques |
| 2,511,291 A | 6/1950 | Mueller |
| 2,583,206 A | 1/1952 | Borck et al. |
| 3,156,236 A | 11/1964 | Williamson |
| 3,159,312 A | 12/1964 | Van Sciver |
| 3,276,472 A | 10/1966 | Jinkens et al. |
| 3,349,713 A | 10/1967 | Fassbender |
| 3,520,295 A | 7/1970 | Paul |
| 3,523,523 A | 8/1970 | Heinrich et al. |
| 3,623,474 A | 11/1971 | Heilman et al. |
| 3,635,444 A | 1/1972 | Charles |
| 3,671,208 A | 6/1972 | Wayne |
| 3,701,345 A | 10/1972 | Heilman |
| 3,719,207 A | 3/1973 | Takeda |
| 3,755,655 A | 8/1973 | Senecal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Lyons et al. |
| 3,868,967 A | 3/1975 | Harding |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | Lefevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,204,775 A | 5/1980 | Speer |
| 4,207,871 A | 6/1980 | Jenkins |
| 4,208,136 A | 6/1980 | King et al. |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,329,067 A | 5/1982 | Goudy, Jr. |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,441,823 A | 4/1984 | Power et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers De Beyl et al. |
| 4,552,130 A | 11/1985 | Kinoshita |
| 4,559,036 A | 12/1985 | Wunsch |
| 4,563,175 A | 1/1986 | Lafond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | DiGianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |

(56) References Cited

U.S. PATENT DOCUMENTS

| | | |
|---|---|---|
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,952,068 A | 8/1990 | Flint |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace et al. |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | DiGianfilippo et al. |
| 5,059,171 A | 10/1991 | Bridge et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kampfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |

(56) References Cited

U.S. PATENT DOCUMENTS

| | | | |
|---|---|---|---|
| 5,724,976 | A | 3/1998 | Mine et al. |
| 5,725,500 | A | 3/1998 | Micheler |
| 5,739,508 | A | 4/1998 | Uber, III |
| 5,743,266 | A | 4/1998 | Levene et al. |
| 5,768,405 | A | 6/1998 | Makram-Ebeid |
| 5,796,862 | A | 8/1998 | Pawlicki et al. |
| 5,799,649 | A | 9/1998 | Prince |
| 5,800,397 | A | 9/1998 | Wilson et al. |
| 5,806,519 | A | 9/1998 | Evans, III et al. |
| 5,808,203 | A | 9/1998 | Nolan, Jr. et al. |
| 5,827,219 | A | 10/1998 | Uber, III et al. |
| 5,827,504 | A | 10/1998 | Yan et al. |
| 5,840,026 | A | 11/1998 | Uber, III et al. |
| 5,843,037 | A | 12/1998 | Uber, III |
| 5,846,517 | A | 12/1998 | Unger |
| 5,865,744 | A | 2/1999 | Lemelson |
| 5,873,861 | A | 2/1999 | Hitchins et al. |
| 5,881,124 | A | 3/1999 | Giger et al. |
| 5,882,343 | A | 3/1999 | Wilson et al. |
| 5,902,054 | A | 5/1999 | Coudray |
| 5,903,454 | A | 5/1999 | Hoffberg et al. |
| 5,916,165 | A | 6/1999 | Duchon et al. |
| 5,920,054 | A | 7/1999 | Uber, III |
| 5,947,935 | A | 9/1999 | Kazousky et al. |
| 5,987,347 | A | 11/1999 | Khoury et al. |
| 5,988,587 | A | 11/1999 | Duchon et al. |
| 6,046,225 | A | 4/2000 | Maddock |
| 6,055,985 | A | 5/2000 | Bae et al. |
| 6,056,902 | A | 5/2000 | Hettinga |
| 6,063,052 | A | 5/2000 | Uber, III et al. |
| 6,073,042 | A | 6/2000 | Simonetti |
| 6,099,502 | A | 8/2000 | Duchon et al. |
| 6,132,396 | A | 10/2000 | Antanavich et al. |
| 6,149,627 | A | 11/2000 | Uber, III |
| 6,186,146 | B1 | 2/2001 | Glickman |
| 6,201,889 | B1 | 3/2001 | Vannah |
| 6,221,045 | B1 | 4/2001 | Duchon et al. |
| 6,236,706 | B1 | 5/2001 | Hsieh |
| 6,248,093 | B1 | 6/2001 | Moberg |
| 6,306,117 | B1 | 10/2001 | Uber, III |
| 6,313,131 | B1 | 11/2001 | Lawyer |
| 6,317,623 | B1 | 11/2001 | Griffiths et al. |
| 6,322,535 | B1 | 11/2001 | Hitchins et al. |
| 6,344,030 | B1 | 2/2002 | Duchon et al. |
| 6,381,486 | B1 | 4/2002 | Mistretta et al. |
| 6,387,098 | B1 | 5/2002 | Cole et al. |
| 6,397,093 | B1 | 5/2002 | Aldrich |
| 6,397,097 | B1 | 5/2002 | Requardt |
| 6,402,697 | B1 | 6/2002 | Calkins et al. |
| 6,423,719 | B1 | 7/2002 | Lawyer |
| 6,442,418 | B1 | 8/2002 | Evans, III et al. |
| 6,470,889 | B1 | 10/2002 | Bae et al. |
| 6,471,674 | B1 | 10/2002 | Emig et al. |
| 6,478,735 | B1 | 11/2002 | Pope et al. |
| 6,503,226 | B1 | 1/2003 | Martinell et al. |
| 6,520,930 | B2 | 2/2003 | Critchlow et al. |
| 6,527,718 | B1 | 3/2003 | Connor et al. |
| 6,554,819 | B2 | 4/2003 | Reich |
| 6,556,695 | B1 | 4/2003 | Packer et al. |
| 6,572,851 | B2 | 6/2003 | Muramatsu et al. |
| 6,574,496 | B1 | 6/2003 | Golman et al. |
| 6,575,930 | B1 | 6/2003 | Trombley, III et al. |
| 6,597,938 | B2 | 7/2003 | Liu |
| 6,626,862 | B1 | 9/2003 | Duchon et al. |
| 6,635,030 | B1 | 10/2003 | Bae et al. |
| 6,643,537 | B1 | 11/2003 | Zatezalo et al. |
| 6,652,489 | B2 | 11/2003 | Trocki et al. |
| 6,656,157 | B1 | 12/2003 | Duchon et al. |
| 6,673,033 | B1 | 1/2004 | Sciulli et al. |
| 6,685,733 | B1 | 2/2004 | Dae et al. |
| 6,691,047 | B1 | 2/2004 | Fredericks |
| 6,699,219 | B2 | 3/2004 | Emig et al. |
| 6,731,971 | B2 | 5/2004 | Evans et al. |
| 6,754,521 | B2 | 6/2004 | Prince |
| 6,775,764 | B1 | 8/2004 | Batcher |
| 6,776,764 | B2 | 8/2004 | Pinsky |
| 6,866,653 | B2 | 3/2005 | Bae |
| 6,876,720 | B2 | 4/2005 | Tsuyuki |
| 6,879,853 | B2 | 4/2005 | Meaney et al. |
| 6,983,590 | B2 | 1/2006 | Roelle et al. |
| 7,094,216 | B2 | 8/2006 | Trombley, III et al. |
| 7,267,666 | B1 | 9/2007 | Duchon et al. |
| 7,267,667 | B2 | 9/2007 | Houde et al. |
| 7,292,720 | B2 | 11/2007 | Horger et al. |
| 7,351,221 | B2 | 4/2008 | Trombley et al. |
| 7,553,294 | B2 | 6/2009 | Lazzaro et al. |
| 7,553,295 | B2 | 6/2009 | Susi |
| 7,563,249 | B2 | 7/2009 | Schriver et al. |
| 7,666,169 | B2 | 2/2010 | Cowan et al. |
| 7,688,057 | B2 | 3/2010 | Foss et al. |
| 7,861,893 | B2 | 1/2011 | Voegele et al. |
| 7,925,330 | B2 | 4/2011 | Kalafut et al. |
| 8,007,487 | B2 | 8/2011 | Patrick et al. |
| 8,147,464 | B2 | 4/2012 | Spohn et al. |
| 8,162,903 | B2 | 4/2012 | Reilly et al. |
| 8,295,914 | B2 | 10/2012 | Kalafut et al. |
| 8,337,456 | B2 | 12/2012 | Schriver et al. |
| 8,377,003 | B2 | 2/2013 | Wagner |
| 8,403,909 | B2 | 3/2013 | Spohn et al. |
| 8,439,863 | B2 | 5/2013 | Fago et al. |
| 8,486,017 | B2 | 7/2013 | Masuda et al. |
| 8,905,969 | B2 | 12/2014 | Nystrom et al. |
| 8,945,051 | B2 | 2/2015 | Schriver et al. |
| 9,101,708 | B2 | 8/2015 | Small et al. |
| 9,173,995 | B1 | 11/2015 | Tucker et al. |
| 9,199,033 | B1 | 12/2015 | Cowan et al. |
| 9,238,099 | B2 | 1/2016 | Kalafut et al. |
| 9,242,083 | B2 | 1/2016 | Fago et al. |
| 9,259,527 | B2 | 2/2016 | Spohn et al. |
| 9,314,749 | B2 | 4/2016 | Yagi et al. |
| 9,474,857 | B2 | 10/2016 | Riley et al. |
| 9,555,379 | B2 | 1/2017 | Schriver et al. |
| 9,861,752 | B2 | 1/2018 | Buder et al. |
| 9,901,671 | B2 | 2/2018 | Toews et al. |
| 9,987,413 | B2 | 6/2018 | Seibold et al. |
| 10,041,483 | B2 | 8/2018 | Chappel et al. |
| 10,112,008 | B2 | 10/2018 | Neftel et al. |
| 10,201,666 | B2 | 2/2019 | Cowan et al. |
| 10,391,234 | B2 | 8/2019 | Sams et al. |
| 10,549,084 | B2 | 2/2020 | Sokolov et al. |
| 2001/0027265 | A1 | 10/2001 | Prince |
| 2001/0056233 | A1 | 12/2001 | Uber et al. |
| 2002/0007116 | A1 | 1/2002 | Zatezalo et al. |
| 2002/0010551 | A1 | 1/2002 | Wang et al. |
| 2002/0026148 | A1 | 2/2002 | Uber et al. |
| 2002/0099254 | A1 | 7/2002 | Movahed |
| 2002/0123702 | A1 | 9/2002 | Cho |
| 2002/0151854 | A1 | 10/2002 | Duchon et al. |
| 2003/0050556 | A1 | 3/2003 | Uber et al. |
| 2003/0120171 | A1 | 6/2003 | Diamantopoulos et al. |
| 2003/0195462 | A1 | 10/2003 | Mann et al. |
| 2003/0212364 | A1 | 11/2003 | Mann et al. |
| 2003/0216683 | A1 | 11/2003 | Shekalim |
| 2003/0226539 | A1 | 12/2003 | Kim et al. |
| 2004/0011740 | A1 | 1/2004 | Bernard et al. |
| 2004/0025452 | A1 | 2/2004 | McLean |
| 2004/0044302 | A1 | 3/2004 | Bernard et al. |
| 2004/0064041 | A1 | 4/2004 | Lazzaro et al. |
| 2004/0092905 | A1 | 5/2004 | Azzolini |
| 2004/0097806 | A1 | 5/2004 | Hunter et al. |
| 2004/0154788 | A1 | 8/2004 | Symonds |
| 2004/0162484 | A1 | 8/2004 | Nemoto |
| 2004/0163655 | A1 | 8/2004 | Gelfand et al. |
| 2004/0167415 | A1 | 8/2004 | Gelfand et al. |
| 2004/0215144 | A1 | 10/2004 | Duchon et al. |
| 2004/0254533 | A1 | 12/2004 | Schriver et al. |
| 2005/0107697 | A1 | 5/2005 | Berke et al. |
| 2005/0171487 | A1 | 8/2005 | Haury et al. |
| 2005/0234407 | A1 | 10/2005 | Spohn et al. |
| 2005/0234428 | A1 | 10/2005 | Spohn et al. |
| 2006/0052794 | A1 | 3/2006 | McGill et al. |
| 2006/0079765 | A1 | 4/2006 | Neer et al. |
| 2006/0079843 | A1 | 4/2006 | Brooks et al. |
| 2007/0068964 | A1 | 3/2007 | Tanaami et al. |

(56) References Cited

U.S. PATENT DOCUMENTS

| | | |
|---|---|---|
| 2007/0129705 A1 | 6/2007 | Trombley, III et al. |
| 2007/0161970 A1 | 7/2007 | Spohn et al. |
| 2007/0219496 A1* | 9/2007 | Kamen .................. G01F 22/00 604/131 |
| 2007/0276327 A1 | 11/2007 | Kalafut et al. |
| 2008/0045925 A1 | 2/2008 | Stepovich et al. |
| 2008/0086087 A1 | 4/2008 | Spohn et al. |
| 2008/0167621 A1 | 7/2008 | Wagner et al. |
| 2008/0183131 A1 | 7/2008 | Duchon et al. |
| 2009/0112164 A1 | 4/2009 | Reilly et al. |
| 2009/0216192 A1 | 8/2009 | Schriver et al. |
| 2009/0247961 A1 | 10/2009 | Carlyon |
| 2009/0312744 A1 | 12/2009 | Keeley et al. |
| 2010/0222768 A1 | 9/2010 | Spohn et al. |
| 2010/0262078 A1 | 10/2010 | Blomquist |
| 2010/0331779 A1 | 12/2010 | Nystrom et al. |
| 2011/0275988 A1 | 11/2011 | Davis et al. |
| 2012/0089114 A1 | 4/2012 | Hemond et al. |
| 2012/0101472 A1 | 4/2012 | Schroeder et al. |
| 2012/0178629 A1 | 7/2012 | Hudson et al. |
| 2012/0203177 A1* | 8/2012 | Lanier, Jr. ............ G05D 7/0647 604/151 |
| 2012/0204997 A1 | 8/2012 | Winn et al. |
| 2012/0217231 A1 | 8/2012 | Moore et al. |
| 2012/0245560 A1 | 9/2012 | Hochman |
| 2013/0245604 A1 | 9/2013 | Kouyoumjian et al. |
| 2013/0261993 A1 | 10/2013 | Ruchti et al. |
| 2014/0027009 A1 | 1/2014 | Riley et al. |
| 2014/0276550 A1 | 9/2014 | Uram et al. |
| 2016/0030662 A1* | 2/2016 | Uber, III ............... A61M 5/007 600/431 |
| 2017/0035974 A1 | 2/2017 | Berry et al. |
| 2017/0258982 A1 | 9/2017 | Kemper |
| 2017/0290971 A1 | 10/2017 | Hedmann et al. |
| 2017/0343446 A1 | 11/2017 | Ciolkosz et al. |
| 2018/0133392 A1 | 5/2018 | Dembo et al. |
| 2019/0083699 A1 | 3/2019 | Spohn et al. |

FOREIGN PATENT DOCUMENTS

| | | |
|---|---|---|
| CA | 2234050 A1 | 4/1997 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| DE | 19919572 A1 | 11/2000 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0439711 B1 | 5/1995 |
| EP | 0869738 A1 | 10/1998 |
| EP | 2990073 A1 | 3/2016 |
| EP | 1838365 B1 | 2/2019 |
| FR | 2493708 A1 | 5/1982 |
| FR | 2561949 A1 | 10/1985 |
| GB | 201800 A | 8/1923 |
| GB | 2252656 A | 8/1992 |
| GB | 2328745 A | 3/1999 |
| JP | S60253197 A | 12/1985 |
| JP | S62216199 A | 9/1987 |
| JP | S63290547 A | 11/1988 |
| JP | H01207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H0584296 A | 4/1993 |
| JP | H07178169 A | 7/1995 |
| JP | H0849598 A | 2/1996 |
| JP | H0999034 A | 4/1997 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |
| WO | 9712550 A1 | 4/1997 |
| WO | 9820919 A1 | 5/1999 |
| WO | 9924095 A2 | 5/1999 |
| WO | 0061216 A1 | 10/2000 |
| WO | 03015633 A1 | 2/2003 |
| WO | 2004012787 A2 | 2/2004 |
| WO | 2004035116 A1 | 4/2004 |
| WO | 2005016165 A1 | 2/2005 |
| WO | 2005035995 A1 | 4/2005 |
| WO | 2006042093 A1 | 4/2006 |
| WO | 2007092618 A2 | 8/2007 |
| WO | 2007133942 A2 | 11/2007 |
| WO | 2009051995 A1 | 4/2009 |
| WO | 2010117841 A1 | 10/2010 |
| WO | 2011125303 A1 | 10/2011 |
| WO | 2012155035 A1 | 11/2012 |
| WO | 2013043868 A1 | 3/2013 |
| WO | 2014144651 A2 | 9/2014 |
| WO | 2014179326 A1 | 11/2014 |
| WO | 2014190264 A1 | 11/2014 |
| WO | 2015106107 A1 | 7/2015 |
| WO | 2015164783 A1 | 10/2015 |
| WO | 2016112163 A1 | 7/2016 |
| WO | 2016172467 A1 | 10/2016 |
| WO | 2016191485 A1 | 12/2016 |
| WO | 2017096072 A1 | 6/2017 |
| WO | 2017152036 A1 | 9/2017 |
| WO | 2018060505 A1 | 4/2018 |
| WO | 2018075379 A1 | 4/2018 |
| WO | 2018075386 A1 | 4/2018 |
| WO | 2018089882 A1 | 5/2018 |

OTHER PUBLICATIONS

Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).

Parker, K.J., et al., "A Particulate Contrast Agent With Potential for Ultrasound Imaging of Liver," Ultrasound in Medicine & Biology, vol. 13, Issue 9, pp. 555-566 (Sep. 1987).

Rosen, B.R. et al., "Perfusion Imaging with NMR Contrast Agents," Magentic Resonance in Medicine, vol. 14, No. 2, pp. 249-265, May 1, 1990.

Sablayrolles, J-L, "Cardiac CT: Experience from Daily Practice", Advance CT, A GE Healthcare Publication. Aug. 2004.

(56) References Cited

OTHER PUBLICATIONS

Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
"The Solution for Your IV Formulas", Valley Lab. Inc., E-39-15, 3399, 3400, 2646.
Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.
Wada, D.R. and Ward, D.S., "Open loop control of multiple drug effects in anesthesia", IEEE Transactions on Biomedical Engineering, vol. 42, Issue 7, pp. 666-677, 1995.
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.
Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.
Bae, et al."Aortic and Hepatic Contrast Medium Enhancement at CT—Part I, Prediction with a Computer Model", Radiology 1998;207:647-655.
Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).
Bae, K.T. et al, "Peak Contrast Enhancement in CT and MR Angiography: When Does it Occur and Why? Pharmacokinetic Study in a Porcine Model", Radiology, vol. 227, Jun. 2003, pp. 809-816.
Bae, K.T., et al., "Uniform vascular contrast enhancement and reduced contrast medium volume achieved by using exponentially decelerated contrast material injection method," Radiology, vol. 231, Issue 3, pp. 732-736, 2004.
Baker, Aaron; et al. "Fluid Mechanics Analysis of a Spring-Loaded Jet Injector." IEEE Transactions on Biomedical Engineering, vol. 46, No. 2, Feb. 1999.
Becker, C.R., et al., "Optimal contrast application for cardiac 4-detector-row computed tomography," Investigative Radiology, vol. 38, Issue 11, pp. 690-694 (Nov. 2003).
Blomley, M.J.K. and Dawson, P., "Bolus Dynamics: Theoretical and Experimental Aspects," The Brit. J. ofRadiology, vol. 70, No. 832, pp. 351-359 (Apr. 1997).
Brunette J.; et al., "Comparative rheology of low- and iso-osmolarity contrast agents at different temperature", Catheterization and Cardiovascular Interventions, 2008, vol. 71 Issue No. 1, 78-83.
Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.
Dardik, H. et al., "Remote Hydraulic Syringe Actuator," Arch. Surg., vol. 115, Issue 1, Jan. 1980.
Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).
"Digital Injector for Angiography", Sias. (Sep. 7, 1993).
Disposable Low-Cost Catheter Tip Sensor Measures Blood Pressure during Surgery, Sensor (Jul. 1989).
EZ CHEM Brochure, E-Z-EM, Inc. (Jul. 2007).
Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.
Flegal, K.M., et al., "Prevalence and trends in obesity among US adults," JAMA, 2002, vol. 288, Issue 14, pp. 1-4, (1999-2000).

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).
Fleischmann, D., "Contrast Medium Injection Technique," In: U. Joseph Schoepf: "Multidetector-Row CT of The Thorax," pp. 47-59 (Jan. 22, 2004).
Fleischmann, D., "Present and Future Trends in Multiple Detector-Row CT Applications; CT Angiography", European Radiology, vol. 12, Issue 2, Supplement 2, Jul. 2002, pp. s11-s15.
Gardiner, G. A., et al., "Selective Coronary Angiography Using a Power Injector," AJR Am J Roentgenol., vol. 146, Issue 4, pp. 831-833 (Apr. 1986).
Garrett, J. S., et al., "Measurement of cardiac output by cine computed tomography," The American Journal of Cardiology, vol. 56, Issue 10, pp. 657-661, 1985.
Gembicki, F.W., "Vector Optimization for Control with Performance and Parameter Sensitivity Indices," PhD Thesis Case Western Reserve University, 1974.
Gentilini A., et al., "A new paradigm for the closed-loop intraoperative administration of analgesics in humans," IEEE Transactions on Biomedical Engineering, vol. 49, Issue 4, pp. 289-299 (Apr. 2002).
Gerlowski L.E. and Jain R.K., "Physiologically Based Pharmacokinetic Modeling: Principles and Applications," Journal of Pharmaceutical Sciences, vol. 72, pp. 1104-1125, Oct. 1983.
Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).
Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109 (Feb. 1992).
Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.
Hansen, P.C, Regularization tools: a MATLAB package for analysis and solution of discrete ill-posed problems, Numerical Algorithms, vol. 6, Issue 1, pp. 35, 1994.
Hansen, P.C., "The truncated SVD as a method for regularization," BIT Numerical Mathematics, vol. 27, Issue 4, pp. 534-555, 1987.
Harris P., H. D. "The Human Pulmonary Circulation," Edinburgh, Churchill Livingstone, (Appendix I), 1986.
Hayes, M., "Statistical Digital Signal Processing and Modeling", New York, New York, Wiley and Sons, 1996, pp. 154-177, (Prony's method).
Heiken; J.P. et al., "Dynamic Contrast-Enhanced CT of the Liver: Comparison of Contrast Medium Injection Rates and Uniphasic and Biphasic Injection Protocols", Radiology, May 1993, vol. 187, No. 2, pp. 327-331.
"Infus O.R. Multi-Drug Syringe Pump with Smart Labels," Bard MedSystems Division Inc., pp. 2693-2696 (2005).
"International Preliminary Report on Patentability from PCT Application No. PCT/US2018/048338", Mar. 12, 2020.
Ireland, M.A., et al., "Safety and Convenience of a Mechanical Injector Pump for Coronary Angiography,"Catheterization and Cardiovascular Diagnosis, vol. 16, Issue 3, pp. 199-201 (1989).
Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.

(56) References Cited

OTHER PUBLICATIONS

Krieger, R. A., "CO2-Power-Assisted Hand-Held Syringe: Better Visualization during Diagnostic and InterventionalAngiography," Cathet Cardiovasc Diagn., vol. 19, Issue 2, pp. 123-128 (Feb. 1990).
Liebel-Flarsheim Company, "Angiomat 6000 Digital Injection System—Operator's Manual", Document No. 600950, Rev. 1, Jan. 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, 2003.
Mark V/Mark V Plus Injector Operation Manual KMP 805P Rev. B. Medrad, Inc, 1990.
McClellan, J.H., "Parametric Signal Modeling," Chapter 1 in Advanced Topics in Signal Processing, Pentice-Hall, Englewood Cliffs, NJ (1988).
MCT and MCT Plus Injection Systems Operation Manual KMP 810P, Medrad, Inc, 1991.
Morden Peter.; et al., "The Role of Saline Flush Injection Rate in Displacement of CT Injectable Peripherally Inserted Central Catheter Tip During Power Injection of Contrast Material", AJR, Jan. 2014, 202, W13-W18.
Neatpisarnvanit, C. and Boston, J.R., "Estimation of plasma insulin from plasma glucose", IEEE Transactions on Biomedical Engineering, vol. 49, Issue 11, pp. 1253-1259, 2002.
Swiss; Medical Care., "CT Expres Contrast Media Delivery System Operation Manual Rev 1", 2004.
Ulrich; Medical., "Instructions for Use for ulrichINJECT CT motion—CT Contrast Media Injector", 2018.

\* cited by examiner

ZADJUSTB = 0

QDOTB(i) = ((PreviousSyringeAreaB*(DELTAZB-ZADJUSTB)/TimeIncrement- DELTACAPACITANCEB/TimeIncrement ))*2.54^3 : PRINT "QDOTB(i) = ";QDOTB(i) ' saline QDOTA(i) = (- DELTACAPACITANCEB/TimeIncrement )*2.54^3 : PRINT "QDOTA(i) = ";QDOTA(i)' contrast QDOT(i) = QDOTA(i) + QDOTB(i) ' total flow DO UNTIL QDOT(i)<= SyringeBFlowRatesetpoint QDOTB(i) = ((PreviousSyringeAreaB*(DELTAZB-ZADJUSTB)/TimeIncrement- DELTACAPACITANCEB/TimeIncrement ))*2.54^3 : PRINT "QDOTB(i) = ";QDOTB(i)

QDOT(i) = QDOTA(i) + QDOTB(i)

ZADJUSTB = ZADJUSTB+.0001 ' fine increment adjustment of saline piston position

LOOP

TOTALDELTAZB = TOTALDELTAZB + DELTAZB-ZADJUSTB-.0001: PRINT "TOTALDELTAZA = ", TOTALDELTAZA:
TOTALDELTAZA(I) = TOTALDELTAZA

DELTAZB is the coarse adjustment for the saline piston

FIG. 54

FLUID PATH IMPEDANCE ASSESSMENT FOR IMPROVING FLUID DELIVERY PERFORMANCE

CROSS-REFERENCE TO RELATED APPLICATIONS

This application is a § 371 national phase application of PCT International Application No. PCT/US2018/048338, filed Aug. 28, 2018, and claims priority to United States Provisional Patent Application Nos. 62/552,447, entitled "Fluid Path Impedance Assessment for Improving Fluid Delivery Performance", filed Aug. 31, 2017, 62/552,570, entitled "Method for Using Variable Pressure Limit in Viscosity Transitions", filed Aug. 31, 2017, and 62/552,631, entitled "System and Method for Reduction of Flow Overrate in a Multiphase Fluid Injection", filed Aug. 31, 2017, the contents of each of which are incorporated herein by reference, in their entirety.

BACKGROUND

Field of the Technology

The present disclosure is directed to various systems and methods for impedance modeling, assessment, prediction, utilization, and/or control for a fluid injection system having a fluid pumping device for fluid delivery applications in medical diagnostic and therapeutic procedures.

DESCRIPTION OF RELATED ART

In many medical diagnostic and therapeutic procedures, a physician or trained clinician injects fluid into a patient. For example, a physician may inject saline and/or an imaging contrast agent into a patient to help improve the visibility of internal body structures in one or more X-ray, CT, MR. PET or other images that are taken during the procedure. To inject the saline and/or contrast agent, the clinician may use a manual injection syringe or may, alternatively, use a powered fluid injection system. A catheter is coupled to the manual injection syringe or injection device and is used to inject the saline and/or contrast agent into the patient (such as into a vessel in the patient's hand or arm). The contrast agent and saline are provided from separate sources, such as bags, bottles, or syringes, and, in certain cases, may be mixed together before injection into the patient. However, several problems may develop during use of certain flexible capacitive pressure injection systems and syringes, including fluid flow rate spikes or real-time injection ratio inaccuracies.

One complication that is often created comes within the definition of system boundaries. In a medical fluid injection system, some system definitions assume that once the fluid leaves a catheter and enters a patient's veins, the fluid has left the system. However, this fluid may exit the catheter with a significant velocity, which means a significant kinetic energy. So while this energy could be recovered from the fluid if the fluid remained in the system, the energy is considered to be lost from the system since the fluid leaves the system. The kinetic energy is likely ultimately dissipated as heat in the patient. The useful work of the system is to deliver the fluid at a desired flow rate, for example, several milliliters per second. The smaller the exit area of the catheter, the higher the velocity of the exiting fluid and the more energy that must be input by the system to achieve that desired flow rate. Many different factors can contribute to the impedance of a medical fluid injection system, which can affect the amount of energy required for fluid delivery and/or stored by the medical fluid injection system.

As shown in FIG. 7, at the start of an injection protocol, no pressure is applied to the contrast agent 710 or saline 712, resulting in no flow through the fluid injector system. Any fluid that is present downstream in the fluid path, for example at 713, is a result of priming of the system (usually with saline) during the initial setup. As shown in FIG. 8, pressure is then applied to the contrast agent 710 resulting in a pressure build up and initial backflow of contrast agent 710 into the saline fluid path 712 at point A. As a result, the flow rate of the contrast agent 710 to the patient may be reduced due to the effect of backflow and expansion in the contrast agent 710 bag or syringe and the saline 712 bag or syringe due to the injection fluid pressure. Further, the contrast agent 710 bag or syringe and the saline 712 bag or syringe may expand depending on the particular capacitance (a component of impedance) of the respective bag or syringe. As shown in FIG. 9, the flow rate and pressure of the contrast agent 710 may continue to increase, thereby stabilizing the pressure in the injector system and delivering contrast to the patient. As shown in FIG. 10, when the contrast agent delivery stops and the saline delivery beings, the pressure applied to the saline 712 must be increased further such that the saline 712 is directed to flow to point B. As the saline flow continues, the saline 712 will displace the contrast agent 710 from the fluid path line to the patient. When the saline 712 piston begins immediately after the contrast agent 710 injection stops and once the saline 712 replaces contrast agent 710 in the significant portions of the fluid path, the flow rate of the saline 712 increases rapidly (higher than the flow rate programmed for the saline 712), sending an increased amount of saline 712 to mix with the contrast agent 710. This increased flow rate may occur because the saline 712 is less viscous than the contrast agent 710, which causes the resistance of the fluid path (a component of impedance) to decrease. With a decreased resistance, the pressure stored in the capacitance of the syringe or syringes may drive the saline 712 at an increased flow rate. This increased flow rate can cause a rapid fluid acceleration in the catheter. The syringes or bags of the injector system will begin to deflate as the pressure within the syringes or bags decreases due to the increased flow of contrast agent 710 and/or saline 712. The rapid increase in flow rate for the saline 712 may create a transition to turbulence that causes the resistance to slightly rise again, potentially causing oscillations in the flow. Eventually, a stable flow rate is reached at a lower equilibrium pressure. However, due to the initial backflow and increased pressure in the fluid injector system, an increased injection pressure and/or flow rate of contrast agent 710 or saline 712 may be experienced.

With further reference to FIG. 7 and the injection process described above, also due to the initial backflow and increased pressure stored in the capacitance of the fluid injector system, accurate flow rates of contrast agent 710 and saline 712 are not always provided. Accurate flow rates of the contrast agent 710 and saline 712 may be achieved on average during the full course of the injection protocol. However, for short periods of time until the system achieves a steady state, the contrast agent 710 and saline 712 fluid flow rates may be ramping, slowing down, peaking, and may not be particularly precise. In one scenario, the contrast agent 710 injection may be followed by the saline 712 injection, which may cause the flow rate for saline 712 to be too high, aka an "overrate." In another scenario, a dual flow simultaneous injection of contrast agent 710 and saline 712 may cause inaccurate ratios of contrast agent 710 and saline 712 until the system stabilizes.

An additional factor that may contribute to the problem of inaccurate fluid mixing ratios in multi-fluid injector systems is the backflow of fluid that occurs in injections where the viscous contrast agent 710 is injected at a higher ratio than the less viscous saline 712. In such a scenario, before a uniform fluid flow is established, the fluid pressure of the more viscous contrast agent 710 that is injected at a higher ratio may act against the fluid pressure of the less viscous saline 712 that is injected at a lower ratio to force the contrast agent 710 to reverse the desired direction of flow. After injections begin, pressures equalize and the fluid injection system achieves a steady state operation where the contrast agent 710 and saline 712 are injected at a desired ratio. However, in small volume injections, steady state operation may not be achieved prior to the completion of the injection process and the fluid mixing ratio of contrast agent 710 and saline 712 being delivered may not be accurately achieved. Thus, even though a desired ratio of contrast agent 710 and saline 712 may be 80% contrast agent 710 to 20% saline 712, the actual ratio due to backflow of contrast agent 710 into the saline 712 may be initially higher.

While various approaches exist for characterizing the performance of a fluid delivery system and correlating the desired performance with actual performance in terms of fluid flow rate and volume delivered, these approaches do not address the differences between desired and actual performance due to impedance and/or capacitance of the fluid delivery system in a comprehensive manner. As a result, existing approaches fail to address the under-delivery or over-delivery of fluid resulting from system impedance and/or capacitance. As a result, less than optimal injection boluses or volumes may result and/or operation of the fluid delivery system can result in relatively large amounts of wasted fluid.

There is a need in the art for improved methods and systems for controlling impedance in a multiphase injection in a manner which accounts for such fluid differences. For example, such systems may address problems of differences in flow velocity which can occur during an injection. Desirably, a multiphase injection is performed at a substantially constant flow rate and volume without discontinuities, spikes, or drops in flow rate between phases. The systems and methods disclosed herein are adapted to address such issues.

BRIEF SUMMARY

In view of the foregoing, a need exists for an improved fluid injection system for fluid delivery applications in medical diagnostic and therapeutic procedures. There is an additional need in the medical field for a fluid injection system that provides a modeling, assessment, prediction, anticipation, compensation, control, and/or utilization of system impedance and related energy storage and changes thereof for safety assessment or fluid delivery performance improvement.

In one example, fluid injection systems utilize a method of improving fluid delivery performance, the method comprises modeling one or more factor that affects impedance of the fluid injection system based upon one or more known, estimated and measured parameter; initiating delivery of at least a first fluid to a patient at a first flow rate; measuring one or more characteristic of the fluid delivery; modeling one or more factor that affects impedance of the fluid injection system based upon one or more measurement of the one or more characteristic of the fluid delivery; and adjusting one or more characteristic of the fluid injection system based upon the one or more factor that affects impedance of the fluid injection system modeled on the one or more known, estimated and measured parameter or modeled on the one or more measurement of the one or more characteristic of the fluid delivery to improve fluid delivery performance. The method may further comprise initiating delivery of at least a second fluid to the patient at a second flow rate. The method may further comprise making the adjustment prior to fluid delivery or during delivery of either both of the first and second fluid or the first or second fluid individually.

In this and other methods disclosed herein, the system may be configured to notify an operator of the fluid injection system of at least one adjustment made or suggested by the one or more factor that affects impedance of the fluid injection system modeled on the one or more known, estimated and measured parameter or modeled on the one or more measurement of the one or more characteristic of the fluid delivery. Further, the one or more parameter may be temperature, viscosity, pressure, bulk modulus, concentration, catheter size, hydraulic resistance, desired flow rate, and/or system capacitance; and the one or more characteristic of the fluid delivery may be temperature, viscosity, pressure, bulk modulus, hydraulic resistance, actual flow rate, and/or system capacitance.

In this method, the system may be configured to re-measure one or more characteristic of the fluid delivery; re-model one or more factor that affects impedance of the fluid injection system based upon one or more known, estimated and measured parameter or one or more re-measurement of the one or more characteristic of the fluid delivery; and re-adjust the one or more characteristic of the fluid injection system based upon the one or more factor that affects impedance of the fluid injection system re-modeled on the one or more known, estimated and measured parameter or re-modeled on the one or more re-measurement of the one or more characteristic of the fluid delivery during delivery of either both of the first and second fluid or the first or second fluid individually.

In this method, the system may be configured to continuously re-measure one or more characteristic of the fluid delivery; continuously re-model one or more factor that affects impedance of the fluid injection system based upon one or more known, estimated and measured parameter or one or more re-measurement of the one or more characteristic of the fluid delivery; and continuously re-adjust the one or more characteristic of the fluid injection system based upon the one or more factor that affects impedance of the fluid injection system re-modeled on the one or more known, estimated and measured parameter or re-modeled on the one or more re-measurement of the one or more characteristic of the fluid delivery during delivery of either both of the first and second fluid or the first or second fluid individually.

In one example, fluid injection systems utilize a method of improving fluid delivery performance, the method comprises delivering at least a first fluid into the patient's blood vessel at a first flow rate; delivering at least a second fluid into the patient's blood vessel at a second flow rate; and adjusting at least one characteristic of the fluid injection system based upon at least one aspect of the fluid injection system impedance to improve the fluid delivery performance of the fluid injection system.

In another example, fluid injection systems utilize a method of relieving pressure in the fluid injection system, the method comprises (a) conducting an injection process using the fluid injection system; (b) recording an initial position of a piston in at least one syringe of the fluid injection system; (c) removing power from a motor arrangement of the fluid injection system for a predetermined amount of time to permit a piston of the fluid injection system to be pushed towards a distal end of the at least one syringe in the fluid injection system; (d) supplying power to the motor arrangement of the fluid injection system; (e) recording a second displacement position of the piston in the at least one syringe; and (f) conducting one of the following: repeating items (b)-(e) when the piston of the at least one syringe no longer moves within the at least one syringe when power is removed from the motor arrangement; or repeating items (b)-(e) for a predetermined amount of time.

In the examples disclosed herein, fluid injection systems utilize methods that model and adjust factors that affect impedance and prevent or reduce backflow, reduce the likelihood of fluid flow rate spikes and provide more accurate flow rates and mixing ratios of fluids; each may be repeated or happen essentially continuously during an injection. The adjustments may be determined before the injection or determined and/or adjusted during the injection. The determination may include sensor feedback commonly used in injectors such as pressure and position feedback as well as other sensors listed herein. In all cases, the user can be notified of adjustments through on-screen notices and/or through the recordation of the injection data by the electronic control device of the injector at the conclusion of the injection, such as through a report.

In one embodiment of the present disclosure, fluid injection systems utilize a method of delivering multiple fluids, the method comprises providing a fluid delivery system for a multiphase fluid injection comprising at least a first syringe containing a first fluid, at least a second syringe containing a second fluid, a fluid conduit for conducting fluid from the first syringe and the second syringe to a patient, and an injector comprising at least a first piston for expelling fluid from the first syringe and at least a second piston for expelling fluid from the second syringe. The method advances the first piston to expel fluid from the first syringe into the conduit during a first phase of the injection, measures one or more parameter of the injection during the first phase of the injection, calculates a retraction distance for the second piston based on the one or more measured parameter and a desired fluid flow rate, retracts the second piston by the calculated retraction distance to a retracted position; and performs a second phase of the injection by advancing the second piston from the retracted position through at least a portion of the second syringe to expel fluid from the second syringe and into the conduit. The one or more measured parameter can be temperature, viscosity, pressure, bulk modulus, catheter size, hydraulic resistance, actual flow rate, system capacitance, system impedance, and factors that affect system capacitance, impedance and hydraulic resistance. The method can also calculate a new flow rate for the second phase of the injection based on the one or more measured parameter and perform the second phase of the injection at the new flow rate.

In some embodiments of the present disclosure, fluid injection systems that utilize a method of delivering multiple fluids to a patient via a multi-phase injection with the fluid injector are provided. The method comprises injecting a first fluid during a first phase of the injection with a first pressure limit, wherein the first fluid has a first viscosity; and injecting a second fluid during a second phase of the injection with a second pressure limit, wherein the second phase has a second viscosity. The first viscosity is greater than the second viscosity. The second pressure limit is less than the first pressure limit in order to minimize a flow rate fluctuation in a fluid path at a transition from the first phase to the second phase.

This method may further comprise deriving the second pressure limit from at least one of a table or equation or pressure measured during the first phase. The second pressure limit may be derived according to at least one or more of: characteristics of the first fluid, characteristics of the second fluid, catheter gauge, a predetermined desired flow rate, a position of a piston in a syringe of the fluid injector, and combinations thereof.

This method may further comprise applying the second pressure limit while injecting an initial amount of the second fluid and applying the first pressure limit while injecting a remaining amount of the second fluid. A third pressure limit, different from the first and second pressure limits may also be derived and applied by the injector while injecting the remaining amount of the second fluid.

It is expressly understood that all embodiments disclosed herein can apply to syringes as well as different types of pumps with at least two fluids, such as piston pumps or peristaltic pumps. Combinations of different pumps may also be utilized in multiphase fluid delivery injections where fluid flow rates and phase transitions may be controlled using calculation processes and various methods described herein.

These and other features and characteristics of a fluid injection system, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure.

BRIEF DESCRIPTION OF THE DRAWINGS

FIG. 52A reflects characteristics of linear elastic material for the syringe, piston, and plunger. FIG. 52B illustrates characteristics of non-linear materials for the same components;

FIG. 54 is a pseudocode for implementing aspects of a fluid delivery procedure to reduce overrate by adjusting piston position according to an example of the disclosure;

DESCRIPTION OF THE DISCLOSURE

Figure 1:
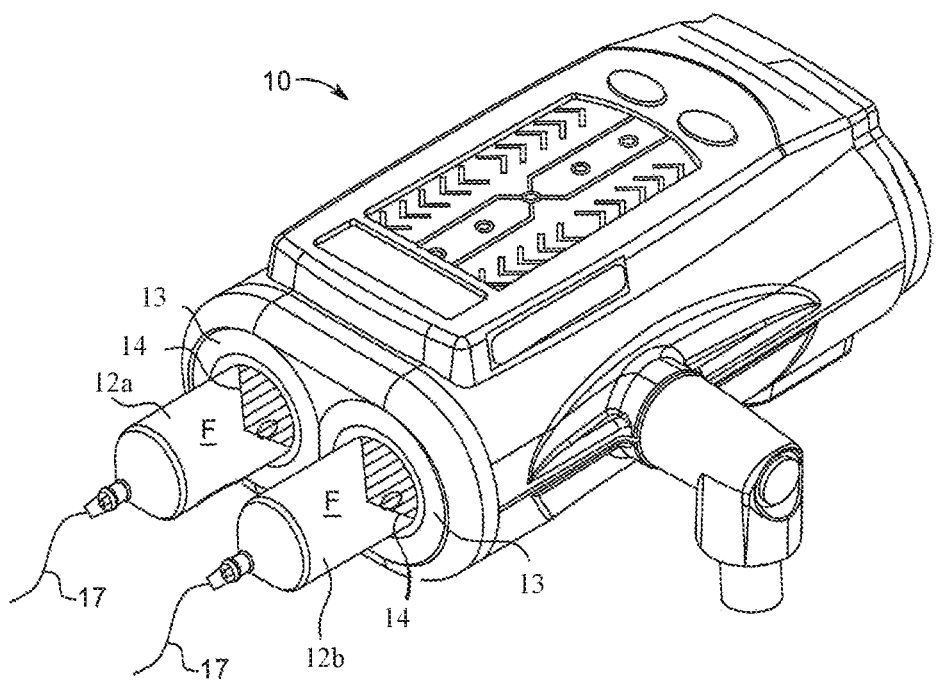
FIG. 1 is a perspective view of a fluid delivery system according to an example of the present disclosure.

As used herein, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the claimed invention can assume various alternative orientations.

All numbers used herein are to be understood as being modified in all instances by the term "about." The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The term "at least" means "greater than or equal to."

The term "includes" is synonymous with "comprises."

When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends. The term "open" when used to refer to a fluid delivery component means that the system is in fluid connection with an outlet, for example through a nozzle or the open end of a tubing component or catheter. In an open system, fluid flow may be constrained, for example by forcing a fluid through a small diameter fluid path where flow may be determined by physical parameters of the system and the fluid, such as tubing diameter, fluid path constrictions, applied pressure, viscosity, etc. The term "closed" when used to refer to a fluid delivery component means that the system is not in fluid connection with an outlet, for example where fluid flow is stopped by a valve, such as a stopcock, high crack pressure valve, pinch valve, and the like.

Impedance is a term generally used to describe how energy from a source of energy is used in or moves through a system. The energy output or loss from a system is either in the form of work done or heat through frictional losses. This energy, ultimately dissipated as heat, may be called resistive, frictional, or dissipative loss. There are several forms of energy storage. One form of energy storage is potential energy, for example, a capacitance in electricity, compression or strain energy in a solid, liquid, or a gas, or height differences in a hydraulic system. Another form of storage energy is kinetic energy, for example, inductance in electrical systems and motion of a mass in mechanical or fluid systems.

Impedance as an engineering term is generally meant to designate the relationship between a driving force and a resulting action. For example, in electrical engineering, it is the relationship between voltage and current. In mechanics it is the relationship between force and motion or torque and rotational motion. In fluid flows it is between pressure and flow. One might also define it as the resistance to the movement of energy through a system. Transfer function is a term often used to describe the relationship between driving force or action in one form of energy and driving force or action into a different form of energy. For example an electrical current in a motor creates mechanical torque on the shaft, so electrical energy is inputted and transferred or transformed into mechanical energy output.

In this disclosure, impedance is used to encompass all relationships between input actions, forces, or energies and output actions, forces, or energies and includes stored and non-recoverable actions, forces, or energies of all types. It also includes inaction or delayed action, such as mechanical slop.

Impedance may be relatively linear in the common or designed operating ranges and so may be represented by a simple constant. However, many impedances are not. Many impedances depend upon the operating conditions, such as temperature, position, or operating history of one or more aspects of the system. Some impedances may be represented by one or more response surfaces. One example of a non-linear impedance is mechanical slack or slop, in which a mechanical effector initially has a gap between itself and the recipient part on which it is to act. The effector initially moves with no force on the recipient part. Once the slack is taken up, it then exerts a force on the recipient part. Stiction or static friction is similarly non-linear. It is common for a syringe plunger to not move when force is initially applied to it by a piston. Once the force exceeds a breakaway force, the plunger moves with the piston, although in some conditions it may be a jerky motion alternating between movement and non-movement. Further, impedances mentioned herein are not necessarily static or fixed over time or for a particular situation, because in some instances some aspects of impedance will affect the fluid viscosity or density in each segment of each element of the fluid path. Impedances may also be dependent upon (i) prior fluid delivery causing various fluids to already be in the fluid paths, (ii) heat accumulation in the motor over time, (iii) pressures causing plastic deformation over time, or (iv) plunger position.

It is to be understood that the disclosure may assume alternative variations and sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the examples disclosed herein are not to be considered as limiting.

For the purposes of the description hereinafter, spatial orientation terms, if used, shall relate to the referenced example as it is oriented in the accompanying drawings, figures, or otherwise described in the following detailed description. However, it is to be understood that the examples described hereinafter may assume many alternative variations and examples. It is also to be understood that the specific systems illustrated in the accompanying drawings, figures, and described herein are simply exemplary and should not be considered as limiting.

Referring to the drawings in which like reference characters refer to like parts throughout the several views thereof, several systems and methods are provided for reducing the likelihood of fluid flow rate spikes and delivering more accurate flow rates and mixing ratios of fluids, informing the operator what flow rates are possible and what changes may be made to achieve desired or possible flow rates. In a typical multi-fluid injection procedure, an injection fluid, such as saline, is first used to fill the lines with fluid and check patency. Next, a contrast agent is usually delivered from a contrast agent source using a powered or manual injector. The injected contrast agent is delivered to a desired site in a patient's body through a catheter inserted into the patient's body, such as the patient's arm. Once the contrast agent is delivered to the desired site, that area is imaged using a conventional imaging technique, such as CT, MR, nuclear medicine, ultrasonic, or angiography imaging or scanning. The contrast agent becomes clearly visible against the background of the surrounding tissue. However, it is generally desirable to reduce the amount of contrast agent that is given to the patient while maintaining an effective amount of contrast necessary for effective imaging. By supplementing the overall contrast agent delivery procedure with saline, the saline flushes the contrast agent to the area of interest and in addition, hydrates the patient and aids the body in removing the contrast agent. Introduction of saline at clinically significant pressures and flow rates also allows higher flow rates to be achieved at lower pressure settings on the injector. For some procedures, simultaneous, prior, or subsequent saline delivery is necessary to prevent too high a concentration of contrast from causing artifacts, inaccuracies, and/or poor image quality or to reduce overall contrast dose to the patient.

With reference to FIG. 1, a fluid injector 10, such as an automated or powered fluid injector, is adapted to interface with and actuate one or more syringes 12, which may be filed with a fluid F, such as contrast media, saline solution, or any desired medical fluid. The injector 10 may be used during a medical procedure to inject the medical fluid into the body of a patient by driving a plunger 14 of each syringe 12 with a drive member, such as piston 19 (shown in FIG. 2), such as a linear actuator or a piston element. The injector 10 may be a multi-syringe injector having two, three or more syringes, wherein the several syringes 12 may be oriented in a side-by-side or other relationship and may be separately actuated by respective drive members/pistons 19 associated with the injector 10. In examples with two or more syringes, for example, arranged in a side-by-side or other relationship and filled with two different fluids, the injector 10 may be configured to deliver fluid from one or both of the syringes 12, sequentially or concurrently. According to one embodiment, the fluid injector 10 may be a dual head injector having two syringes 12a and 12b, a first syringe 12a for delivering a contrast agent or other medical fluid and a second syringe 12b for delivering saline or other medically approved flushing agent to flush the contrast agent to the patient. In other embodiments, the fluid injector 10 may have three syringes 12, a first and second syringe for delivering one or two different contrast agents or other medical fluid and a third syringe for delivering saline or other medically approved flushing agent to flush the contrast agent to the patient.

According to various embodiments, the fluid injector 10 may be configured to deliver the contrast and saline separately (e.g., delivering a specific volume saline over a specific time followed by delivering a specific volume of contrast over a specific time, followed by a second volume of saline over a specified time to flush the contrast agent from the tubing into the patient). According to various embodiments, the fluid injector 10 may be configured to deliver the contrast and saline separately or as a mixture (e.g., delivering a specific volume saline over a specific time followed by delivering a specific volume of contrast or a specified ratio of contrast and saline (i.e., in a "dual flow" process) over a specific time, followed by a second volume of saline over a specified time to flush the contrast agent from the tubing into the patient). A technician may program a specific injection protocol into the injector (or use a pre-written protocol) to deliver the desired volumes of saline, contrast, specific ratios of contrast and saline mixtures, etc., at a desired flow rate, time, and volume for each solution. The fluid injector 10 may have at least one bulk fluid source (not shown) for filling the syringes 12a,b with fluid and in certain embodiments, the fluid injector 10 may have a plurality of bulk fluid sources, one for each of the plurality of syringes, for filling each of the plurality of syringes with the desired fluid.

To enable effective simultaneous flow delivery of first and second injection fluids, such as contrast agent and saline, substantially equal pressure must be present in each delivery line. In a powered injection system described above, it is desirable to actuate the plunger elements substantially simultaneously in simultaneous flow delivery applications to equalize the pressure in each line. If the injector is operated with differential pressure in each delivery line of the fluid path set, the fluid in the lower pressure line may be stopped or reversed until sufficient pressure is achieved in the lower pressure line and its associated syringe to enable flow in a desired direction. This time delay could reduce the usefulness of the image quality. The fluid in the lower pressure line may also begin to store fluid pressure energy (a component of impedance). As the stored fluid pressure energy in the lower pressure line continues to build, the lower pressure will eventually achieve the same pressure as the higher pressure fluid. Subsequently in the injection, due to the stored fluid pressure energy in the lower and high pressure syringes and lines, the flow rate of the fluid will rapidly accelerate into the catheter tubing as the viscosity and, thus, resistance of, the fluid in the line changes.

A fluid path set 17 may be in fluid communication with each syringe 12 to place each syringe in fluid communication with a catheter for delivering the fluid F from each syringes 12 to a catheter (not shown) inserted into a patient at a vascular access site. In certain embodiments, fluid flow from the one or more syringes 12 may be regulated by a fluid control module (not shown) that operates various valves, stopcocks, and flow regulating structures to regulate the delivery of the saline solution and contrast to the patient based on user selected injection parameters, such as injection flow rate, duration, total injection volume, and ratio of fluids from the syringes 12, including specific ratios of each fluid in a dual flow injection protocol.

Figure 2:
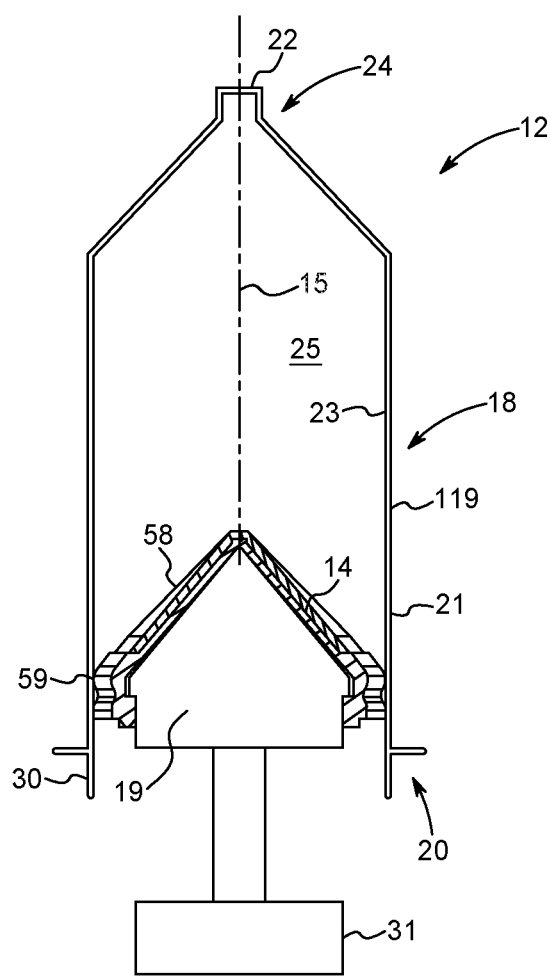
FIG. 2 is a side cross-sectional view of a syringe configured for use with the fluid delivery system of FIG. 1.

With continued reference to FIG. 2, the drive member 19, such as a reciprocally driven piston moved by a motor 31, may be configured to extend into and from the respective syringe port 13 through an opening in the front end of the injector housing. In fluid injector embodiments comprising a plurality of syringes, a separate drive member/piston 19 may be provided for each syringe 12. Each drive member/piston 19 is configured to impart a motive force to at least a portion of the syringe 12, such as the plunger 14 or a distal end of a rolling diaphragm syringe (for example, as described in PCT/US2017/056747; WO 2016/172467; and WO 2015/164783, the disclosures of which are incorporated herein by reference). The drive member or piston 19 may be reciprocally operable via electro-mechanical drive components such as a ball screw shaft driven by the motor 31, a voice coil actuator, a rack-and-pinion gear drive, a linear motor, and the like. The motor 31 may be an electric motor.

Examples of suitable front-loading fluid injectors 10 are disclosed in U.S. Pat. Nos. 5,383,858; 7,553,294; 7,666,169; 9,173,995; 9,199,033; and 9,474,857; and in PCT Application Publication Nos. WO 2016/191485 and WO 2016/112163, the disclosures of which are incorporated by reference in their entirety.

Having described the general structure and function of specific embodiments of the fluid injector 10, an embodiment of syringe 12 configured for use with the injector 10 is described with reference to FIG. 2. The syringe 12 generally has a cylindrical syringe barrel 18 formed from glass, metal, or a suitable medical-grade plastic. The barrel 18 has a proximal end 20 and a distal end 24, with a sidewall 119 extending there between along a length of a longitudinal axis 15 extending through a center of the barrel 18. In some examples, the distal end 24 may have a conical shape that narrows in a distal direction from the cylindrical barrel 18. A nozzle 22 extends from the distal end 24. The barrel 18 has an outer surface 21 and an inner surface 23 with an interior volume 25 configured for receiving the fluid therein. The proximal end 20 of the barrel 18 may be sealed with the plunger 14 that is reciprocally movable through the barrel 18 by reciprocal movement of the corresponding piston 19 or drive member. The plunger 14 forms a liquid-tight seal against the inner surface 23 of the barrel 18 as the plunger 14 is advanced through the barrel 18.

With continued reference to FIG. 2, the proximal end 20 of the syringe 12 is sized and adapted for being removably inserted in a syringe port 13 of the injector 10 (shown in FIG. 1). In some examples, the proximal end 20 of the syringe 12 defines an insertion section 30 that is configured to be removably inserted into the syringe port 13 of the injector 10 while the remaining portion of the syringe 12 remains outside of the syringe port 13.

In one embodiment, the syringe 12 may be made of any suitable medical-grade plastic or polymeric material, desirably a clear or substantially translucent plastic material. The material of the syringe 12 is desirably selected to meet the required tensile and planar stress requirements, water vapor transmission, and chemical/biological compatibility. Exemplary syringes suitable for use with the injector 10 depicted in FIG. 1 are described in U.S. Pat. Nos. 5,383,858; 6,322,535; 6,652,489; 9,173,995; and 9,199,033, the disclosures of which are all incorporated by reference in their entirety.

Figure 3:
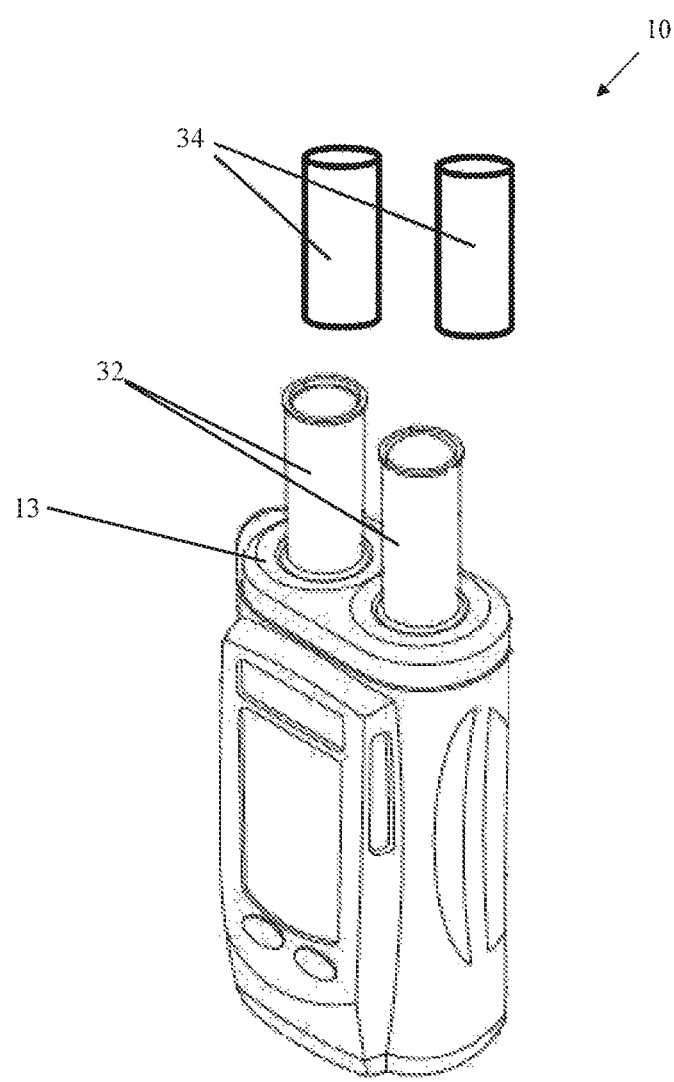
FIG. 3 is a perspective view of a fluid delivery system according to another example of the present disclosure.

In some examples, such as shown in FIG. 3, the injector 10 may be configured for receiving and retaining a pressure jacket 32 within each syringe port 13 of the injector 10. While FIGS. 1 and 3 illustrate fluid injectors 10 with two syringe ports 13, which for the injector 10 shown in FIG. 3 each having a corresponding pressure jacket 32, other examples of the fluid injector 10 may include a single syringe port 13 and optionally, a corresponding pressure jacket 32 or more than two syringe ports 13 with an optional corresponding number of pressure jackets 32. In embodiments comprising pressure jackets, each pressure jacket 32 may be configured to receive a syringe, such as a syringe for an angiographic (CV) procedure, or a rolling diaphragm syringe 34 (suitable examples of which are described in PCT/US2017/056747; WO 2016/172467; and WO 2015/164783). A fluid path set, similar to the fluid path set 17 shown in FIG. 1, may be fluidly connected with a discharge end of each rolling diaphragm syringe 34 for delivering fluid from the syringes 34 through tubing connected to a catheter, needle, or other fluid delivery connection (not shown) inserted into a patient at a vascular access site. According to various embodiments, the syringe 12 or 34 may be a pre-filled syringe, i.e., the syringe may be prefilled with a medical fluid, such as a contrast agent or saline, when provided by the syringe manufacturer. According to certain embodiments, the pre-filled syringe may be required to be spiked or otherwise punctured at the discharge end prior to an injection procedure to allow fluid to be expelled from the syringe into a fluid line to the patient, as described herein.

Figure 4:
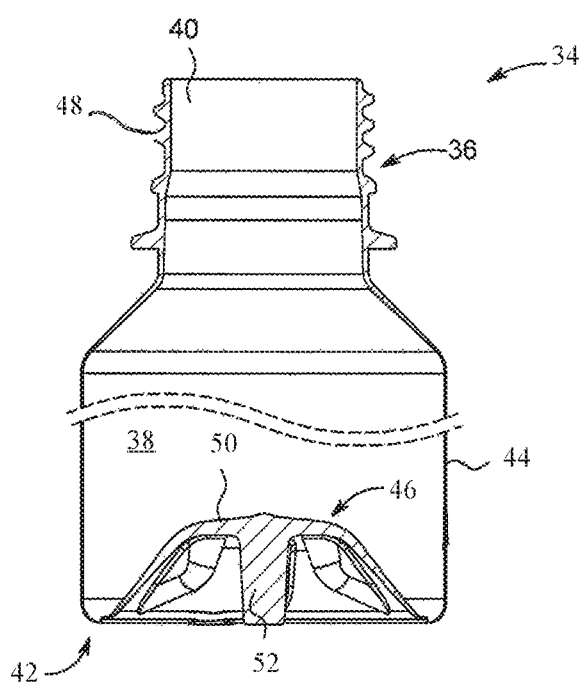
FIG. 4 is a side cross-sectional view of a syringe configured for use with the fluid delivery system of FIG. 3.

With reference to FIG. 4, the rolling diaphragm syringe 34 generally includes a hollow body 36 defining an interior volume 38. The body 36 has a forward or distal end 40, a rearward or proximal end 42, and a flexible sidewall 44 extending there between. The proximal end 42 may be configured to act as piston to pressurize the syringe interior to draw in or expel fluid therefrom, as described herein. The sidewall 44 of the rolling diaphragm syringe 34 defines a soft, pliable or flexible, yet self-supporting body that is configured to roll upon itself, as a "rolling diaphragm", under the action of a drive member or piston of the fluid injector 10. The drive member/piston 19 may be configured to releasably engage a drive member engagement portion 52 at the proximal end 42 of the rolling diaphragm syringe 34 (examples of which are described in PCT/US2017/056747). In operation, the sidewall 44 is configured to roll such that its outer surface is folded and inverted in a radially inward direction as the drive member/piston 19 moves the proximal end 42 in a distal direction and unrolled and unfolded in the opposite manner in a radially outward direction as the drive member/piston 19 retract the proximal end 42 in a proximal direction.

With continued reference to FIG. 4, the rearward or proximal portion of the sidewall 44 connects to a closed end wall 46, and a forward or distal portion of the sidewall 44 defines a discharge neck 48 opposite the closed end wall 46. The closed end wall 46 may have a concave shape to facilitate the initiation of the inversion or rolling of the sidewall 44, enhance mechanical strength of the closed end wall 46, and/or to provide a receiving pocket to receive a distal end of drive member/piston 19. For example, the closed end wall 46 may define a receiving end pocket for interfacing directly with a similarly-shaped distal end of the drive member/piston 19. In some examples, at least a portion of the drive member/piston 19 may be shaped to substantially match the shape of the closed end wall 46 or, alternatively, pressure from the drive member/piston 19 as it is moved distally may conform the end wall 46 to substantially match the shape of at least a portion of the drive member/piston 19.

The end wall 46 may have a central portion 50 having a substantially dome-shaped structure and a drive member engagement portion 52 extending proximally from the central portion 50. The drive member engagement portion 52 is configured for releasably interacting with a corresponding engagement mechanism on the drive member/piston 19 of the fluid injector 10, for example as the drive member/piston is retracted. The rolling diaphragm syringe 34 may be made of any suitable medical-grade plastic or polymeric material, desirably a clear or substantially translucent plastic material. The material of the rolling diaphragm syringe 34 is desirably selected to meet the required tensile and planar stress requirements, water vapor transmission, and chemical/biological compatibility.

Figure 5:
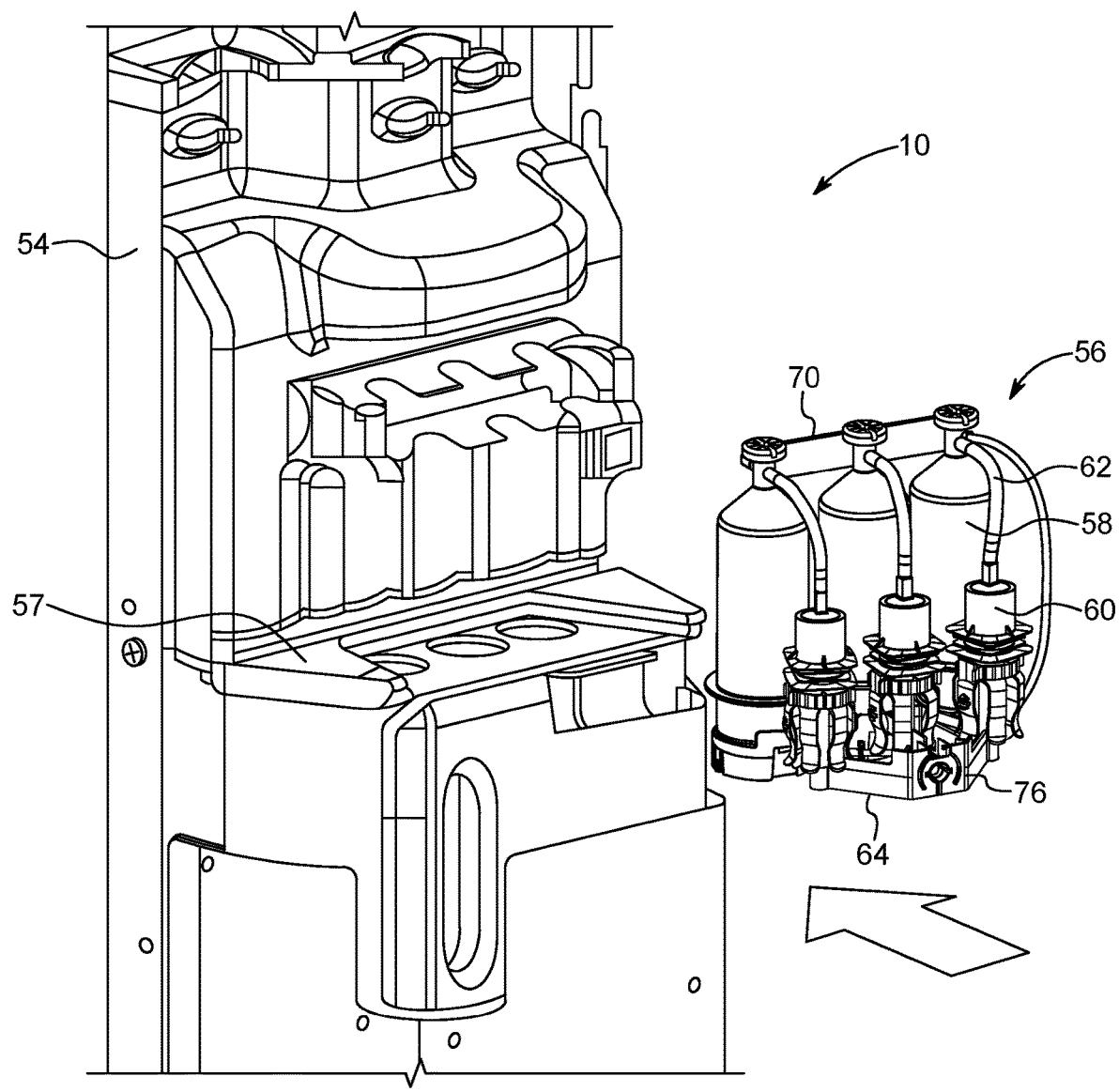
FIG. 5 is a perspective view of a fluid delivery system according to another example of the present disclosure.
Figure 6:
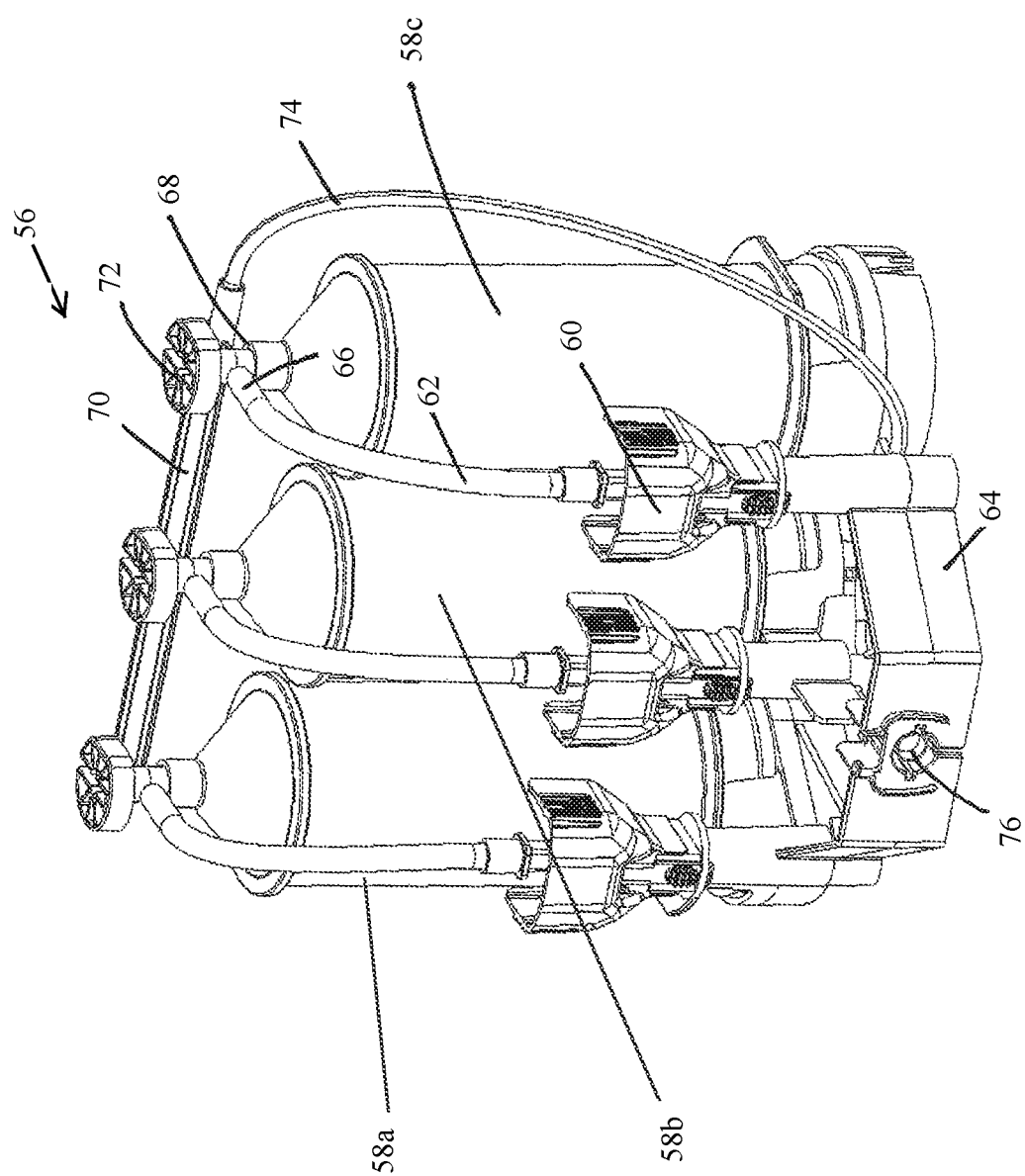
FIG. 6 is a front perspective view of a multi-use disposable system configured for use with the fluid delivery system of FIG. 5.
Figure 7:
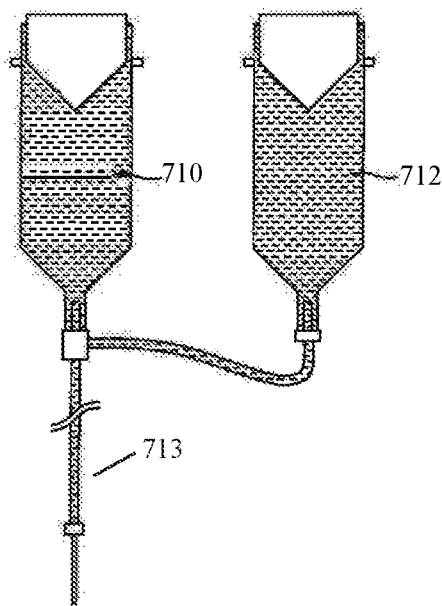
FIGS. 7-10 are schematic views depicting known methods of injecting a first fluid and a second fluid to a patient using a fluid injection system.
Figure 8:
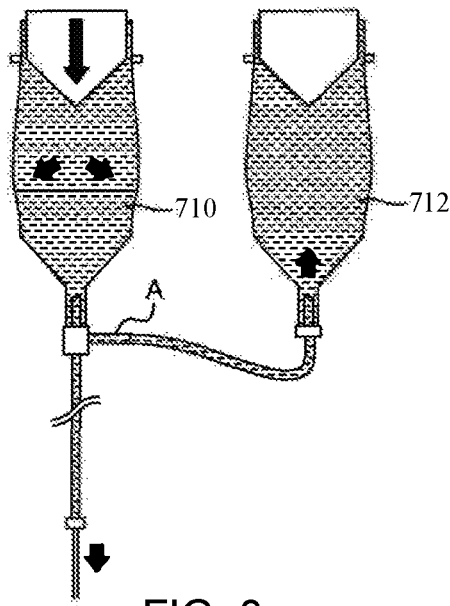
Figure 9:
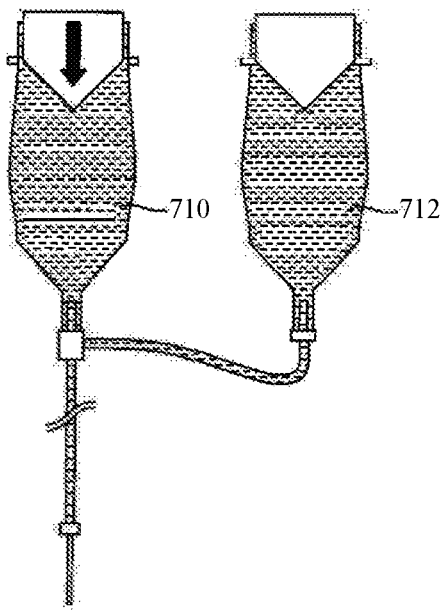
Figure 10:
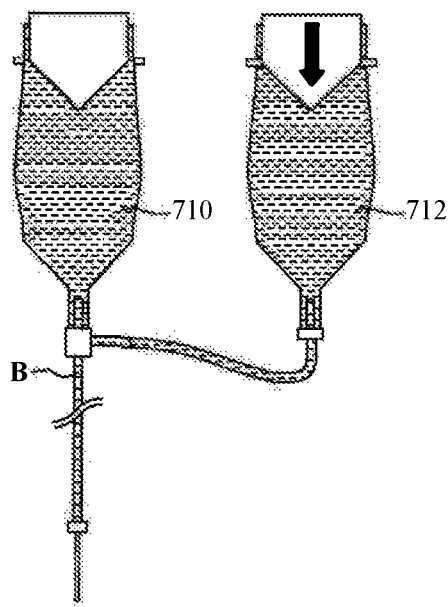

With reference to FIG. 5, a fluid injector 10 is shown in accordance with another example of the present disclosure. The injector 10 has a housing 54 that encloses various mechanical drive components, electrical and power components necessary to drive the mechanical drive components, and control components, such as electronic memory and electronic control devices used to control operation of reciprocally movable pistons (not shown). The fluid injector 10 further has a multi-patient (use) disposable system (MUDS) 56 that is removably connectable with the fluid injector 10. The MUDS 56 has one or more syringes or pumps 58. In some aspects, the number of syringes 58 corresponds to the number of pistons on the fluid injector 10. In some examples, such as shown in FIG. 6, the MUDS 56 has three syringes 58a-58c in a side-by-side arrangement. Each syringe 58a-58c has a bulk fluid connector 60 for connecting to a respective bulk fluid source (not shown) via a MUDS fluid path 62. The MUDS fluid path 62 may be formed as a flexible tube with a spike element at its terminal end that connects to the bulk fluid connector 60. Injector 10 and the corresponding MUDS 56 as illustrated in FIG. 5 are described in detail in WO 2016/112163, the disclosure of which is incorporated herein by this reference.

The MUDS 56 may comprise one or more syringes or pumps 58. In some aspects, the number of syringes 58 corresponds to the number of drive members/pistons on the fluid injector 10. In some examples, such as shown in FIGS. 5 and 6, the MUDS 56 has three syringes 58 arranged in a side-by-side arrangement. Each syringe 58 has a bulk fluid connector 60 for connecting to a respective bulk fluid source (not shown) via a MUDS fluid path 62. The MUDS fluid path 62 may be formed as a flexible tube that connects to the bulk fluid connector 60 having a spike element at its terminal end.

With reference to FIG. 6, the MUDS 56 has a frame 64 for supporting the one or more syringes 58a-58c. The syringes 58a-58c may be removably or non-removably connected to the frame 64. Each syringe 58a-58c has an elongated, substantially cylindrical syringe body. Each syringe 58a-58c has a filling port 66 in fluid communication with the MUDS fluid path 62 for filling the syringe 58a-58c with fluid from a bulk fluid source. Each syringe 58a-58c further has a discharge outlet or conduit 68 at the terminal portion of its distal end. The discharge outlet 68 of each syringe 58a-58c is in fluid communication with a manifold 70. A valve 72 is associated with each discharge outlet 68 and is operable between a filling position, where the filling port 66 is in fluid communication with the syringe interior while the discharge outlet 68 is in fluid isolation from the syringe interior, and a delivery position, where the discharge outlet 68 is in fluid communication with the syringe interior while the filling port 66 is in fluid isolation from the syringe interior. The manifold 70 has a fluid pathway that is in fluid communication with each syringe 58a-58c and with a fluid outlet line 74 in fluid communication with a port 76 configured for connecting to a single use fluid path element (not shown) for delivering fluid to the patient.

In various embodiments, for fluid injector 10 or any of the fluid injectors shown in FIGS. 1, 3, and 5, the motor 31 (FIG. 2) provides the motive force to reciprocally drive the drive member/piston 19 in a distal direction and discharges fluid within the syringes 12, 34 or MUDS 56. The motor 31 may have drive components, such as gears and shafts that are operatively connected to the drive member/piston 19 to reciprocally move the drive member/piston 19. Each motor 31 must be calibrated to correlate its operating characteristics, such as input current or output torque, to a flow rate or pressure and tolerances associated therewith. As described herein, calibration may be desirable to compensate for any variations or out of specification behavior from any of the different components of the fluid injectors 10, such as any variations in motor performance characteristics, particularly in fluid injectors with two or more syringes driven by two or more motors. For example, conversion of motor input torque for one motor 31 to an injector output pressure may be different for another motor 31. This variation may be further compounded by variations in tolerances of the drivetrain of the fluid injector 10. The accuracy of flow rate or pressure in a fluid injector 10 is directly correlative to a system and method used to calibrate the motor 31.

Figure 29:
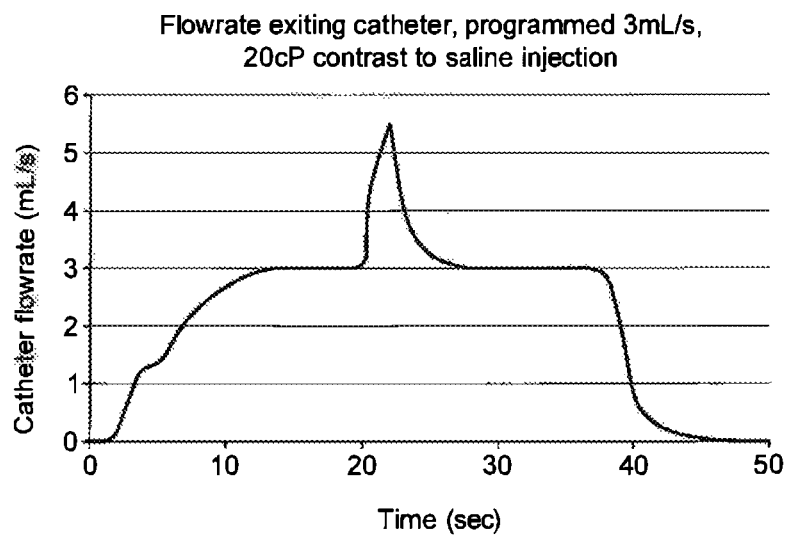
FIG. 29 is a graph depicting an overall flow rate of fluid exiting a catheter with a contrast agent to saline transition.
Figure 31:
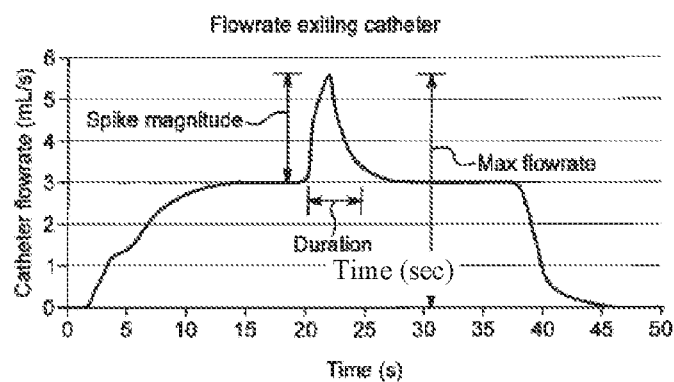
FIG. 31 is an annotated graph depicting an overall flow rate of fluid exiting a catheter with a contrast agent to saline transition.

As shown in FIGS. 29 and 31, when delivering contrast agent and, subsequently, saline solution to a patient's blood vessel, a spike or sudden increase in an overall flow rate of fluid exiting the catheter may be experienced during a flow transition between the contrast agent and the saline. In one example, an overall flow rate through the catheter is understood to be the combined flow rate of the first fluid (in one example, a saline solution, a contrast agent, or other diagnostic or therapeutic solution) and the second fluid (in one example, contrast agent, a saline solution, another diagnostic or therapeutic solution, or even the first fluid under different conditions, for example temperature or concentration, such that one of the relevant impedance related properties, for example viscosity, density, or compressibility, are different) exiting from the catheter. In one example, in which there is no flow of contrast agent through the catheter, the overall flow rate is equal to the flow rate of the saline solution. In another example, in which there is no flow of saline solution through the catheter, the overall flow rate is equal to the flow rate of the contrast agent. In another example, in which there is flow of saline solution and contrast agent through the catheter, the overall flow rate is equal to the combined flow rates of the saline solution and the contrast agent. Therefore, a fluid system may have a first flow rate corresponding to the flow rate of the first fluid, a second flow rate corresponding to the flow rate of the second fluid, and an overall flow rate corresponding to the combination of flow rates of the first and second fluids.

As shown in FIGS. 29 and 31, as the contrast agent is initially directed through the catheter, the overall flow rate of the system equals the flow rate of the contrast agent and gradually increases to a desired flow rate. In FIG. 31, in one example, the desired overall flow rate exiting the catheter is 3 mL/s. Once a sufficient volume of contrast agent has been directed through the catheter and into the patient's blood vessel, a volume of saline solution is subsequently directed through the catheter. As the delivery of contrast agent transitions to the delivery of saline solution from the catheter, a sudden spike or increase in the overall flow rate is experienced in the system. As shown in FIG. 31, this spike or increase in the overall flow rate has a certain duration and increases the overall flow rate of the system to a flow rate greater than the desired overall flow rate. As shown in this example, the overall flow rate may increase to 5.5 mL/s, which is 2.5 mL/s higher than the desired flow rate. Therefore, it is an object of the present disclosure to model, assess, predict, anticipate, compensate, control, and/or utilize an understanding of the multi-factorial system impedance and how it varies over time during the injection along with the related energy dissipation, storage, and changes thereof. Dampening the sudden spike or increase in the overall flow rate exiting the catheter by adjusting a flow profile of the saline solution and/or the flow profile of the contrast agent during a transition between the delivery of the contrast agent to the delivery of the saline solution may be achieved through one or more embodiments as set forth in this disclosure.

Figure 30:
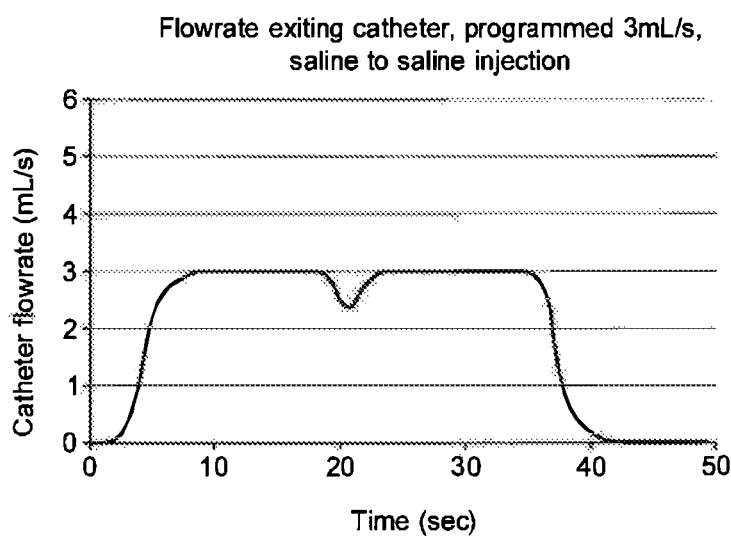
FIG. 30 is a graph depicting an overall flow rate of fluid exiting a catheter with a saline to saline transition.
Figure 32:
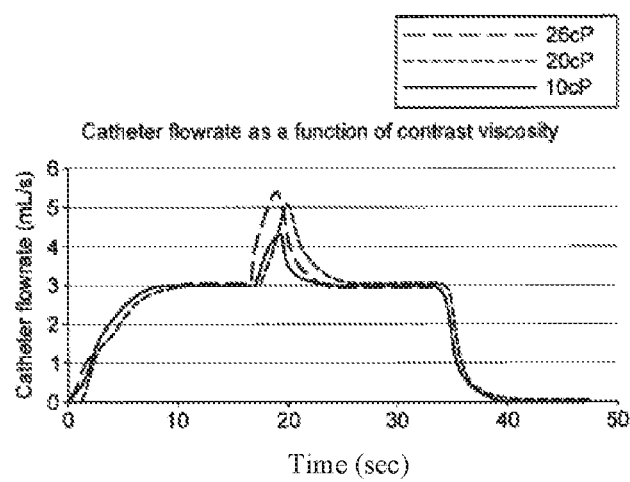
FIG. 32 is a graph depicting several different overall catheter flow rates of varying contrast agent viscosity.

As shown in FIG. 30, in a system that is delivering only saline solution to a patient via two discreet injection time periods or phases, there is no sudden spike or increase in the overall flow rate exiting the catheter. In fact, the system may experience a slight decrease in the overall flow rate between phases exiting the catheter, partially due to the inertia of the drive train which is another component of overall system impedance. As shown in FIG. 32, the viscosity of the contrast agent used in the system may also affect the severity of the sudden spike or increase in the overall flow rate exiting the catheter. For example, a contrast agent with a higher viscosity (e.g., 26 cP) may contribute to a larger spike or increase in the overall flow rate exiting from the catheter than a contrast agent with a lower viscosity (e.g., 10 cP).

Figure 33:
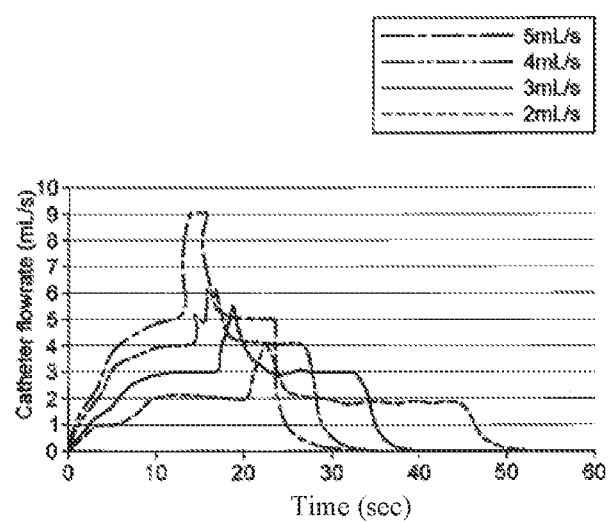
FIG. 33 is a graph depicting several different overall catheter flow rates.

As shown in FIG. 33, the desired overall flow rate of the fluid exiting from the catheter may also affect the severity of the sudden spike or increase in the overall flow rate exiting the catheter. For example, a higher desired overall flow rate (e.g., 5 mL/s) may contribute to a larger spike or increase in the overall flow rate exiting from the catheter than a lower desired overall flow rate (e.g., 2 mL/s). Thus it is not only the capacitance of the system that is a factor but the overall impedance including at least the capacitance and/or the resistance of the system. Resistance is dependent on time, volume, and flow as the viscosity of the fluids changes in the various fluid path elements.

Further, the fluid mixing ratio of contrast agent-to-saline may become inaccurate due to the stored fluid pressure energy in the lower pressure saline line. The contrast agent may be injected at a significantly higher ratio relative to saline, such as 80% contrast agent to 20% saline injection protocol. In small dosage injections at a high injection pressure, the effect may effectively stop the delivery of saline such that up to 100% contrast agent may be initially injected, rather than the desired 80% contrast agent to 20% saline ratio. Similar inaccuracies may occur at various other injection protocols, including, but not limited to 20% contrast agent to 80% saline ratio.

The above-described situation during powered injections at high contrast agent-to-saline ratio may occur at least in part due to injection system capacitance. Capacitance (also referred to as compliance or the ability to store a fluid volume and/or hydraulic energy) represents the ratio of the amount of suppressed fluid (i.e., backflow volume) that is captured in the swelling of the fluid injector system components or fluid path elements, such as the fluid lines and/or syringe(s), to the pressure in those components. Total system capacitance is inherent to each fluid injection system and to the various fluid path elements thereof, and depends on a plurality of factors, including injector construction, mechanical properties of materials used to construct the syringe, plunger, pressure jacket surrounding the syringe, fluid lines delivering the contrast agent and saline to a flow mixing device, size of the syringe, plunger, pressure jacket, etc. The amount of back or reverse flow increases when the relative speed difference between the two plungers is large, the simultaneous fluid flow is through a small restriction, the speed of the total fluid injection is large, and/or the viscosity of the fluid is high. The back or reverse flow can prevent or delay different ratios of simultaneously delivered fluid from occurring in certain injections, which can be a detriment for two-syringe fluid injector systems.

In general, the volume stored by capacitance is directly correlative to injection pressure and directly correlative to volume of contrast agent and saline in the syringes. For example, capacitance during an injection at 1200 psi with 150 ml of contrast agent and saline contained in the syringes is around 10 ml. In another example, the capacitance volume can be from about 5 ml to about 9 ml. The effect of capacitance is also a function of the ratio at which the first and second injection fluids, such as contrast agent and saline, are injected. At a 500/0-50% ratio, where contrast agent and saline are injected in equal amounts, backflow volume is minimized because the capacitance on the contrast agent side is equal to the capacitance on the saline side of the fluid injection system such that substantially equal pressures are present in each delivery line, for example with equal size syringes and fill volumes. Backflow may occur in situations where first and second injection fluids are delivered through long fluid conduits. However, as the injection ratio of contrast agent and saline changes, backflow volume increases corresponding to the increase in the ratio.

Figure 34:
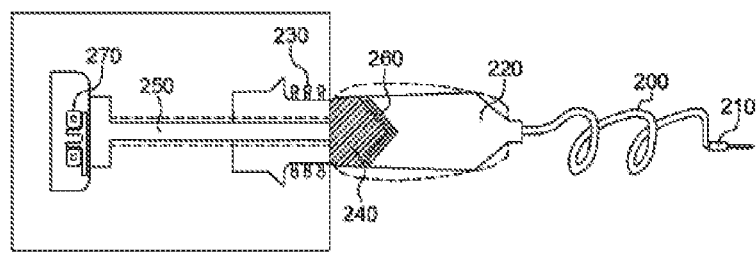
FIG. 34 is a schematic of a multi-fluid injection system according to an example of the present disclosure.

With reference to FIG. 34, capacitance in the system can occur in several different locations during an injection procedure of the system. In particular, in one example, the catheter tubing 200 of the system may experience swelling and/or compression during an injection procedure, which can affect the flow rates of the fluids through the tubing 200. In another example, the catheter 210 made of medical grade plastic or other compliant materials, may experience swelling and/or compression during an injection procedure, which can affect the flow rate of the fluid exiting the catheter 210. In another example, the syringe 220 of the injector system may experience swelling and/or compression during an injection procedure. The swelling of the syringe 220 as shown in dotted line in FIG. 34, may cause radial expansion and/or axial expansion of the syringe 220. In another example, the syringe interface 230 may experience swelling, stretch, and/or compression during an injection procedure. The syringe interface 230 is the connection between the syringe 220 and the injector system. In one example, the syringe interface 230 may include locking mechanisms, O-rings or other sealing members that can experience swelling, stretch, and/or compression during the injection procedure. In another example, a piston and/or plunger head 240 in the injector system may experience swelling and/or compression during an injection procedure. Due to the forces exerted by and on the piston head 240, compression forces may create swelling in the piston and/or plunger head 240. In another example, the piston 250 may experience swelling and/or compression during an injection procedure. Due to the forces exerted by and on the piston 250, compression forces may create swelling in the piston 250. In another example, in which a polymeric cover 260 is provided on the piston and/or plunger head 240, the polymeric cover 260 may experience swelling and/or compression during an injection procedure. In another example, a strain gauge cap 270 positioned in the injector system on an end of the piston 250 may experience swelling and/or compression during an injection procedure. Although the strain gauge cap 270 is configured to stretch to measure strain in the piston 250, the injection procedure may create additional swelling and/or compression in the strain gauge cap 270. One or more of these factors may contribute to the overall capacitance of the injector system. It is to be understood that, depending on the type of injection procedure, all of these factors may contribute to the overall capacitance of the injector system or only a few of these factors may significantly contribute to the overall capacitance of the injector system. In addition, various syringes and associated drive and mounting mechanisms may have similar or different impedance related components based on many factors, including for example syringe diameter and fill volume.

While several different factors that can affect the overall flow rate or an individual flow rate of one of the fluids in the injector system have been described, it is also contemplated that other factors may also affect these flow rates. The state of the particular flow of fluid through the injector system and the particular flow transition physics exiting from the catheter, such as the temperature of the contrast agent, may increase the viscosity of the contrast agent, and for cardiac CT and other advanced imaging applications the higher flow rates may also cause effects to these flow rates. For example, various system impedance components include electrical aspects such as capacitance, resistance and inductance; mechanical aspects such as elasticity (capacitance, compressibility and extensibility), friction or dissipation and inertia or momentum, fluid aspect such as pressure, heat, dissipation (viscosity and resistance to flow), momentum and inertia; and general aspects such as energy (potential energy, frictional losses and kinetic energy).

Solutions to the problem of reducing backflow due to system capacitance when delivering a high contrast agent-to-saline ratio and thereby reducing the likelihood of fluid flow rate spikes and delivering more accurate flow rates and mixing ratios of fluids are described herein below. In reference to FIG. 35 and all of the examples described below, a fluid flow profile of at least one of a first fluid 720 and a second fluid 722 is adjusted based on a function of the flow rate of one of the first fluid 720 and the second fluid 722 to minimize or dampen the spike or increase in the overall flow rate exiting from the catheter during a transition between delivering one of the first fluid 720 and the second fluid 722 to delivering the other of the first fluid 720 and the second fluid 722.

In one example, an increase to the stiffness of one or more of the components of the injector system can reduce swelling and/or compression in the components. In one example, using FIG. 34 for reference, the stiffness of one of the catheter tubing 200, the catheter 210, the syringe 220, the syringe interface 230, the piston head 240, the piston 250, the polymeric cover 260, and the strain gauge cap 270 may be increased to reduce swelling and/or compression in the components of the injector system. Such stiffness increases, which may be orders of magnitude different, or just slightly, depending on the component affected, may come by using stronger materials, thicker materials internal or external reinforcement materials, and/or other ways known to those skilled in the art. Overall system considerations such as usability and cost must be factored into any increase in stiffness, as for example, use of a pressure jacket around a syringe on the injector generally decreases workflow efficiency.

In another example which is disclosed in WO 2014/144651, which is incorporated herein by reference, a fluid path element such as a high crack pressure valve (not shown), may be placed at one or more places in the fluid path, for example at or after each syringe outlet but before the confluence or joining of the fluid flows, or on the common fluid path closer to the patient. The high crack pressure valve is a fluid path element with a non-linear impedance. The injection control mechanism 724 of FIG. 35 may for example move the piston and syringe plunger forward, monitor pressure and recognize and account for the phenomena that no volume is delivered until the proximal side exceeds the crack pressure of the high crack pressure valve. In another example, the fluid path element may be a flow restriction element (not shown). For example an orifice may be placed near the outlet of each syringe or at the confluence. The orifice may be fixed or may be variable, in which case it may be controlled by the controller 724. As the fluid moves through that restriction, the controller 724, can account for any change in impedance due to fluid impedance property differences and/or adjust the variable orifice.

Figure 11:
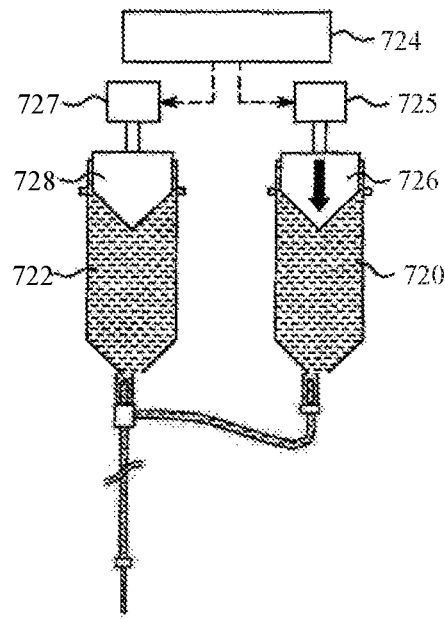
FIGS. 11 and 12 are schematic views depicting a fluid injection system according to one example of the present disclosure.
Figure 12:
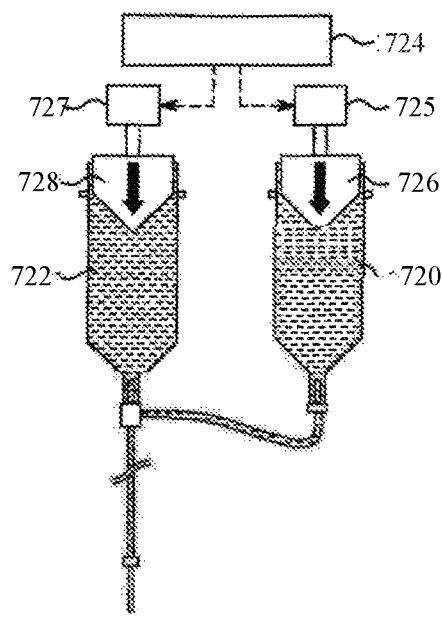

As shown in FIGS. 11 and 12, due to the additional time that is needed for the correct pressure to build-up in the less viscous first fluid 720, a method of reducing the likelihood of fluid flow rate spikes and delivering more accurate flow rates and mixing ratios includes delaying the application of pressure to the second fluid 722 until the pressure of the first fluid 720 has reached a predetermined pressure. This predetermined pressure may be a low equilibrium pressure that provides a smooth flow rate of fluid through the fluid injection system. In this example, the second fluid 722 may be more viscous than the first fluid 720. The second fluid 722 may be contrast agent and the first fluid 720 may be saline. As shown in FIG. 11, initially, pressure may be applied to the first fluid 720 via a plunger 726 until the pressure of the first fluid 720 has reached the predetermined pressure. As shown in FIG. 12, after the first fluid 720 has reached the predetermined pressure, the same predetermined pressure may be applied to the second fluid 722 via a plunger 728, resulting in the first fluid 720 and the second fluid 722 having a substantially similar flow rate through the fluid injection system. This system and method reduces the rapid increases in first fluid 720 pressure through the fluid injection system, which often causes erratic flow and inaccurate volumes of the first fluid 720 and the second fluid 722 being injected in the patient. By allowing the pressure of the first fluid 720 to reach a predetermined pressure before the second fluid 722, the first fluid 720 and the second fluid 722 can reach the same predetermined pressure at substantially the same time. The predetermined pressure will be dependent upon several factors, including, among others, the diameter of the tubing and catheter that is used to inject the first fluid 720 and the second fluid 722 into the patient, the viscosity of the first fluid 720 and the second fluid 722, the capacitance of the first fluid 720 and the second fluid 722 syringes, and/or the inner diameter of the tubing used to deliver the first fluid 720 and the second fluid 722 to the catheter.

It is also contemplated that this fluid injection system may be automated with the use of a controller 724 that controls the actuation of each of a pair of motors 725, 727 that are configured to move the pair of plungers 726, 728 that are used to apply pressure to the first fluid 720 and the second fluid 722. In this example, the controller 724 may be programmed to delay applying pressure to the second fluid 722 until the first fluid 720 has reached the predetermined pressure. The controller 724 may be a processor configured to store several different predetermined pressures for the fluid injection system depending on the procedure, catheter, the first fluid 720, the second fluid 722, tubing, and/or patient. In one example, a user of the fluid injection system may input this identifying information into the controller 724, which will calculate the proper predetermined pressure to apply to the first fluid 720 and the second fluid 722 utilizing the identifying information and/or stored information about at least the impedance related to the various system components.

Any system component, for example, a fluid path element, may have a record member associated with it that may contain identifying information regarding the associated system component. Such information may be used by the control system to reference the relevant impedance-related properties associated with that system element from a table or memory in the system or elsewhere. Alternatively or additionally, the record member may contain some or all of the relevant impedance-related properties, for example, for a tubing or catheter fluid path element it may contain the resistance with a fluid viscosity of 1 or the inner diameter and length from which the resistance thereof may be computed. The record member may be a bar code, a QR code, an RFID, machine-readable text, or another information conveying component known to those skilled in the art. Additional aspects are disclosed in U.S. Pat. No. 5,739,508, which is incorporated herein by reference in its entirety.

In an alternative example, the first fluid 720 may be more viscous than the second fluid 722. In this example, the process described above in reference to FIGS. 11 and 12, would be switched to apply an initial pressure to the second fluid 722 before applying pressure to the first fluid 720. It is also contemplated that the first fluid 720 and the second fluid 722 may have substantially equal viscosities. In this example, equal pressures may be applied to the first fluid 720 and the second fluid 722 at the outset of the process. The adjustments of relative pressures and plunger motions to prevent or reduce backflow, reduce the likelihood of fluid flow rate spikes and provide more accurate flow rates and mixing ratios of fluids may be repeated or happen essentially continuously during an injection. The adjustments may be determined before the injection or determined and/or adjusted during the injection. The determination may include sensor feedback commonly used in injectors such as pressure and position feedback as well as other sensors listed herein. In all cases, the user can be notified of adjustments through on-screen notices and/or through the recordation of the injection data by the electronic control device of the injector at the conclusion of the injection, such as through a report.

Figure 13:
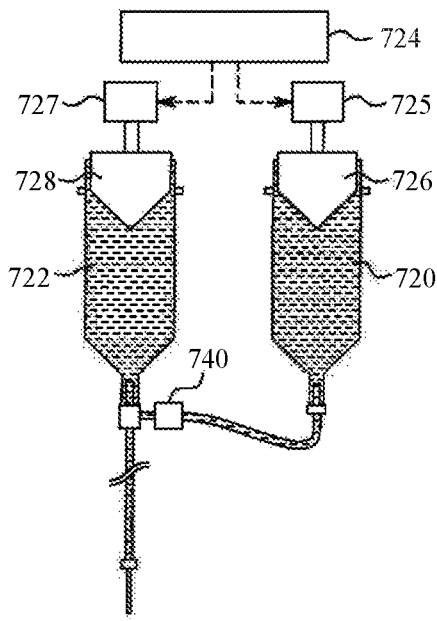
FIG. 13 is a schematic view depicting a fluid injection system according to another example of the present disclosure.

With reference to FIG. 13, another method for reducing the likelihood of fluid flow rate spikes and delivering more accurate flow rates and mixing ratios of fluids is described. A first fluid 720 and a second fluid 722 may be provided in a fluid injection system in which plungers 726, 728 driven by motors 725, 727 apply pressure to the first fluid 720 and the second fluid 722, respectively. In one example, the second fluid 722 may be more viscous than the first fluid 720. The second fluid 722 may be contrast agent and the first fluid 720 may be saline. A controller 724 may be operatively connected to the motors 725, 727 to control the rate of pressure applied to the first fluid 720 and the second fluid 722 by the plungers 726, 728. The controller 724 may be programmed to apply pressure to the first fluid 720 based on the pressure that is being applied to the second fluid 722. As the second fluid 722 is pushed through the fluid injection system, the controller 724 may correspondingly change the pressure applied to the first fluid 720 by the plunger 726. For example, if a certain pressure is being applied to the second fluid 722 by the plunger 728, the controller 724 may instruct the plunger 726 to apply a proportionally larger pressure to the first fluid 720 to compensate for the resistance of the more viscous second fluid 722. Using the controller 724 in this manner, the first fluid 720 and the second fluid 722 may flow through the fluid injection system at the desired ratio of flow rates, thereby minimizing any erratic flow in the fluid injection system. In another example, the first fluid 720 may be more viscous than the second fluid 722. In this example, the process described above in reference to FIG. 13, would be switched to apply a proportionally larger pressure to the second fluid 722 in comparison to the pressure applied to the first fluid 720. It is also contemplated that the first fluid 720 and the second fluid 722 may have substantially equal viscosities or the impedance of the two fluid paths from the plunger to the confluence or joining of the fluid flows is insignificant compared to other fluid path impedances. In this example, equal pressures may be applied to the first fluid 720 and the second fluid 722 at the outset. Commonly in an injection system, plunger 726 in FIG. 13 comprises or mates with a reusable piston which moves plunger 726 through the syringe to displace the fluid. The impedance characteristics of the combination, for example mechanical slop or gapping, elasticity, and structural deformation may be assessed and included in the overall impedance modeling and compensation discussed herein.

Figure 35:
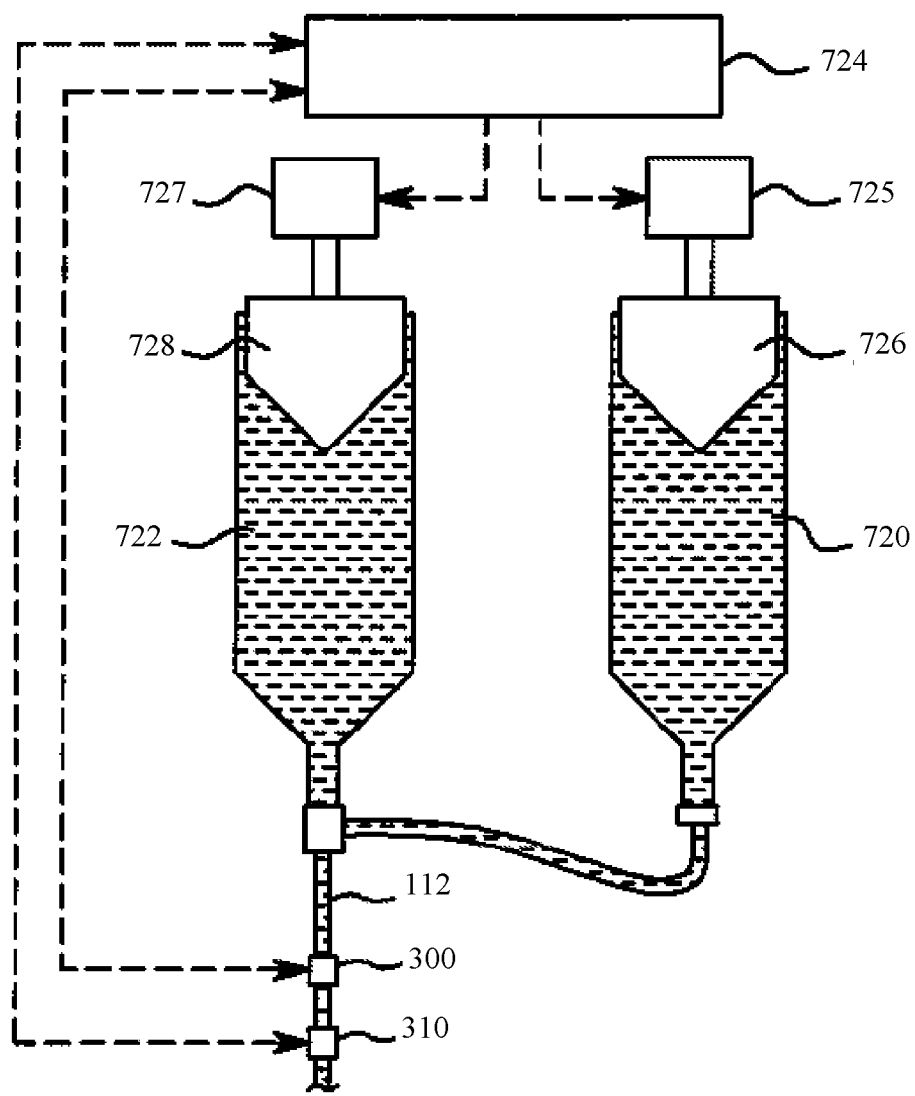
FIG. 35 is a schematic view depicting a fluid injection system according to another example of the present disclosure.

In another example, after pressure has been applied to the first fluid 720 and the second fluid 722, the flow rate of each fluid 720, 722 is measured. In the event the flow rates are not equal to one another, the fluid injection system may pause or hold the injection procedure to allow both fluids 720, 722 to achieve a steady-state pressure to reduce any stored energy in the fluid injection system. In one example, as the flow rates of the fluids 720, 722 are being measured, in the event it is determined that the flow rate of first fluid 720 is not equal to the flow rate of the second fluid 722 the fluid injection system can pause or hold the injection procedure while pressure is applied to either the first fluid 720 or the second fluid 722 to equalize the flow rates of the fluids 720, 722. In another example, the overall flow rate of the fluid exiting the catheter is measured during the injection procedure. The information regarding the overall flow rate is sent as feedback information to the controller 724 to permit the controller 724 to adjust the pressures applied to the first fluid 720 and/or second fluid 722 to equalize the flow rates through the fluid injection system to ensure a consistent overall flow of fluid is exiting from the catheter into the patient's blood vessel. As shown in FIG. 35, in one example, an ultrasonic or mass flow rate sensor 300 is used to measure the overall flow rate of at least one of the first fluid 720 and second fluid 722 through the system. It is contemplated that the sensor 300 can be placed at various positions within the system. It is also contemplated that more than one sensor 300 is used to measure the overall flow rate of at least one of the first fluid 720 and the second fluid 722 at different positions in the system. In one example, the sensor 300 is a sensor that clips onto the exterior of the fluid path set 112 to the catheter. It is contemplated, however, that other flow rate sensing technologies could be used and alternative mounting scenarios could be used to position the sensor 300 on the fluid path set 112. The sensor 300 provides a feedback loop to the controller 724 to control the injection parameters based on the overall flow rate measured by the sensor 300. This sensor 300 arrangement could also be used with peristaltic systems and other continuous flow systems. This sensor 300 may be used by the system to assess the accuracy of its system impedance model by comparing actual flows to anticipated flows, and thus allow it to update its system impedance model to accurately reflect and predict the future performance of the system. In another example, an air sensor 310 is provided in line with the sensor 300 to measure the air content in the fluid flowing through the fluid path set 112. The information measured by the air sensor 310 is another parameter for the controller 724 to control the injection parameters.

As further shown in FIG. 13, a check valve 740 may also be provided in the fluid injection system. The check valve 740 may be positioned in-line with the tubing of the first fluid 720. A check valve allows flow in one direction when the inlet pressure is greater than the outlet pressure. When the outlet pressure is greater than the inlet pressure, flow is blocked, up to the rupture pressure of the check valve. Using this check valve 740, the first fluid 720 will only flow into the second fluid 722 flow until a predetermined pressure is achieved by the first fluid 720. The predetermined pressure may be substantially equal to the desired flow rate pressure of the second fluid 722. The check valve 740 may be chosen based on the desired predetermined pressure. With the use of the check valve 740, neither fluid is permitted to flow back into the tubing of the first fluid 720, thereby reducing the expansion of the first fluid 720 syringe under the extra pressure.

Figure 14:
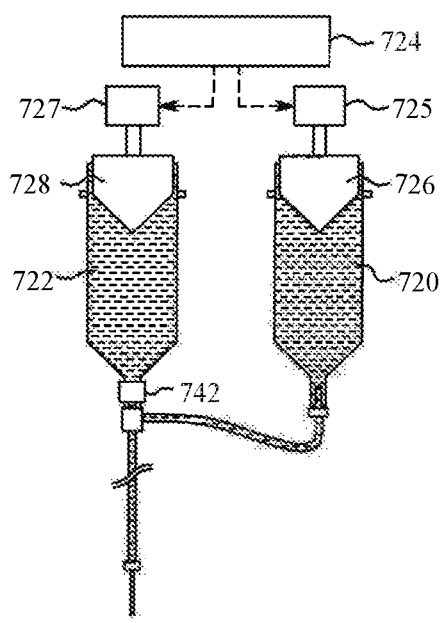
FIG. 14 is a schematic view depicting a fluid injection system according to another example of the present disclosure.

In a similar fashion, as shown in FIG. 14, a check valve 742 may be provided in-line with the tubing of the second fluid 722 portion of the fluid injection system. Similar to the check valve 740 on the first fluid 720 portion, the check valve 742 may be configured to control the flow of the second fluid 722 through the fluid injection system based on a desired predetermined pressure for the fluid injection system. The check valve 742 may be chosen according to the desired predetermined pressure. Using this system and method, the controller 724 may control the amount of pressure applied to the first fluid 720 and the second fluid 722 via the motors 725, 727 and plungers 726, 728. The controller 724 may monitor the pressures of the first fluid 720 and the second fluid 722 and adjust the plungers 726, 728 accordingly to maintain relatively equal pressures in the fluid injection system. Using the check valve 742 on the second fluid 722 portion of the fluid injection system, the peak pressure values in the fluid injection system can be significantly lowered. Using this arrangement, the pressure of the first fluid 720 can reach a predetermined pressure, while the check valve 742 does not release the second fluid 722 until the predetermined pressure is also achieved, thereby reducing the amount of second fluid 722 that backflows into the first fluid 720 portion of the fluid injection system. In one example, the first fluid 720 may be brought to the predetermined pressure and then the second fluid 722 may be subsequently pressurized to be released through the check valve 742. It is contemplated that the controller 724 can be programmed to initiate these pressurization procedures. In the example where the first fluid 720 is more viscous than the second fluid 722, the check valve 742 may be positioned in-line with the tubing of the first fluid 720 to prevent the first fluid 720 from opening the check valve 742 until a predetermined pressure has been applied to the first fluid 720.

Figure 15:
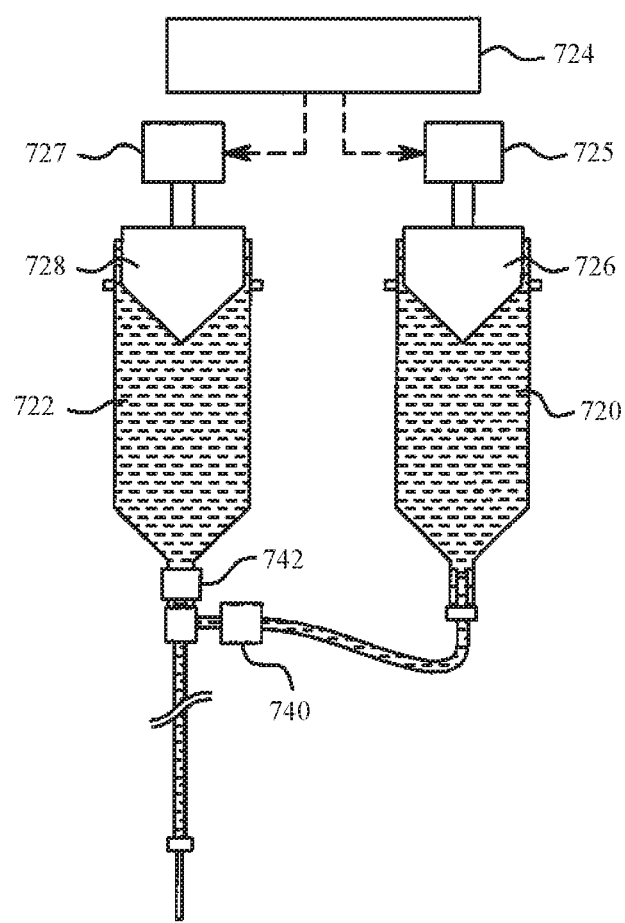
FIG. 15 is a schematic view depicting a fluid injection system according to another example of the present disclosure.

As shown in FIG. 15, it is also contemplated that the fluid injection system may include a check valve 740 on the first fluid 720 portion of the fluid injection system and a check valve 742 on the second fluid 722 portion of the fluid injection system. In this arrangement of the fluid injection system, fluid pressure from the non-active portion of the fluid injection system may be eliminated or isolated until the active portion of the fluid injection system reaches the same fluid pressure. For example, fluid pressure from the second fluid 722 may be eliminated or isolated in the fluid injection system until the fluid pressure of the first fluid 720 reaches a predetermined pressure or an equal pressure to the second fluid 722. The check valves 740, 742 may be chosen based on the desired predetermined pressure of the first fluid 720 and the second fluid 722. Using this arrangement, the first fluid 720 and the second fluid 722 are not mixed together in the fluid injection system until each fluid has reached the predetermined fluid pressure. A controller 724 may also be used in this arrangement to control the pair of motors 725, 727 that actuate the plungers 726, 728 that apply pressure to the first fluid 720 and the second fluid 722. The controller 724 may be pre-programmed with information regarding the threshold pressures for the check valves 740, 742 to coordinate the proper pressures applied by the plungers 726, 728 to the first fluid 720 and the second fluid 722. In another example, the check valves 740, 742 may be high crack pressure valves configured to reduce or essentially eliminate the backflow in the fluid injection system. The high crack pressure valves 740, 742 may be check valves that allow flow in only one direction. The high crack pressure valves 740, 742 may have a high opening or cracking pressure that may be fixed or settable to be above or near the maximum or expected operating pressure of the fluid injection system. One example of such a high cracking pressure valve may include a spool valve having an internal sliding element that can block fluid flow as discussed above. The valve may include a resistive force element, such as a spring or a pressurized bladder, to resist the movement of the sliding element. By providing the high crack pressure valves 740, 742 with a high cracking pressure, no fluid may continue to flow or dribble out of the two syringes into the fluid path and possibly the patient until the requisite pressure balance is achieved in the fluid injection system. Thus the capacitive component of the syringe impedance may be compensated for and/or addressed by the system. This compensation has been described in International Application Publication No. WO 2014/144651, which is incorporated herein by reference in its entirety. In another example, the open position of the check valves 740, 742 can be adjusted so that the check valves 740, 742 are partially open to control the flow of fluid through the check valves 740, 742. The check valves 740, 742 may be adjusted manually or automatically by the controller 724. Based on the flow rates of the first fluid 720 and/or the second fluid 722, the check valves 740, 742 can be partially opened, fully opened, or closed to achieve a desired flow rate of the fluid 720, 722 through the check valve 740, 742.

Figure 16:
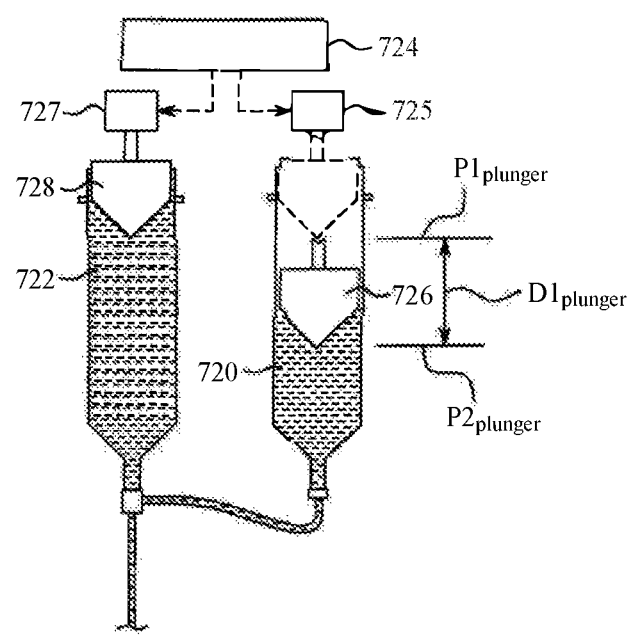
FIG. 16 is a schematic view depicting a fluid injection system according to another example of the present disclosure showing a plunger in an extended position.
Figure 17:
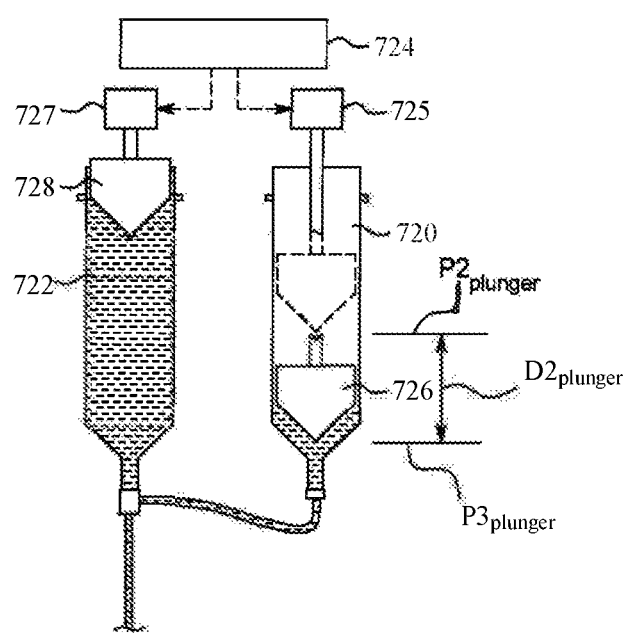
FIG. 17 is a schematic view depicting the fluid injection system of FIG. 16 with the plunger in an over-travel position.

As shown in FIGS. 16 and 17, another method of reducing the likelihood of fluid flow rate spikes and delivering more accurate flow rates and mixing ratios of fluids is through the use of an over-travel and fast-controlled reverse movement or pull of the plunger 726 within the first fluid 720 syringe to at least partially compensate for any undelivered first fluid 720 in the fluid injection system. In this arrangement, the second fluid 722 may be more viscous than the first fluid 720. The over-travel position and fast-controlled reverse movement or pull of plunger 726 result in the plunger resting at the originally intended stop position and may be calculated according to the system's understanding or model of the system impedances, for example, the amount of potential stored volume in the first fluid 720 syringe based on the desired fluid pressure and the plunger 726 position at the end of the first fluid 720 injection procedure. To determine the length of over-travel for the plunger 726 that is needed to receive the desired volume of the first fluid 720, the following equation is used to calculate the plunger 726 over-travel distance, as identified in U.S. Patent Application Publication No. 2010/0222768 to Spohn et al., which is hereby incorporated by reference in its entirety:

$$\text{Over-Travel (ml)} = C_1 + C_2 * x + C_3 * x^{-2} + C_4 * x^{-3} + C_5 * y + C_6 * y^{-2} + C_7 * y^{-3}$$

(Where: $C_1 = -0.811$; $C_2 = 0.039$; $C_3 = -0.00035$; $C_4 = 9.05\text{E}-7$; $C_5 = 0.0269$; $C_6 = -4.43\text{e}-5$; $C_7 = 2.607\text{e}-8$; x axis=pressure; y axis=position)

To receive the desired volume of the first fluid 720 from the fluid injection system, the plunger 726 must be over-traveled and then pulled back in reverse the same amount as the over-travel to compensate for the capacitance volume of the first fluid 720 syringe.

With reference to FIG. 16, upon activation of the controller 724, the motor 725 is activated to drive the plunger 726, which causes transition of the plunger 726 from a first initial position $P1_{plunger}$ (shown in dashed lines) to a second extended position $P2_{plunger}$, thereby advancing the plunger 726 a corresponding delivery distance $D1_{plunger}$. As the plunger 726 is transitioned across the delivery distance $D1_{plunger}$, a pre-set volume of the first fluid 720 is delivered from the interior of the first fluid 720 syringe to a downstream location. During delivery of the first fluid 720 from the interior of the syringe to the downstream location, the syringe swells in such a manner that it is radially displaced from its initial configuration. As the plunger 726 is advanced longitudinally within the syringe to dispel liquid from the interior of the syringe, the first fluid 720 imparts an axial force to the wall of the syringe.

As shown in FIG. 17, in order to account for the under-delivery of fluid from the interior of the syringe due to the swelling of the syringe, the plunger 726 can be programmed to over-travel a sufficient longitudinal distance to compensate for the expansion of the syringe. In order to over-travel a specified longitudinal distance, the motor 725 is actuated by the controller 724, which causes further transition of the plunger 726 from the second extended position $P2_{plunger}$ (shown in dashed lines) to a third over-travel position $P3_{plunger}$, thereby advancing the plunger 726 a corresponding delivery distance $D2_{plunger}$. As the plunger 726 is transitioned across the delivery distance $D2_{plunger}$, a predetermined volume of the first fluid 720 is delivered from the interior of the syringe to the downstream location to compensate for the under-delivery of fluid from the interior of the syringe as a result of the capacitance volume of the first fluid 720 syringe during transition from the first initial position to the second extended position.

Once forward longitudinal movement of the plunger 726 within the syringe is ceased, the plunger 726 may be rapidly driven back in order to compensate for the increased pressures within the fluid injection system resulting from the over-travel of the plunger 726. In order for the plunger 726 to retract to the retracted position, the controller 724 activates the motor 725, which causes transition of the plunger 726 from the third over-travel position $P3_{plunger}$ to the retracted position, thereby retracting the plunger 726 a corresponding retraction distance. This rapid backwards retraction of the plunger 726 relieves the swelling of the syringe and depressurizes the system. In one example, the rapid back-drive of the plunger 726 can be on the order of about 20 ml/s to 30 ml/s, for example 25 ml/s. This depressurization of the system allows the linear travel of the plunger 726 to coincide with the actual intended location, irrespective of capacitance volume. In the example where the first fluid 720 is more viscous than the second fluid 722, the process described above in reference to FIGS. 16 and 17 would be switched to apply an over-travel and fast-controlled reverse movement or pull of the plunger 728 within the second fluid 722 syringe to compensate for any undelivered second fluid 722 in the fluid injection system. It is also contemplated that the first fluid 720 and the second fluid 722 may have substantially equal viscosities. In this example, equal pressures may be applied to the first fluid 720 and the second fluid 722 at the outset of the process.

In typical fluid injection systems with saline and contrast agent fluids, the contrast agent has a higher viscosity than the saline. Due to this difference in viscosity, it is often difficult to apply the correct pressure to each fluid to achieve a uniform pressure between the two fluids to create a smooth flow of the mixture of the two fluids to the downstream location. As described herein, the higher viscosity of the contrast agent may cause backflow in the fluid injection system and/or swelling of the syringes holding the saline and/or contrast agent. Therefore, in one example of the present disclosure, as an example of modeling, modifying, adapting to and/or changing the system impedance, the saline used in the fluid injection system may be replaced with an alternative fluid that has similar properties to saline but has a higher viscosity to approximate the higher viscosity of the contrast agent. In one example, the saline may be replaced with a Ringers Lactate solution, which has a viscosity similar to blood or low viscosity contrast agents. The pressure required to deliver the Ringers Lactate solution through the fluid injection system is higher than saline, which leads to a smaller difference between the pressure to move the Ringers Lactate solution and that needed to move the more viscous contrast agent resulting in lower spikes or jumps in the flow rates of the two fluids. The Ringers Lactate solution will also have a higher density than saline, which will reduce the density exchange between the Ringers Lactate solution and the contrast agent.

In another example, the viscosity of the first fluid 720 or the second fluid 722 is adjusted to minimize or dampen the spike or increase in the overall flow rate during a transition between delivering one of the first fluid 720 and the second fluid 722 to delivering the other of the first fluid 720 and the second fluid 722. In one example, a volume of the first fluid 720 is added to the second fluid 722 to dilute the overall viscosity of the second fluid 722. Since the first fluid 720 has a lower viscosity, the first fluid 720 will dilute the second fluid 722 and reduce the overall viscosity of the second fluid 722. In another example, the viscosity of the first fluid 720 is increased to match the viscosity of the second fluid 722. By equalizing the viscosities of the fluids 720, 722, the transition of flow between the delivery of one of the first fluid 720 and the second fluid 722 and the delivery of the other of the first fluid 720 and the second fluid 722 does not create such a large spike or increase in the overall flow rate exiting from the catheter.

Figure 18:
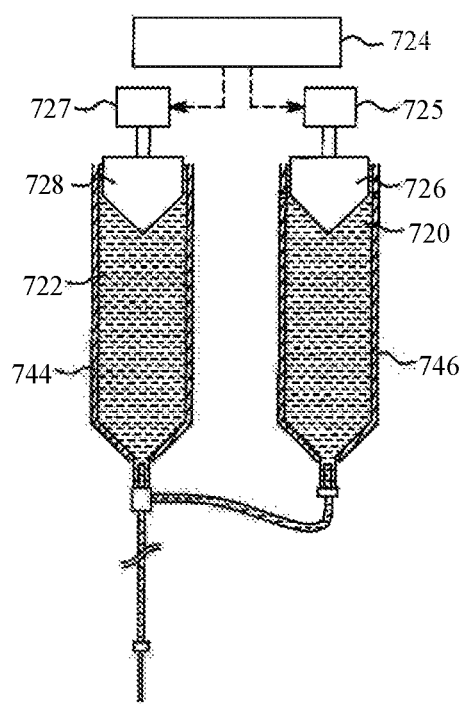
FIG. 18 is a schematic view depicting a fluid injection system according to another example of the present disclosure.

As shown in FIG. 18, in another example of this disclosure, as an example of modeling, modifying, adapting to and/or changing the system impedance, the second fluid 722 syringe may be designed with a lower capacitance (stored volume under pressure) than conventional syringes to reduce the effect of backflow into the second fluid 722 syringe. In this example, the first fluid 720 may be more viscous than the second fluid 722. In this example, a pressure jacket 744 may be provided around the outer surface of the second fluid 722 syringe to restrict the swelling in the second fluid 722 syringe due to backflow of second fluid 722. By providing the pressure jacket 744, the outer circumferential surface of the second fluid 722 syringe is reinforced, thereby limiting the amount of expansion or swelling in the second fluid 722 syringe. The pressure jacket 744 is configured to lower the capacitance of the second fluid 722 syringe, which results in a more accurate volume of the second fluid 722 being provided at the downstream location. The pressure jacket 744 may be made, for example, from a hard, medical-grade plastic or other materials as known to those of skill in the art, to provide the sufficient rigidity to the second fluid 722 syringe. It is also contemplated that an additional pressure jacket 746 may be provided around the outer circumferential surface of the first fluid 720 syringe to assist in also lowering the capacitance of the first fluid 720 syringe, thereby providing more accurate volumes of the first fluid 720 at the downstream location.

For the injector system to correctly model the impedance properties of the system, it may be desirable to include a mixing valve at the confluence or joining of the two (or more) fluids so that beyond that point, the fluids are well mixed and have a consistent set of impedance properties. Suitable mixing valves include those of Schriver, et al, in U.S. Pat. No. 9,555,379, Schriver, et al, WO 2014/179326, Reilly, et al, U.S. Pat. No. 8,162,903, Buder, et al., U.S. Pat. No. 9,861,752, and Yagi, et al. U.S. Pat. No. 9,314,749.

Figure 19:
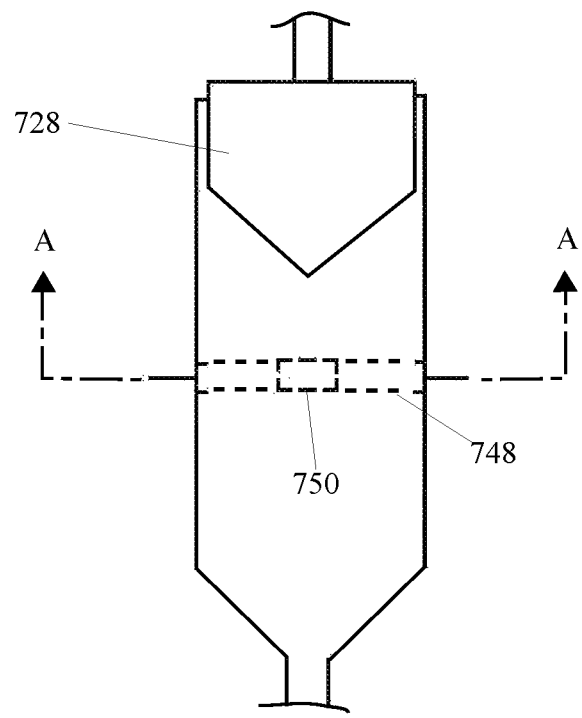
FIG. 19 is a front view of the syringe according to one example of the present disclosure.
Figure 20:
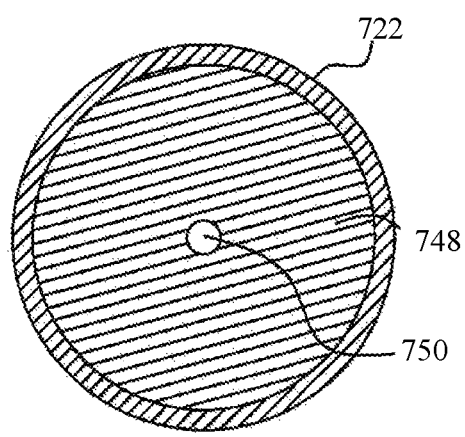
FIG. 20 is a cross-sectional view depicting a syringe of a fluid injection system according to the example in FIG. 19 along line A-A.
Figure 21:
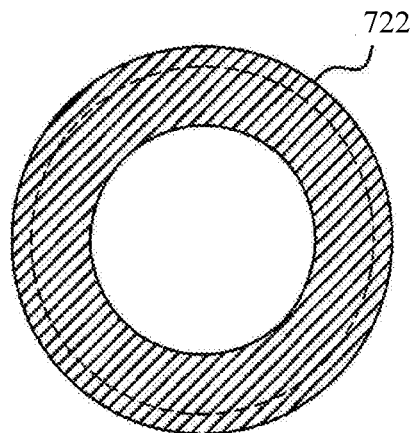
FIG. 21 is a cross-sectional view depicting a syringe of a fluid injection system according to another example of the present disclosure.

With reference to FIGS. 19-21, additional methods of modeling, modifying, adapting to and/or changing the system impedance, for example for reducing the likelihood of fluid flow rate spikes and delivering more accurate flow rates and mixing ratios of fluids are described. In FIGS. 19 and 20, an obstruction member 748 may be provided in the second fluid 722 syringe to increase the fluid pressure of the second fluid 722 through the second fluid 722 syringe. In this example, the first fluid 720 may be more viscous than the second fluid 722. In one example, the obstruction member 748 may include an opening 750 configured to increase the fluid pressure of the second fluid 722 based on the desired fluid pressure through the fluid injection system. In one example, the opening 750 may be circular. However, it is contemplated that alternative shapes for the opening may be used, along with additional openings in the obstruction member 748. The obstruction member 748 is configured to increase the fluid pressure of the second fluid 722 so the second fluid 722 tubing of the fluid injection system does not decompress during the fluid injection process. Further, the increased fluid pressure of the second fluid 722 will decrease the amount of backflow that is directed to the second fluid 722 syringe, which may expand or swell the second fluid 722 syringe. The increased pressure of the second fluid 722 may be substantially equal to the pressure of the first fluid 720. In the example where the second fluid 722 is more viscous than the first fluid 720, the obstruction member 748 may be provided in the first fluid 720 syringe to increase the fluid pressure of the first fluid 720 through the first fluid 720 syringe.

In another example of the disclosure the second fluid 722 syringe may include a reduced inner diameter. As shown in FIG. 21, the inner diameter of the second fluid 722 syringe has been reduced from a larger diameter (shown in dashed lines) to a smaller diameter to increase the fluid pressure of the second fluid 722 through the fluid injection system. The inner diameter of the second fluid 722 syringe may be reduced in only a portion of the second fluid 722 syringe or the inner diameter of the second fluid 722 syringe may be reduced along the entire length of the second fluid 722 syringe. Similar to the obstruction member 748 of FIGS. 19-20, the reduced inner diameter of the second fluid 722 syringe is configured to increase the fluid pressure of the second fluid 722 so the second fluid 722 tubing of the fluid injection system does not decompress during the fluid injection process. Further, the increased fluid pressure of the second fluid 722 will decrease the amount of backflow that is directed to the second fluid 722 syringe, which may result in the expansion or swelling of the second fluid 722 syringe. The reduced inner diameter will also assist in bringing the pressure of the second fluid 722 to a substantially equal pressure as the first fluid 720. In the example where the second fluid 722 is more viscous than the first fluid 720, the inner diameter of the first fluid 720 syringe may be reduced to create a similar obstruction.

Figure 22:
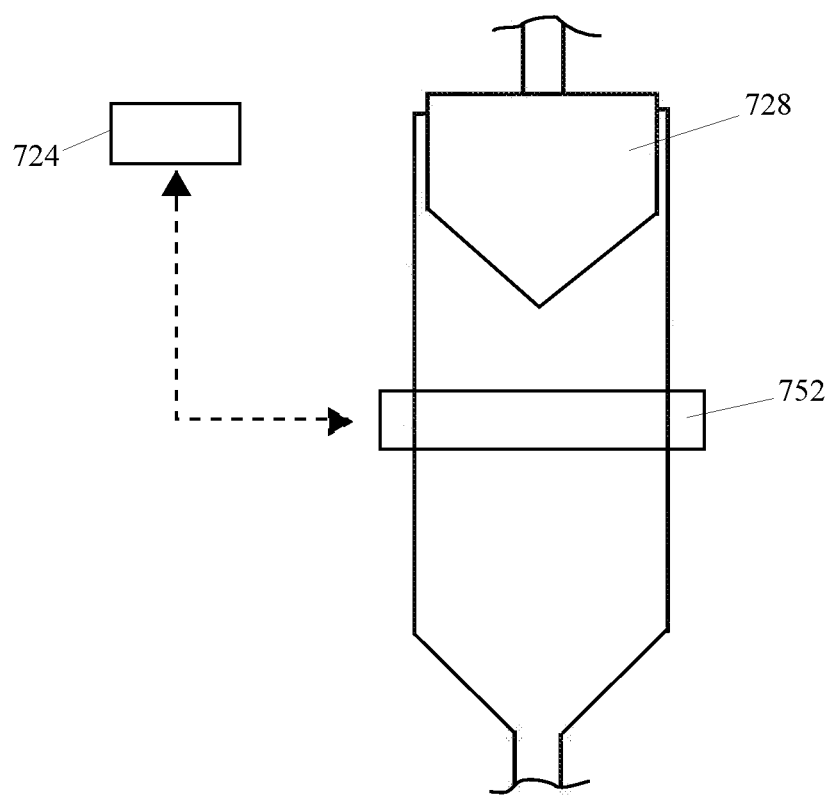
FIG. 22 is a schematic view depicting a fluid injection system according to another example of the present disclosure.

With reference to FIG. 22, another method of modeling, modifying, adapting to and/or changing the system impedance is described. In this example, the first fluid 720 may be more viscous than the second fluid 722. In this example, an external restriction member 752 may be provided around a portion of the outer circumferential surface of the second fluid 722 syringe. The external restriction member 752 may be cylindrical in shape. However, it is contemplated that alternative shapes and sizes may be used with the second fluid 722 syringe. The external restriction member 752 may define an aperture through which the second fluid 722 syringe may be inserted. The external restriction member 752 may be provided via a friction-fit on the second fluid 722 syringe to control the flow rate of the second fluid 722 through the second fluid 722 syringe. The external restriction member 752 may reduce the swelling or expansion of the second fluid 722 syringe due to any backflow into the second fluid 722 syringe, thereby reducing the capacitance of the second fluid 722 syringe. The external restriction member 752 may apply pressure to the outer surface of the second fluid 722 syringe, thereby restricting the flow of the second fluid 722 through the second fluid 722 syringe. Pressure may be applied by the external restriction member 752 by decreasing the diameter of the aperture defined by the external restriction member 752. It is also contemplated that the pressure applied by the external restriction member 752 may be controlled by the controller 724. The controller 724 may be programmed to adjust the pressure applied by the external restriction member 752 and the diameter size of the aperture defined by the external restriction member 752 based on the fluid pressures in the fluid injection system, the capacitance of the second fluid 722 syringe and the first fluid 720 syringe, the catheter size, and the viscosities of the second fluid 722 and the first fluid 720, among other factors. The controller 724 may also be programmed to adjust the diameter size of the aperture defined by the external restriction member 752 based on the timing of the fluid injection procedure. In the example where the second fluid 722 is more viscous than the first fluid 720, the external restriction member 752 may be provided around a portion of the outer circumferential surface of the first fluid 720 syringe.

Figure 23:
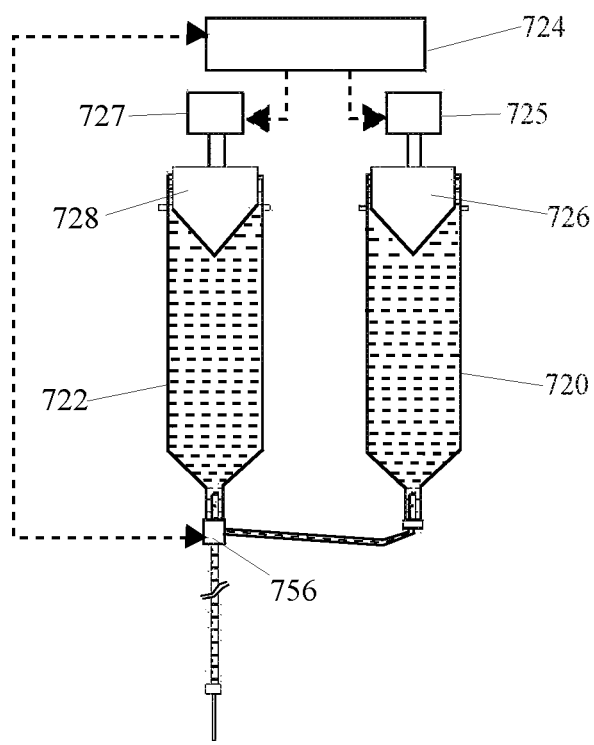
FIG. 23 is a schematic view depicting a fluid injection system according to another example of the present disclosure.

With reference to FIG. 23, another method of modeling, modifying, adapting to and/or changing the system impedance is described. In this example, the second fluid 722 may be more viscous than the first fluid 730. This method includes the use of an equalizing flow valve 756 to monitor and control the flow rates of the first fluid 720 and the second fluid 722. The equalizing flow valve 756 may be positioned in the fluid injection system at a location where the first fluid 720 tubing and the second fluid 722 tubing connect with one another. The equalizing flow valve 756 may monitor the flow rates of the first fluid 720 and the second fluid 722 and adjust an orifice defined by the equalizing flow valve 756 to maintain the desired delivery flow rates of the two fluids. In one example, the equalizing flow valve 756 may be connected to a controller 724, which also actuates the motors 725, 727 that drive the plungers 726, 728 in the fluid injection system. Using the controller 724 with the equalizing flow valve 756, the pressure applied by the plungers 726, 728 can be adjusted according to the flow rates of the two fluids through the equalizing flow valve 756. The controller 724 may be programmed to read the flow rates of the two fluids through the equalizing flow valve 756 and adjust the pressure applied by the plungers 726, 728 accordingly to ensure that the second fluid 722 and the first fluid 720 have substantially equal pressures. Alternatively, the controller 724 and/or equalizing flow valve 756 may be pre-programmed according to the impedance characteristics of the system including for example, the types of fluids used in the fluid injection system, the catheter size, the capacitance of the fluid injection system, and/or the desired flow rates of the two fluids, which information may be stored in the controller 724. An operator may manually input some or all of the information regarding the fluid injection system into the controller 724, which will assist in adjusting the plunger 726, 728 pressure and/or the equalizing flow valve 756 accordingly to obtain the desired flow rates of the two fluids. The system may have prior knowledge of or be able to determine the remainder or all of the other information used to assess the system impedance as in other embodiments disclosed herein.

In a similar method, a test injection procedure may be conducted using the first fluid 720 and second fluid 722 is performed before the actual diagnostic phase using the same flow rates as will be used from the diagnostic injection procedure. A pressure measurement of the first fluid 720 phase is obtained during the test injection procedure, which gives an indication of the expected pressure for the programmed flow rate under the current tubing and patient conditions. This measured pressure value is recorded and used during the diagnostic injection procedure to modify the flow rate of at least one of the first fluid 720 and the second fluid 722 to modify the flow rate and fluid flow profile of at least one of the first fluid 720 and the second fluid 722 to compensate for capacitance in the injector system. In one example, the flow rate modification is achieved by temporarily changing a pressure limit of one of the fluids 720, 722 in an adaptive flow algorithm used by a controller 724 to control the pressures of the fluid injection system.

Figure 24:
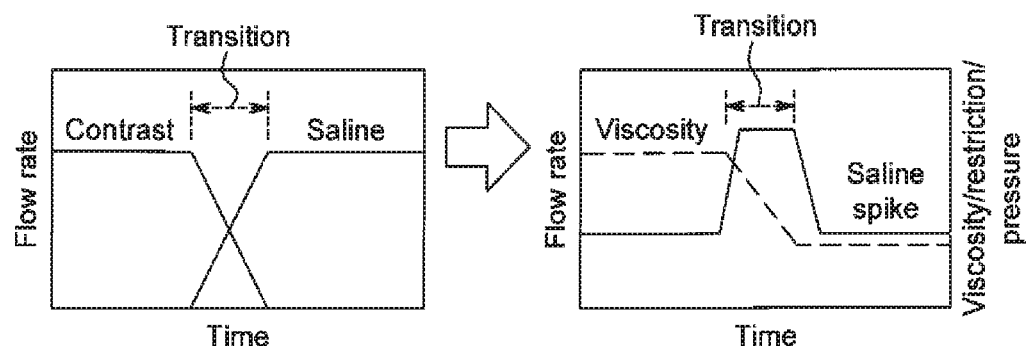
FIG. 24 is a graphical illustration of a transition period between injecting contrast agent and injecting saline during current multi-fluid injection procedures.
Figure 25:
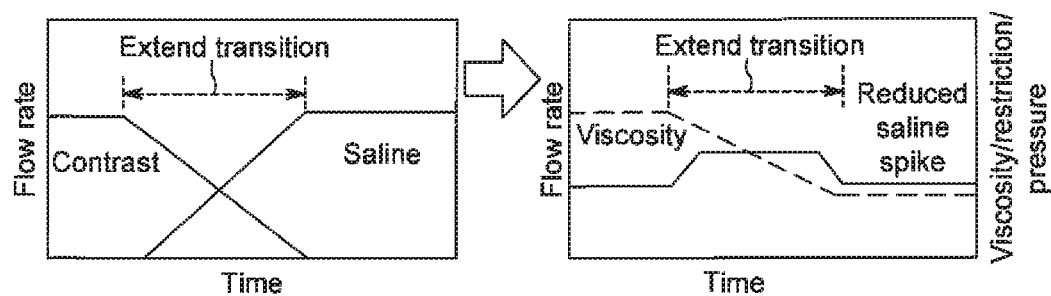
FIG. 25 is a graphical illustration of an extended transition period between injecting contrast agent and injecting saline according to the present disclosure.

With reference to FIGS. 24 and 25, another method of modeling, modifying, adapting to and/or changing the system impedance, for providing more accurate mixing ratios is described. During current multi-fluid injection procedures, a spike in saline flow rate may occur when the fluid passing through the catheter suddenly changes in viscosity, resulting in a drop in the resistance at the restriction point of the catheter. During this period of resistance drop, any fluid stored in the compliance of a disposable set holding the fluid is released through the catheter. As shown in FIG. 24, contrast agent is initially directed through the catheter. After the contrast agent has been injected, the saline is injected and begins to flow through the catheter. A transition period occurs when the flow rate of the contrast agent begins to decrease through the catheter and the flow rate of the saline begins to increase through the catheter. During this transition period, the viscosity of the fluid flowing through the catheter suddenly and quickly changes, which results in a spike of saline through the catheter. Due to the short transition period that occurs during the switch between injecting the contrast agent and injecting the saline, an increased drop in pressure is created, which causes an increased saline spike in the catheter.

As shown in FIG. 25, by extending the transition period between injecting the contrast agent and injecting the saline, a more gradual viscosity/pressure gradient is achieved during the injection procedure. With this extended transition period, the flow rate of the contrast agent is gradually and slowly reduced, while the flow rate of saline is gradually and slowly increased. The change in viscosity of the fluid through the catheter is more gradual, resulting in a decreased change in impedance of the fluid in the catheter. The extended transition period may be achieved in such a manner that does not significantly increase the volume of contrast agent that is delivered during the injection procedure and does not degrade the efficacy of the injection procedure. It is also contemplated that non-linear or non-continuous extended transition periods could be used, which would result in even less impact to the image taken of the patient, while incorporating aspects of the fluid dynamics of the injection system as described herein.

According to one example of the present disclosure, the fluid injector 10 discussed above with respect to FIGS. 1-2 is configured to a multi-phase injection of fluid in at least one syringe 12 utilizing a variable pressure limit during the transition from the first phase of the multi-phase/multi-fluid injection to the second phase of the injection. According to one particular example, the first phase constitutes an injection of contrast agent to the patient, and the second phase constitutes an injection of saline solution to the patient. The viscosity of the second phase of saline solution is typically less than the viscosity of the first phase of contrast agent, which may result in large fluctuations of flow rates at the transition from contrast flow to saline flow at the catheter tip. The variable pressure limit on the multi-phase injection is implemented by the fluid injector 10 during at least the transition between the phases to lessen the effects of the changing viscosity between the first and second phases on the flow rate of the fluid at the catheter tip during the injection by lowering the pressure limit of the second less-viscous phase. The implementation of the variable or changed pressure limit also lessens the pressure built up in the fluid path set 17 as the less-viscous second phase of the fluid pushes the more-viscous first phase of the fluid out of the fluid path set 17. This method serves to avoid or reduce the effects of a build-up of pressure of the less-viscous second phase fluid as the second phase fluid flushes the more-viscous first phase fluid from the fluid path set 17 and the catheter. The build-up of pressure of the second phase corresponds with an increase in the flow rate of the second phase fluid at the catheter as the last of the first phase fluid is expelled from the catheter.

Figure 26:
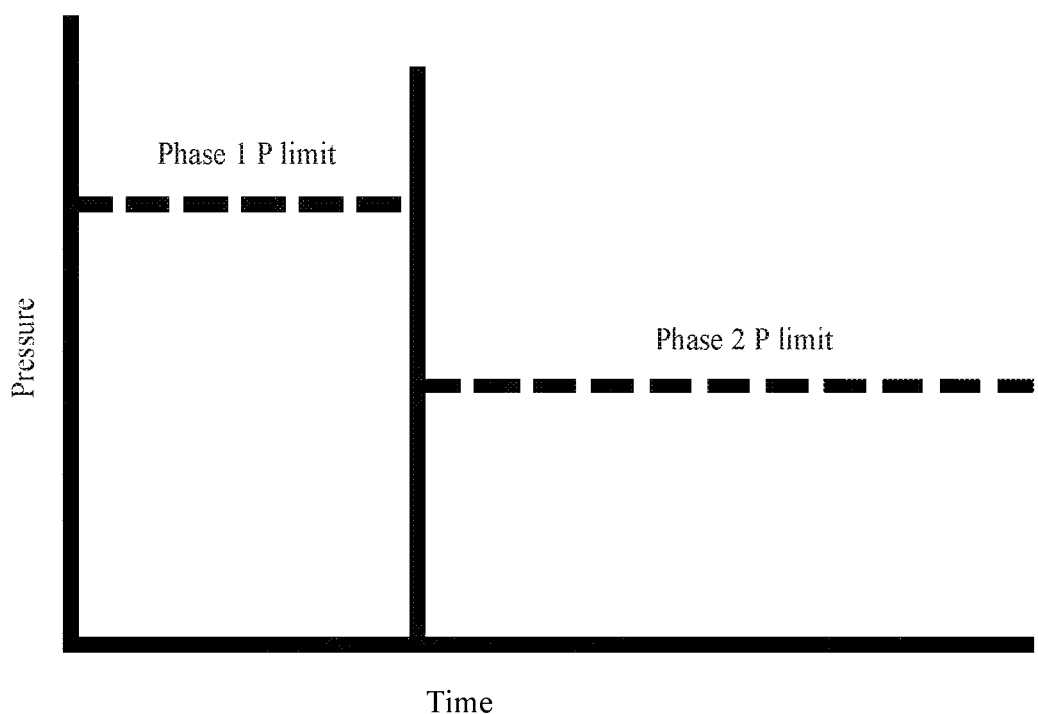
FIG. 26 is a graph depicting a variable pressure limit over time for an injection according to one embodiment of the present disclosure.

The variable pressure limit during the multi-phase injection of the fluid may be imposed by the electronic control devices responsible for controlling the movement of the piston 19 within syringes 12a,b to dispense the fluid from syringes 12a,b. As discussed above, the movement of the piston 19 may be controlled via actuation of the motor 31 responsible for moving the piston 19 within the syringe 12. As shown in FIG. 26, in accordance with an example of the present disclosure, the electronic control devices operate the motor 31 to move the piston 19 such that the first phase of the injection is performed with a first pressure limit. The first pressure limit, commonly the safety pressure limit, is usually not achieved or reached. At the transition between the first and second phases of the injection, the electronic control devices operate the motor 31 to move the piston 19 such that the second phase of the injection is performed with a second pressure limit. For example (as shown in FIG. 26), if the second fluid is less viscous than the first fluid, the first pressure limit is greater than the second pressure limit.

According to a particular example of the present disclosure, the electronic control devices are configured to derive the second pressure limit from at least one of a table or equation based upon various parameters of the fluids, injector, and disposables such as catheters, tubing or other items that may restrict the flow of fluid. Inputs to this table/equation include but are not limited to the types of fluids, fluid viscosities, fluid temperature, the configuration of fluid path elements of certain properties (for example lengths, diameters, compliances, etc. as is known in the art), catheter gauge, a desired flow rate (either from a user-input or predetermined from a protocol), capacitances and impedances of the system, and the position of the piston 19 in the syringe 12.

According to another example of the present disclosure, the electronic control devices are configured to apply the second pressure limit during injection of an initial amount of the second fluid and to apply the first pressure limit during injection of a remaining amount of the second fluid. As such, the altered second pressure limit can either be restored to the first pressure limit after a set volume of the second fluid is injected or remain in place for the duration of the less-viscous second phase.

In a further modification to the present example, the electronic control device can derive a third pressure limit based on the same parameters set forth above. The third pressure limit would be different from the first and second pressure limit in the above example. The control device is configured to apply the second pressure limit during injection of an initial amount of the second fluid during the second phase of the multi-phase injection and to apply the third pressure limit during injection of a remaining amount of the second fluid.

According to another example of the present disclosure, the second pressure limit may be set according to the following Equation (A):

$$\text{Pressure of second phase (psi)} = 13.07 \times FR + 18.8 \quad \text{Equation (A):}$$

Figure 27:
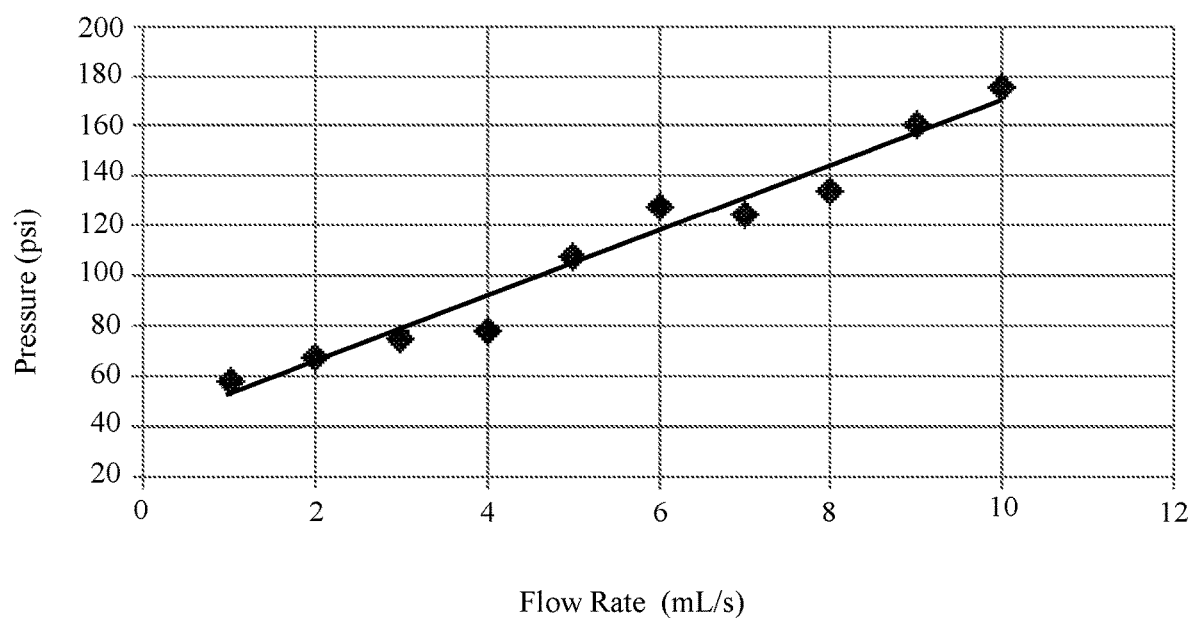
FIG. 27 is a graph depicting a comparison of flow rate and pressure characteristics for an injection according to one embodiment of the present disclosure.

FR is the flow rate as measured in mL/s. With reference to FIG. 27, the coefficients of Equation (A) for this particular fluid injection system were determined by measuring the maximum pressure within the fluid injector 10 at a series of different flow rates with a specific impedance based upon a specific set of circumstances including contrast and a fluid path configuration including a given catheter. As shown in FIG. 27, a plot of the maximum measured pressures versus the corresponding flow rates shows a generally linear relationship between flow rate and maximum measured pressure. A regression analysis of the determined linear relationship produced the coefficients identified in Equation (A). It is to be appreciated that the coefficients of Equation (A) are entirely exemplary and are determined based on a particular set of measurements taken for a particular fluid injector under a particular set of measurement circumstances. Different fluid injectors and different circumstances may yield different measurement results, which will result in different coefficients being determined for Equation (A) or for other equations representing flow rate as a function of pressure. Also, it is to be appreciated that Equation (A) may not necessarily be a linear equation as in the present example. The preferred equations may be built or collected from specific testing, theoretical analysis, and/or computations of impedances and the resulting operations over time. Variations in equipment should be accounted for given the operating parameters set forth herein.

According to certain embodiments, an extra 10 psi of pressure may be added to the second phase pressure result of Equation (A) to prevent premature pressure limiting. A lower limit to the flow rate of Equation (A) may also be added to prevent motor speed from falling below a given percentage of the set speed for the set injection flow rate to avoid a reduction in flow rate, particularly for higher concentrations or viscosities of the first phase of the fluid F. In the below example, 40% of the set speed for the injection flow rate was used. The flow rate set for the injection may also be adjusted based on the determined second pressure limit. The second syringe 12b containing the second fluid may also be pre-pressurized to a value ranging from 0 to 100% when implementing this method. In all cases, the user can be notified of the changes to a pressure limit or flow rate through on-screen notices and/or through the recordation of the injection data by the electronic control device of the injector at the conclusion of the injection, such as through a report.

Figure 28A:
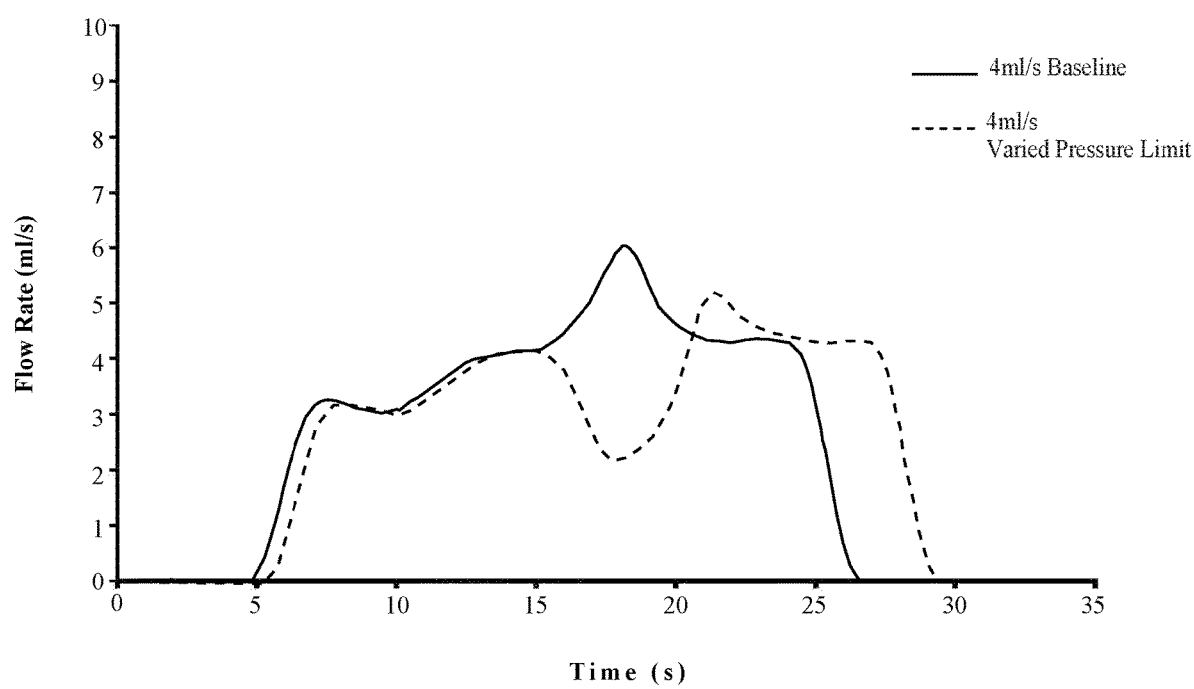
FIG. 28A is a graph depicting flow rate over time when variable pressure limits are utilized during an injection according to one embodiment of the present disclosure.

FIG. 28A illustrates the effect of implementation of the variable pressure limit, according to one example of the present disclosure, on flow rate during the transition from the first phase (from 0 to 15 seconds) to the second phase (from 15 to 30 seconds). As exhibited by the solid line in FIG. 28A, without variable pressure limiting according to the present disclosure, a significant increase or spike in the flow rate at the catheter is observed during the transition from the first phase to the second phase. As exhibited by the dashed line in FIG. 28A, implementation of the variable pressure limit according to an example eliminates the sharp increase in flow rate at the transition from the first phase to the second phase.

A control method according to one embodiment had a pressure limit on the saline phase of the injection. The process was performed using a Medrad® Salient™ fluid injector. The pressure limit used for each flow rate in the example was per the following equation:

$$\text{Pressure (psi)} = 13.07 \times FR + 8.8$$

$$FR = \text{Flow Rate}\left(\frac{\text{mL}}{s}\right)$$

On implementation, an extra 10 psi was added to that equation to prevent premature pressure limiting. The pressure limiting control method completely prevented the flow surge from occurring. Instead however, for higher concentrations of contrast, a decrease in flow rate was experienced. Therefore a lower limit to the flow rate was added to prevent motor speed from falling below 40 of the set speed for the set injection flow rate.

The following table below contrasts the original flow surge data to the controlled surge data. Note that the contrast flow rate, as stated in section 6.2, is lower than the set flow rate. The flow rate for comparisons is 5 mL/s:

TABLE 1

| Control Method | Contrast Equivalent | Flow Surge Rate (mL/s) | Change in Flow (mL/s) |
| --- | --- | --- | --- |
| No Control | Iopromide 370 at 31° C. | 6.8 | +1.8 |
| Single Decrement Flow | | 6.0 | +1.0 |
| Delta Flow[1] | | 5.6 | +0.6 |
| Pressure Limit (no speed limit) | | 3.8 | −1.2 |
| Pressure Limit (>40% speed limit) | | 3.6 | −1.4 |
| Pressure Limit (no speed limit) | Iopromide 370 at 25° C. | 1.1 | −3.9 |
| Pressure Limit (>40% speed limit) | Iomeprol 400 at 31° C. | 3.3 | −1.7 |

[1]Flow rate oscillates from adjustments

In an alternative embodiment, the pressure may be permitted to change, drop, or decrease more gradually than an abrupt change at the transition of one phase to another. For example, a gradual transition in the pressure limit may be generally linear or curvilinear and take place over one or more seconds. For example, information based on the characteristics of the fluid path, could indicate that the volume of the tubing from the syringe tip to the catheter is 10 ml. With a given flow rate of 5 ml/s, it may be estimated that the initial saline flow will reach the catheter in 1 second (peak or center flow rate moves at twice the average flow rate in laminar flow situations). Thus the decrease in pressure may be programmed to happen over approximately 1, 2, or optionally 3 seconds. This gradual pressure limit transition may reduce the drop in flow rate before the fluid viscosity transition happens and also reduce the peak flow rate after the transition and change in fluid viscosities. As with the other embodiments in this disclosure, the user can be notified of changes to the pressure or flow rate through on-screen notices and/or through the recordation of the injection data by the electronic control device of the injector at the conclusion of the injection, such as with a report.

Figure 28B:
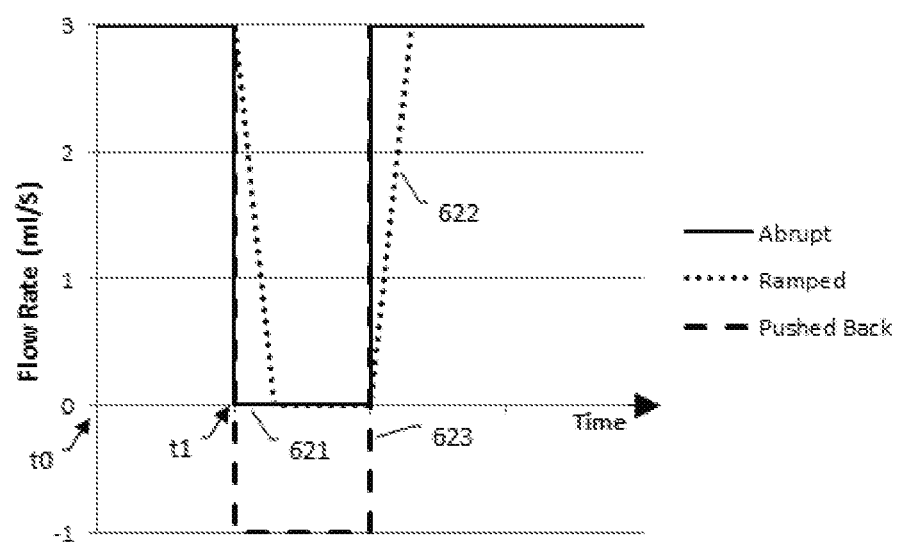
FIG. 28B is a graph depicting flow rate over time when certain actions are taken during an injection according to one embodiment of the present disclosure.

In embodiments of the impedance models described herein, the relevant level of detail of the flows and flow fronts (i.e., the leading edge or portion of the fluid as it is initially pushed through the fluid path) of the various fluids through the fluid path elements may be included or modeled. This enables accurate estimation of, for example, viscosity, density, and time varying resistance and acceleration and thus pressure changes. In an alternate embodiment, the saline flush following a contrast injection initially flows at the programmed rate. As shown in FIG. 28B, the saline flow starts at a time t0 and proceeds at this rate for a length of time t1. Based on the impedance model estimate, the saline flow front will reach the greatest restriction, commonly at the catheter. For example, at or just before the time when the saline flow front is to reach the greatest restriction and thus cause the greatest reduction in resistance, the controller may halt the saline flow. This halt may be abrupt as in trace 621 or intentionally tapered as in trace 622. Alternatively the controller may allow the saline piston and optionally the contrast piston to be pushed backward, resulting in a negative flow rate, by the pressure in the syringe(s) as shown by trace 623 to reduce the pressure to a level at or near the expected steady state saline flush pressure, thereby reducing or eliminating any increase in flow rate. The timing, duration, and magnitude of these actions may depend upon the details of the impedance model and/or the pressure sensor or measurement. The options listed herein may be options that the user may program, select, allow, or confirm.

The model construction or modification may be done before, during, or after an injection. A model built or modified after an injection may be used to inform the diagnosis by being used in combination with the image to understand and determine the actual fluid delivery profile that went into the patient's body. When combined with various physiological phenomena, this will lead to an image properties measurement. A model built or modified after an injection may be used for a later injection, either for that same patient or for subsequent patients. The model may be static or dynamic, or with various aspects of the model being static or dynamic.

Figure 55:
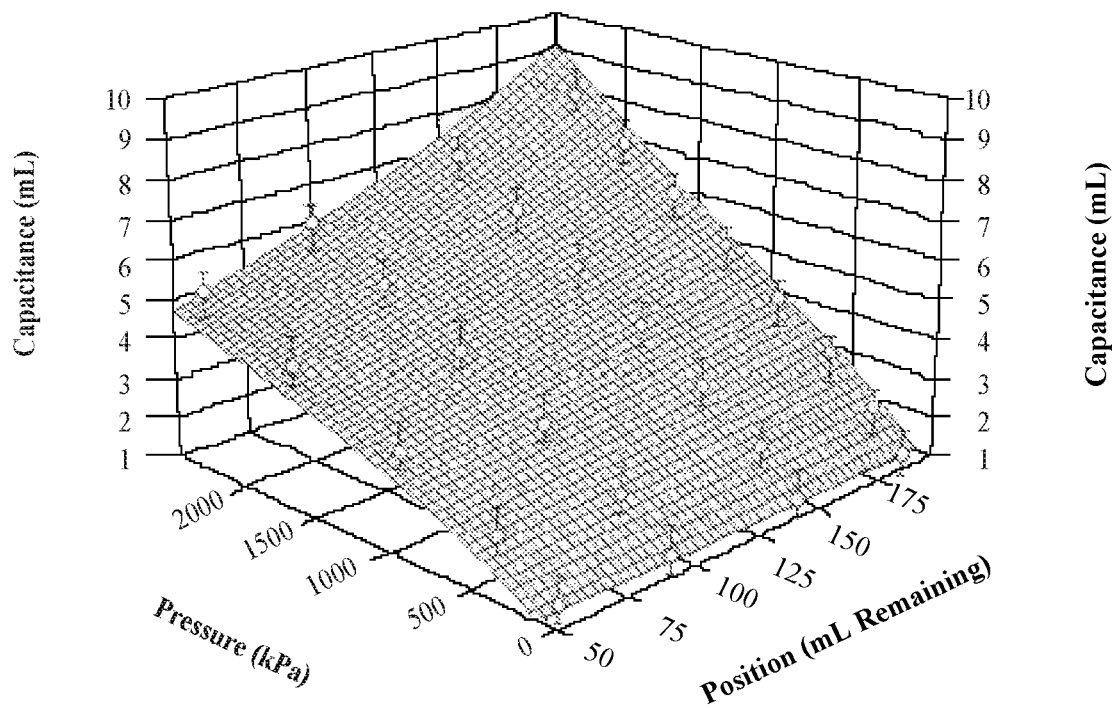
FIG. 55 is an model involving syringe capacitance as a function of pressure in the syringe and plunger position in the syringe.
Figure 56:
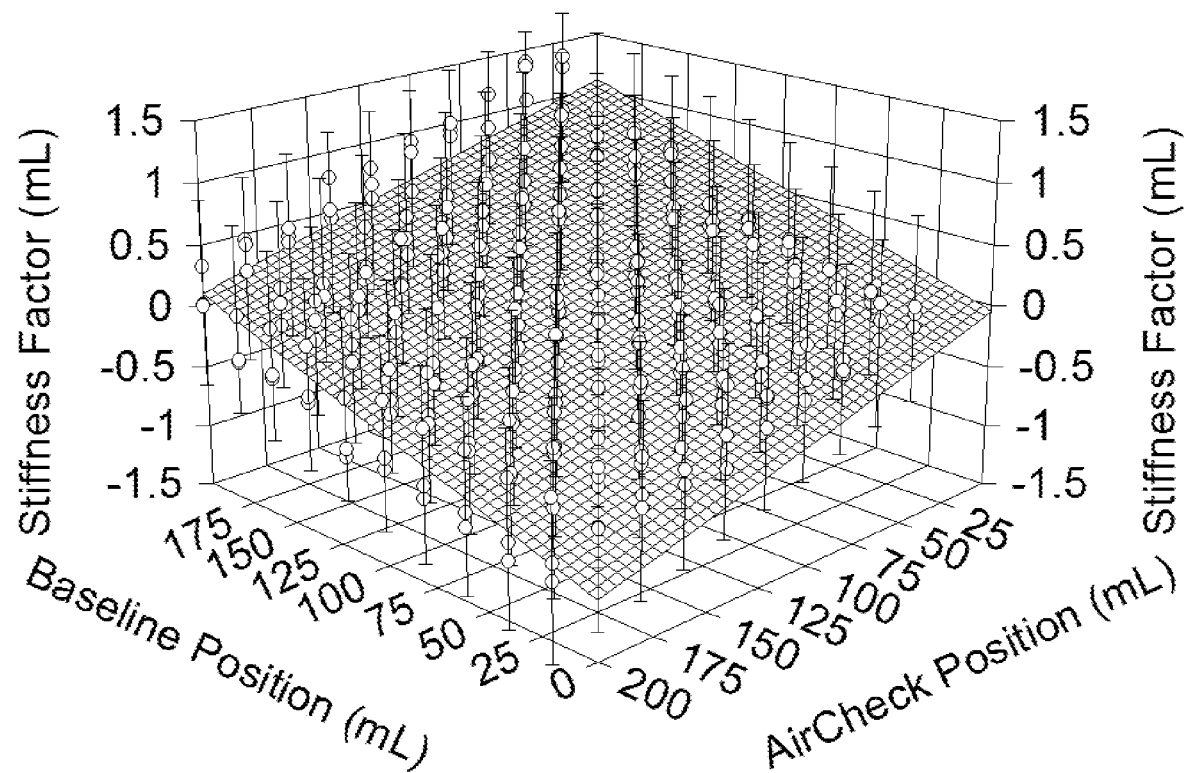
FIG. 56 is a model illustrating adjustments that may be made to an estimation of air volume based upon a baseline plunger position and the actual air check plunger position.

An example model involving syringe capacitance or capacitive volume as a function of pressure in the syringe and plunger position in the syringe is shown as a surface and a corresponding equation in FIG. 55. A second example model of aspects of impedance is shown in FIG. 56. This model illustrates the adjustments that may be made to an estimation of an air volume based upon the baseline plunger position and the actual air check plunger position. Models such as these may be used by the controller before the injection, for example to adjust the planned piston position profile over time to more accurately deliver the desired fluid flow profile in combination with other system impedance information or models, for example about fluid properties and fluid path properties. Alternatively, models such as these may be used dynamically to adjust plunger position and velocity to account for capacitance based upon the actual pressure in the syringe during the injection. Models such as these may be useful if it is not possible to accurately know important impedance information of one or more significant system aspects. These models may also be used in both modes, for example to set an initial piston displacement profile based on the system impedance information at hand, and also used during the injection to recalculate piston position profiles to account for changes or unknowns from the initial profile. Similar multi-factorial models may be created for other impedance aspects. For example a fluid path element, such as a tubing set or catheter may swell with time at pressure and this swelling also may be dependent upon temperature. This may affect capacitance and resistance which is calculated as 1/diameter to the $4^{th}$ power. The relaxation when an injection ends may also be time and temperature dependent.

The simplest model may be a constant relating two variables, which is the slope of a linear relationship between those two variables. A more complex model is curved line relationship between two variables. The surface relationships of FIGS. 55 and 56 are examples where two input variables influence a third variable. More complex, multi-dimensional models may be used, as is apparent from the discussions herein of the many impedance factors that may be relevant to achieve desired system performance. Further associated disclosure related to capacitance development and issues associated with fluid injection systems is described in PCT International Application No. PCT/US2017/020637, filed 3 Mar. 2017, the disclosure of which is incorporated herein by this reference.

Figure 37:
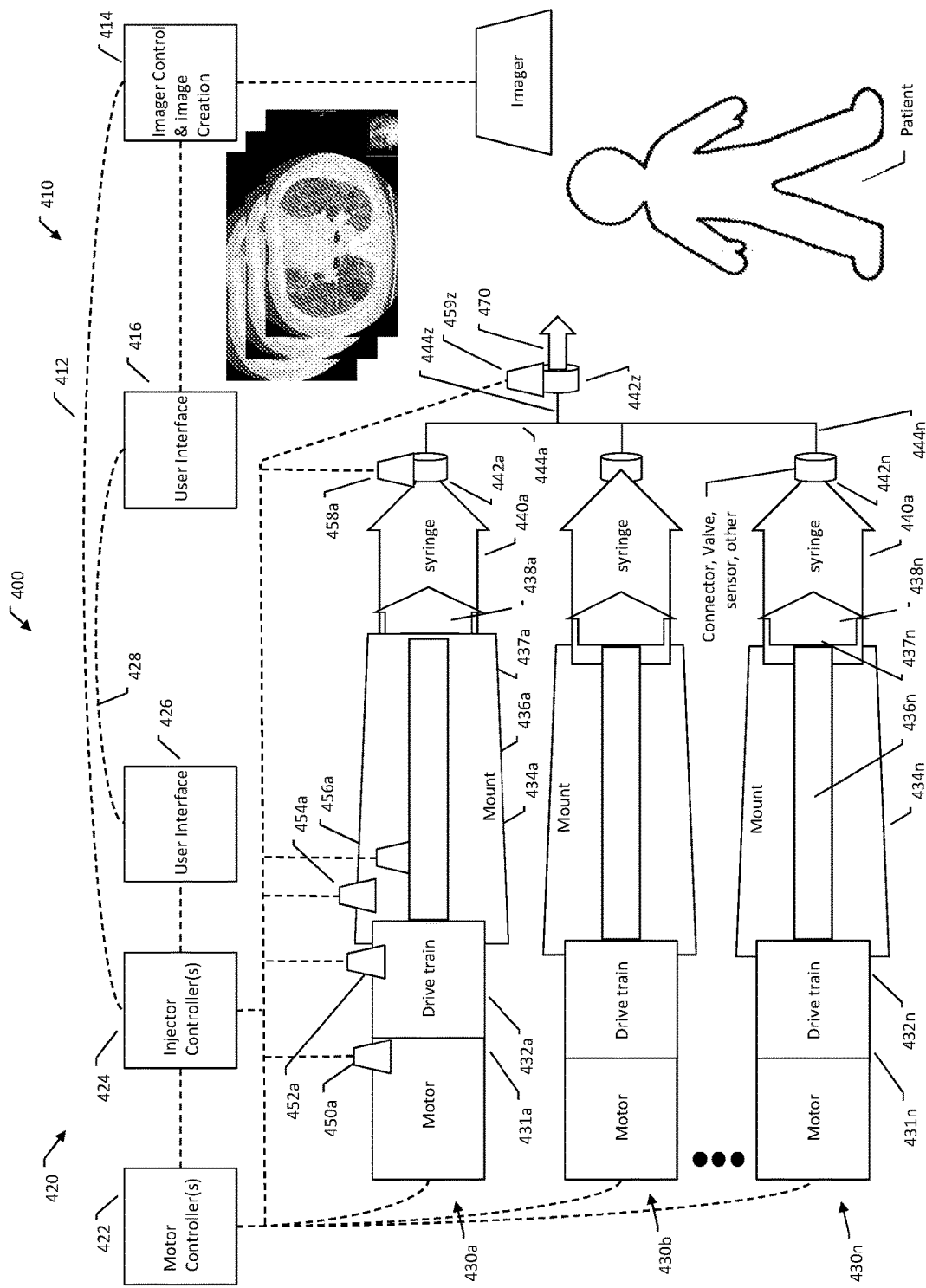
FIG. 37 is a schematic illustration of a multi-fluid injection system according to the present disclosure.

The overall system 400 as depicted in FIG. 37, includes the imaging equipment 410 which creates the image or gathers information from the patient and the fluid injection system 420 which acts on a patient for a medical imaging or information gathering study. As disclosed herein, there are many variations on and complications to the actual design and operation of a multi-fluid impedance model that make it difficult and a non-trivial step from the creation and use of a single fluid impedance model. Further, there are many benefits to investing in this additional work and research, as is also described herein, that are not attainable with single fluid modeling. The systems and models may involve electrical aspects or subsystems, for example, motor control circuitry 422, both analog and digital, sensors 450a-458a, computer systems 414 and 424, and user interfaces 416 and 426. The system and models may involve mechanical aspects or subsystems, for example, gear trains, ball screws, and injector head structures and apparatuses. The systems and models may involve hydraulic aspects, the fluids being delivered, the fluids in the fluid path elements, before, during, and after the end of the delivery, and the fluid path elements associated with them. The systems and models may involve physiological aspects including the fluid movement through, and into tissues in a patient's body. The systems and models may involve imaging aspects of the various imaging modalities, for example response time, resolution, and signal to noise or signal to background ratio.

The fluid injection system 420 comprises a user interface 426, an injector controller 424, a motor controller 422, and one or more fluid delivery subsystems, 430a 430b to 430n. The function of the motor controller 422 and the injector controller 424 may be algorithmically or physically partitioned in various ways, for example from separate motor controllers for each fluid delivery subsystem or a single controller for the whole fluid injection system 420. Each fluid delivery subsystem may for example comprise a motor 431a which converts electrical energy into mechanical energy, a drive train 432a and piston 436a with a piston head 437a which may convert mechanical energy into linear motion energy, a syringe with a barrel 440a, a plunger 438a and an outlet with a connector, valve, or other fluid path conduit 442a. The drive train and syringe are held in position relative to each other by a mount 434a so that the piston head 437a may exert a force to move the plunger 438a through the syringe barrel 440a to create a pressure in the syringe to control the flow of fluid out of or into or within the syringe. Each subsystem contains one or more feedback sensors or measurement sensors, shown for example as 450a, 452a, 454a, 456a, and 458a. A sensor may, for example, measure position, speed, acceleration, voltage, current, force, temperature, strain, pressure, flow, velocity, fluid type, fluid viscosity, fluid presence or absence and/or valve position. Optical readers can also be present to capture images from which one or more of these or other properties may be derived, for example, position, engagement, continuity, cleanliness, and bar code or other device information. One or more subsystems may incorporate additional or other sensors at positions not illustrated in this exemplary diagram. To avoid overcomplicating the diagram, the similar sensors for the other fluid delivery subsystems 430b to 430n are not shown. The sensors may feedback directly to the motor controller, for example a motor position sensor or encoder 450a used with proportional-integral-derivative (PID) servo control, or to the injector controller, for example a strain sensor on the mounting 434a to assess the pressure in the system and adjust the fluid delivery rate to stay within a given pressure limit. The fluid is carried from the syringe 440a through fluid path element 444a. Various fluid path elements may come together at one or more points, ultimately connecting at fluid path element 444z which is connected by a connector or valve 422z to the needle or catheter 470 which delivers the fluid to the patient. The user interacts with the two systems through their respective user interfaces 426 and 416. The user selects or determines the programs, protocols, or actions of the respective systems through the user interfaces 426 and 416. The user interfaces 426 and 416 may be a single user interface and/or may communicate directly with each other through a path 428. The injector controller 424 and the imager controller 414 may also communicate and interact with each other through a path 412. The fluid injection system 420 comprises one or more fluid delivery subsystems 430a, 430b to 430n. Each subsystem is driven by a separate or common motor controller 422 according to the program of the user adjusted to account for the impedance related and other non-idealities discussed herein.

Figure 38:
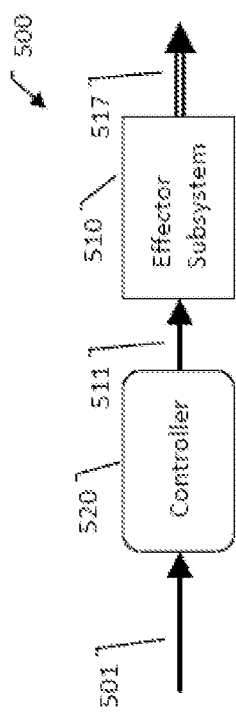
FIG. 38 is an example of a known open loop control system.

FIG. 38 shows an example open loop control system 500. An input signal 501 is translated by a controller 520 into a control signal 511 which acts on an effector subsystem 510 to create output 517. The controller 520 may use or incorporate information about the effector subsystem 510 to determine the output 517 that will drive the effector subsystem 510 to create the desired output 517.

U.S. Pat. No. 3,156,236 discloses a constant pressure angiography injection system which uses this type of open loop control. A motor is used with produces relatively constant torque for a given input voltage. Thus the user's desired or controlling input signal 501 is injection pressure. This is translated into a voltage control signal 511 which is applied to the motor, slip clutch, drive system, and syringe arrangement. There is no feedback of any kind in the injection system. Although not expressly stated, the slip clutch may be a way to limit the pressure or force delivered, most likely so that when the piston comes to the front of the syringe, it does not break the syringe or destroy the apparatus. A drawback to such an open loop, pressure controlled system is that the other impedance characteristics of the system including fluid temperature viscosity, catheter diameter and lengths, and therefore resistance, and other variables will affect the flow rate that is achieved. Thus the reliance on pressure setting alone can produce unpredictable flow rates under varying conditions.

Figure 39:
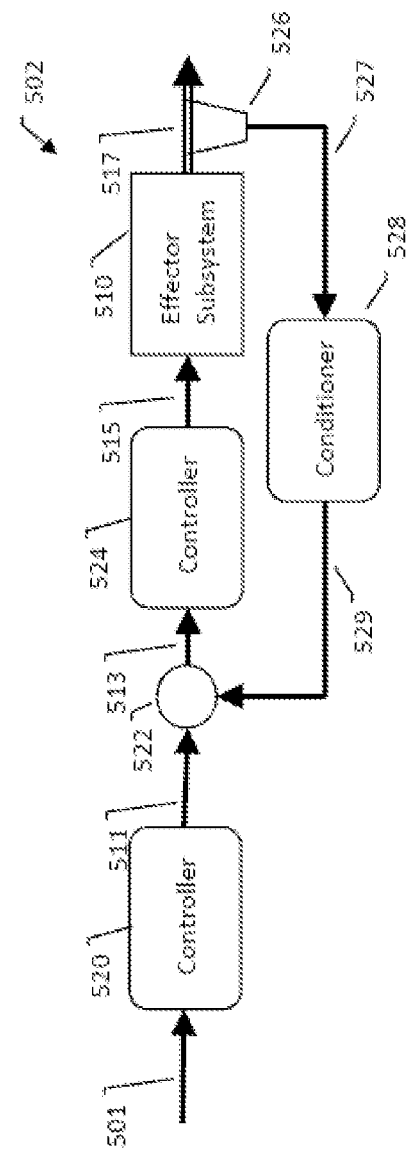
FIG. 39 is an example of a known closed loop control system.

FIG. 39 shows an example simple closed loop control system 502. The closed loop system generally comprises the open loop system 500 with the addition of at least one sensor 526 which provides at least one signal 527 representative of at least one output 517. The signal 527 may be acted upon or transformed in some way by a conditioner 528 to provide a feedback signal 529. The feedback signal 529 and the control signal 511 are combined in a signal combiner 522 to create a signal 513. For example, in the case of simple negative feedback signal 513 equals signal 511 minus signal 529, which may be called an error or difference signal. This signal 513 is conditioned by controller 524 to create control signal 515 which activates the effector subsystem 510. In regard to fluid injectors, example input signals 501 may be flow rate, velocity, volume over time or position over time.

In U.S. Pat. No. 3,623,474, to Heilman et al., incorporated herein by reference, the world's first flow controlled injector, a simple single loop feedback system is described where the input signal 501 is flow rate. The control signal 511 is motor speed. The combiner 522 subtracts the actual speed 529 from the desired speed 511 and sends that to the controller 524. This eliminates the need for the user to try to set the pressure of the injector based on an estimate of system impedances. In U.S. Pat. No. 3,623,474, the feedback of the flow rate signal causes the pressure to increase (up to a pressure limit) to achieve the desired flow rate. U.S. Pat. No. 3,623,474 further discloses a tripping circuit that halts the motor if the flow rate exceeds the selected rate. This safety monitoring circuit is not shown in FIG. 39. It monitors the operation but does not act unless the threshold is exceeded, at which point it stops the injection. Thus, with a feedback loop such as this, the actual flow rate will approximate the desired flow rate independent of the impedance characteristics of the injector and fluid path elements. With proper design and/or tuning of the controllers and conditioner, there is no need for the operator or injector to know any of the impedance characteristics of the injector system (including for example contrast concentration, viscosity, temperature, or fluid path element properties), as long as the pressure limiting condition is not reached.

U.S. Pat. No. 9,242,083 states that "actual flow rate of the medical fluid utilized in the injection protocol may be adjusted based, at least in part, on an inherent system elasticity of the injection system." When considering a feedback system of FIG. 39, this pre-feedback loop adjustment may be considered to take place in controller 520 with the input 501 being the desired flow rate profile and the output 517 being the input drive speed to the motor and drive train. The controller 520 uses one type of impedance characteristic, "an inherent elasticity of the injection system," to make its adjustments. The specification is not specific whether there is feedback through a conditioner such as 528 but it is assumed. Since the disclosure of U.S. Pat. No. 3,623,474, position or velocity feedback has been in the art of fluid delivery injectors. This open loop anticipation of the system action is useful in injector systems where the flow rate being measured is at the piston or plunger, not at the catheter or the patient.

Figure 40:
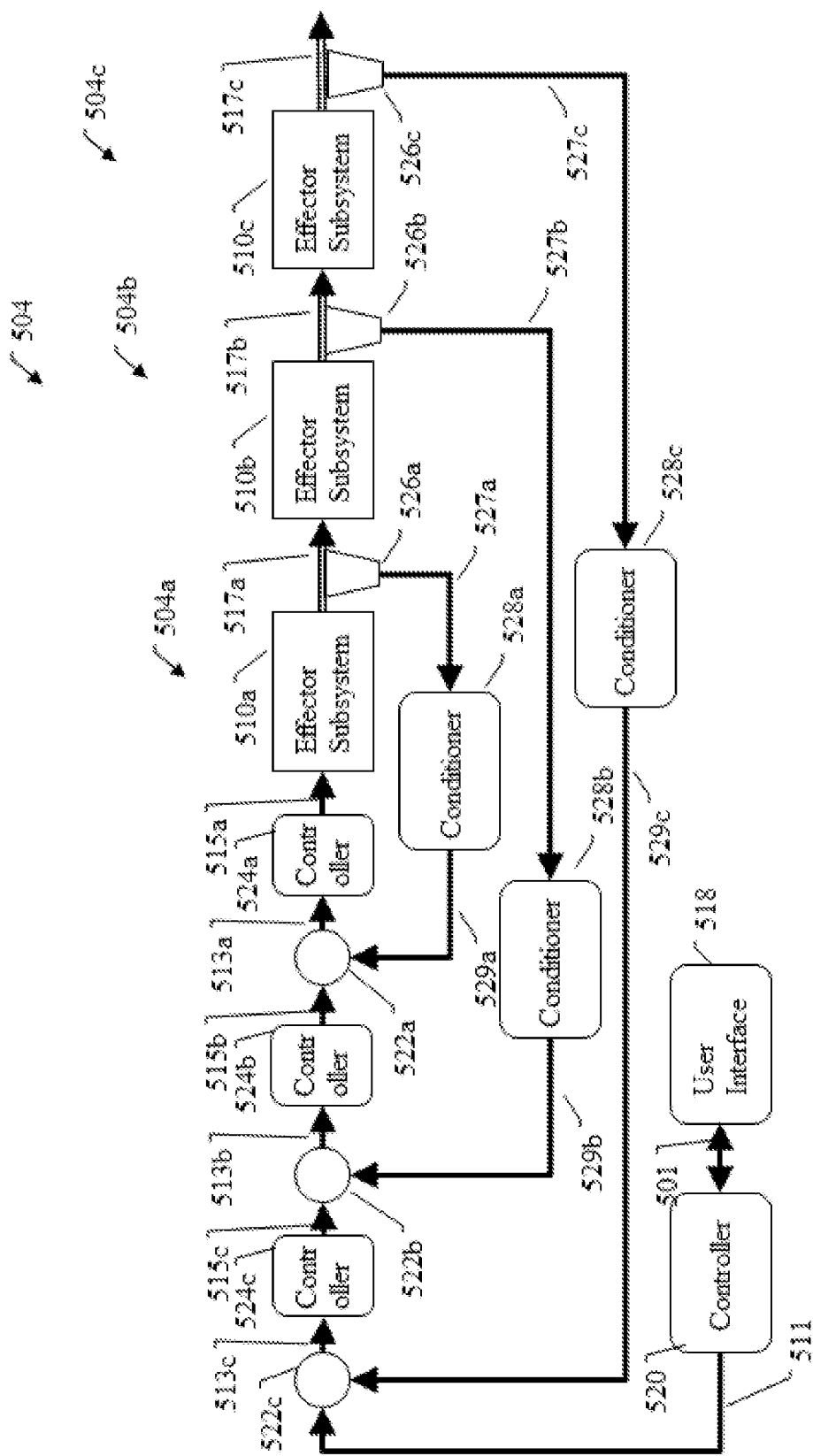
FIG. 40 shows an example of a multi-loop and/or multi-variable feedback control system according to one embodiment of the present disclosure.

FIG. 40 shows an example of a multi-loop and/or multi-variable feedback control system 504. In this example the system 504 consists of three feedback loops 504a, 504b, 504c consisting of numbers with corresponding subscripts and elements therein, arranged in a nested configuration. In this example, feedback loop 504a is fully within feedback loop 504b, and similarly feedback loop 504b is fully within feedback loop 504c. The controllers 520 and/or 524a, 524b, 524c and/or conditioner 528a, 528b, 528c may receive inputs 527a, 527b, 527c from multiple and/or the same sensors 526a, 526b, 526c at multiple and/or the same points 517a, 517b, 517c in the system. For example sensor signals

527*a*, 527*b*, 527*c* may be a motor position signal, a motor current signal, a motor velocity signal, and/or a piston force signal.

Controllers 520 and/or 524*a*, 524*b*, 524*c* and/or conditioner 528*a*, 528*b*, 528*c* may use or incorporate one or more pieces of information about the system impedance in their algorithms to transfer inputs into outputs or to derive or estimate hidden or unmeasured system variables. For example, one variable for an injector to control is fluid pressure in a syringe. An example signal 527*a*, 527*b*, 527*c* which may be measured which is related to syringe pressure is motor current. However the relationship between motor current and pressure incorporates multiple impedance effects, for example syringe plunger friction and drive train inertia. Furthermore, the syringe plunger friction may be pressure dependent and thus may be incorporated into the impedance mode. By incorporating this knowledge into conditioner 528*a*, 528*b*, 528*c*, a more accurate estimate of syringe fluid pressure may be made. In addition, estimates of pressure elsewhere in the system, for example at the catheter inlet, may be made.

One example benefit that this enables is faster motor acceleration and thus fluid flow rise time, in situations where that is desirable. Another example benefit is that it enables more accurate pressure limiting performance and thus the achievement of higher flow rates than might otherwise be achievable. In addition, the impedance models and thus conditioners 528*a*, 528*b*, 528*c* and controller 524*a*, 524*b*, 524*c* may be non-linear and depend upon sensors or computed system variables which are not explicitly shown in FIG. 40. As described below, Equation 66 and its associated derivation set forth another approach utilizing information about the injection procedure.

One example of control system 504 comprises a motor (or piston) position feedback control system 504*a* that measures piston position using an encoder and a pressure limit control system 504*b*. The pressure limit may act to limit behavior, meaning that it has no effect unless the pressure signal 527*b* (actual or estimated) exceeds some safety limit. Only if some upper pressure safety limit is approached or exceeded is the signal 515*b* affected. For example, the injection may be stopped if the pressure limit is exceeded by a set amount for a set time. In some embodiments of this disclosure, the pressure feedback loop is used in a more active way, for example to reduce the system pressure and thus the flow pulse when transitioning from a more viscous to a less viscous contrast.

The impedance modeling and impedance information incorporating feedback loops of this disclosure may include other configurations beyond simple nested systems, but this example of FIG. 40 is given for clarity. Feedback loops may be in series, in parallel, nested, arranged in a mesh and/or any other arrangement known to those skilled in the art.

Figure 41:
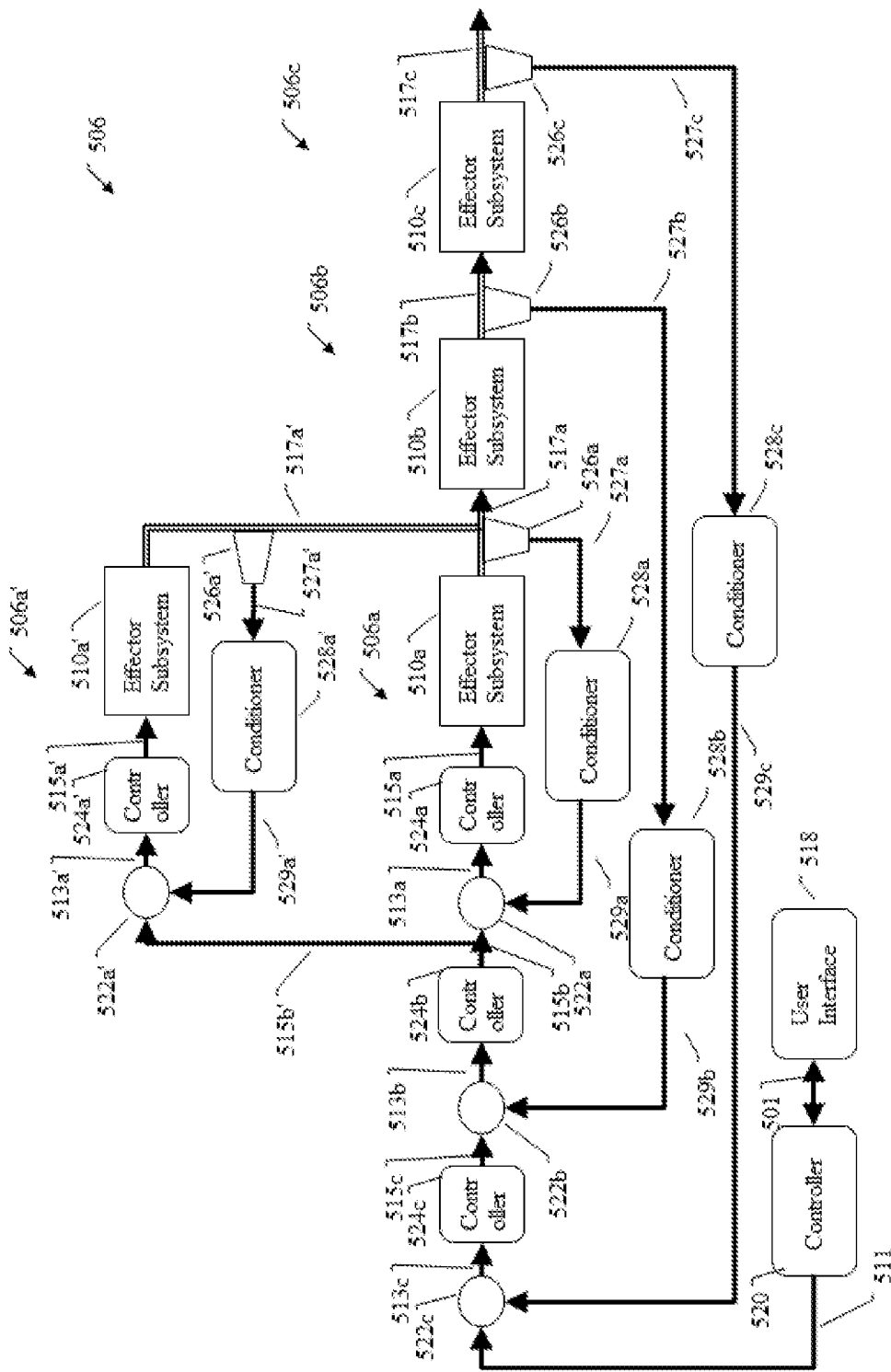
FIG. 41 is the feedback controller system of FIG. 40 further depicting additional aspects of the system according to the present disclosure.

Considering FIG. 41, the feedback controller system of this figure may be used for an injector which may deliver two fluids sequentially and/or simultaneously. There may be a first position feedback loop 506*a* for one fluid, for example contrast, and a second position feedback loop 506*a*', for the second fluid, for example saline. The respective input signals to the two loops may come from a single controller 524*b* which thereby controls the ratio of contrast to saline and provides output signals 515*b* and 515*b*' to the respective combiners 522*a* and 522*a*'. This example system may be useful in understanding embodiments where the ratio of contrast to saline is controllable, for example during programming, in real time, or adapted in real time to account for one or more impedance aspects of the system. Some impedance aspects may be known and are not expected to change, for example those of the motor and mechanical drive which are used repeatedly. Other impedance aspects may be known, such as geometric properties of connector tubes and impedance aspects of syringes. They will change if different fluid path elements are used. Other impedance aspects may change during use. For example connector tubes may swell (i.e., grow in inner diameter based on pressure, temperature, and time at pressure). Other impedance aspects, for example the temperature of fluid in the connector tube and its viscosity, may only be known with great difficulty or may be unknowable. Even some, such as the drive train properties, may change due to mechanical wear or overheating. Thus the impedance factors and/or model may be used by the control system to confirm that the operation is going as expected or to alter if something unusual or dangerous is happening. Alternatively, if some impedance factors, for example contrast temperature or connector tube properties, are not known, the system may use a reasonable initial estimate or range of estimates, adjust the impedance model before, during, or after the injection, and only alert the operator or take other action if one or more impedance property is outside of reasonable ranges.

An example embodiment of this disclosure utilizes the contrast entity delivery rate, for example for X-ray contrast, milligrams of iodine per second (mgI/S) and contrast entity concentration, for example for X-ray contrast, milligrams iodine per milliliter (mgI/ml). These quantities maybe used internally by the controller, communicated to the operator, and/or used by the operator and/or the system when making recommending, selecting, and/or setting properties to prepare for an injection. The operator or the system may select the contrast dose (by molecules or another similar measurement) and dose rate to be delivered and the system will provide that dose of contrast molecules and dose rate (molecules per second) at a concentration that provides the optimum contrast flow and image results, optionally within concentration limits or ranges set by the operator or the system. The various nested, meshed, interwoven or otherwise related feedback loops may for example include syringe plunger position, fluid volume, delivery rate, or fluid velocity of a single fluid (or axis) as one level. A downstream measured volume, velocity, or delivery rate may be another level of feedback loop. The concentration or contrast molecular delivery rate may be another level. Pressure at some point or points in the system may be used as a feedback loop as well, for example as a safety limit or as a parameter to be achieved and controlled at a desired level over time. Image properties or attributes such as contrast concentration or image signal may be a feedback loop. There may be more than one imaging contrast present, for example for use with PET/CT or PET/MR and there may be a control loop that controls the relationship of the delivery of those two different contrasts, for example based on a time relationship or an image result. Patient parameters such as heart rate, respiration rate, blood pressure, hydration status, clotting time, and others may be a feedback loop either to be monitored or to be controlled over a desired range at some level, in an embodiment in which the injector has something other than contrast and/or saline as one of its fluids, for example a physiologically active or therapeutic fluid such as a cardiac stress agent or beta blocker. Time may be a critical parameter in some uses of this system, for example injections such as angiography, so that time may be a control loop that operates and takes precedence over some of the other control loops, for example stopping the injection when the imaging is complete or at a time when it would have no further effect, no matter how much contrast had been delivered. The imaging system may provide input to one or more control loops, depending upon the variable(s) being controlled.

Figure 42:
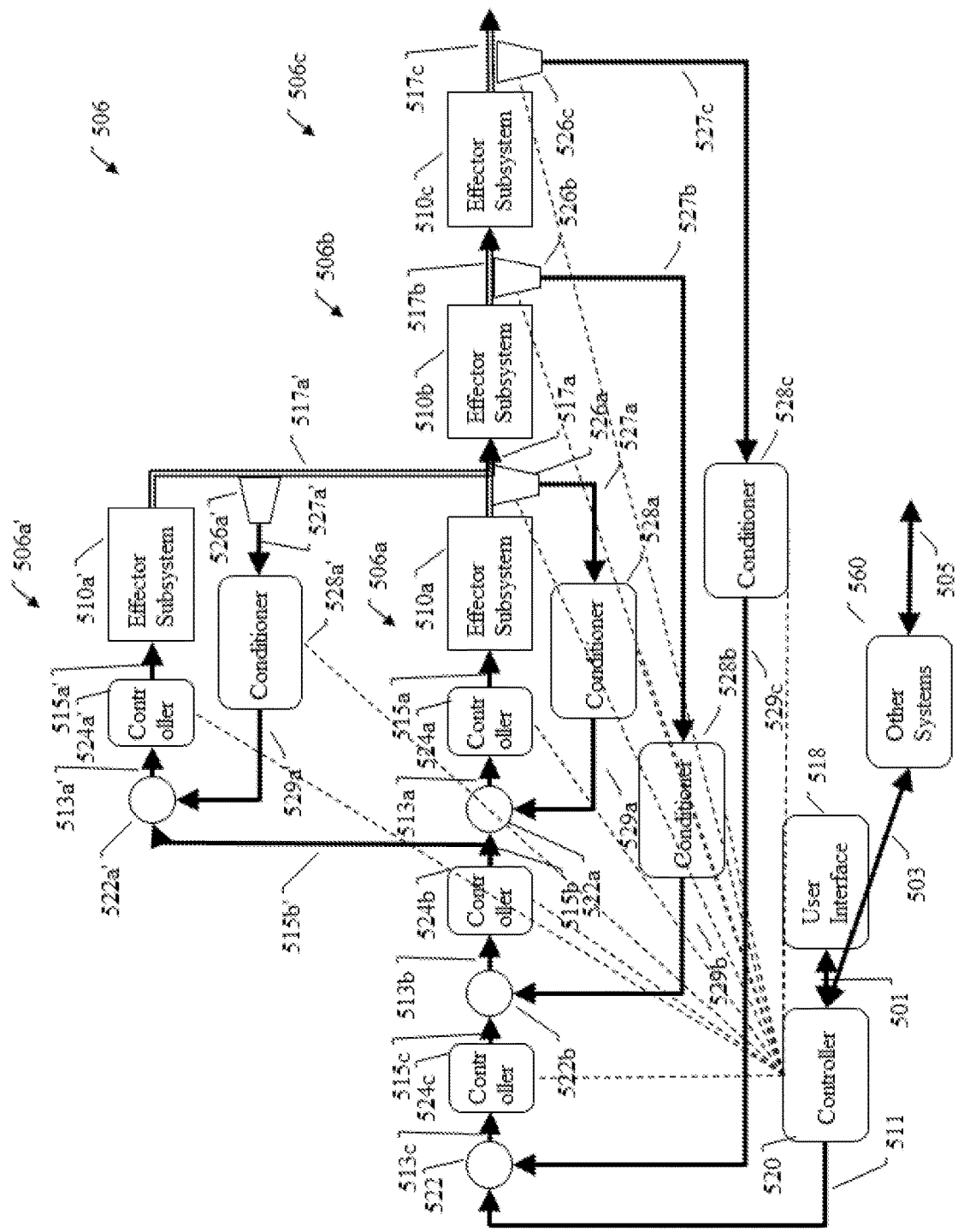
FIG. 42 is the feedback controller system of FIG. 41 further illustrating communication channel lines according to the present disclosure.

Another example embodiment of this disclosure may be angiography, and more specifically angiography through microcatheters. There is a need to inject contrast through relatively long and relatively narrow catheters. The position or velocity feedback control loop is designed and will attempt to cause the injector to develop the pressure necessary to deliver the fluid at the desired flow rate. In many situations, the resistive aspect of impedance of the catheter, as affected for example by diameter, length, and fluid viscosity is too high and thus the injector pressure limits to avoid rupturing the catheter and is not able to deliver the contrast flow rate that the user desires. In an aspect of this disclosure, as illustrated in FIG. 42, the controller 520 receives information, illustrated by the dotted communication channel lines, about the system, for example system configuration, system impedance, and/or system performance from one or more inputs, for example the user interface 518, any of the system controllers, conditioners, sensors, and/or other data input devices (not shown) such as bar code readers or other devices which may provide input about the impedance aspects of any part of the system. The communications arrangement in FIG. 42 is a star topology or master-slave configuration. Other communication networks such as loop, network, peer to peer, mesh or those known to those skilled in the art may be used. Individual controllers may be combined, may be performed by a single computer system, or may consist of multiple computer systems. The controller 520 may acquire and use impedance information from a test injection, calibrations or from previous injections. In an embodiment of this disclosure, the controller 520 may inform the user through a user interface 518 that a pressure limit is likely to occur and optionally to suggest the maximum flow rate that is expected to be achievable under current and/or anticipated conditions. If the user desires this likely maximum flow rate, the user may change the flow rate to the recommended flow rate or accept the change from the system and proceed with the injection. Alternatively, the user may keep the original flow rate, recognizing that pressure limiting is likely to happen. Alternatively, the user may propose and/or make changes to one or more impedance aspects of the overall system, for example, warmer contrast, a less concentrated contrast, a shorter catheter, a larger diameter catheter, a catheter with a higher pressure rating and/or other changes may be implemented, and then the system will reassess the relevant aspects of impedance and determine if the desired flow rate is achievable. This may repeat until the user is satisfied with the expected injection. Alternatively, the controller may make one or more recommendations or proposals to change one or more impedance aspects of the overall system, preferably indicating the improvement that could be expected with each. The user may then accept one of the proposals and then the user and/or the injector system may make the necessary changes.

Imaging contrast agent is injected into the body so that it may be detected by an imaging system, for example using X-rays, gamma rays, radio waves, ultrasound energy, light energy or some other form of energy. To a first order, the image signal generated is linear, that is proportional to the number or mass of the contrast atoms or molecules per unit volume of blood or tissue intercepted by the imaging system. There are second order effects which may make the response non-linear with concentration, for example beam hardening effects with X-rays, signal saturation, T2, or T2* effects with MR, pulse pileup in nuclear medicine, or shadowing with ultrasound. In angiography, in an example where a planar X-ray image is being taken, for a given contrast density, for example milligrams of iodine per milliliter (mgI/ml) the image signal of a blood vessel decreases as the vessel diameter decreases because the depth of contrast imaged in a pixel (a fixed area path from the X-ray source to the detector) decreases with vessel diameter. Thus to achieve maximum vessel visibility to the farthest extent possible distally down a vascular tree, it is desirable to use contrast of the highest concentration achievable and for the flow rate of the injection to be high enough that the vessel is fully filled with the contrast as it leaves the catheter and enters the vessel. Otherwise the contrast may be diluted with blood and thereby the reduced concentration and/or partial filling may lead to artifacts.

Figure 43:
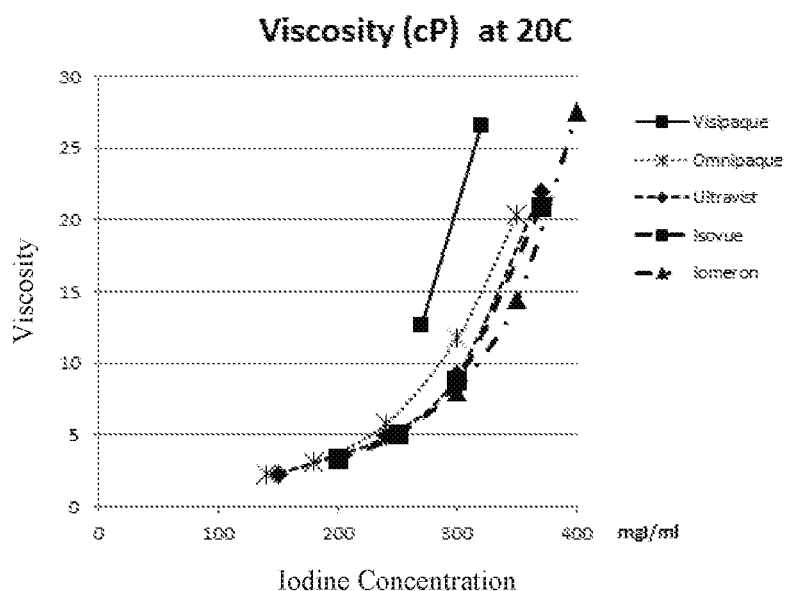
FIGS. 43 and 44 are graphs depicting the viscosities of various concentration levels of contrast agents plotted against iodine concentration as a function of temperature.
Figure 44:
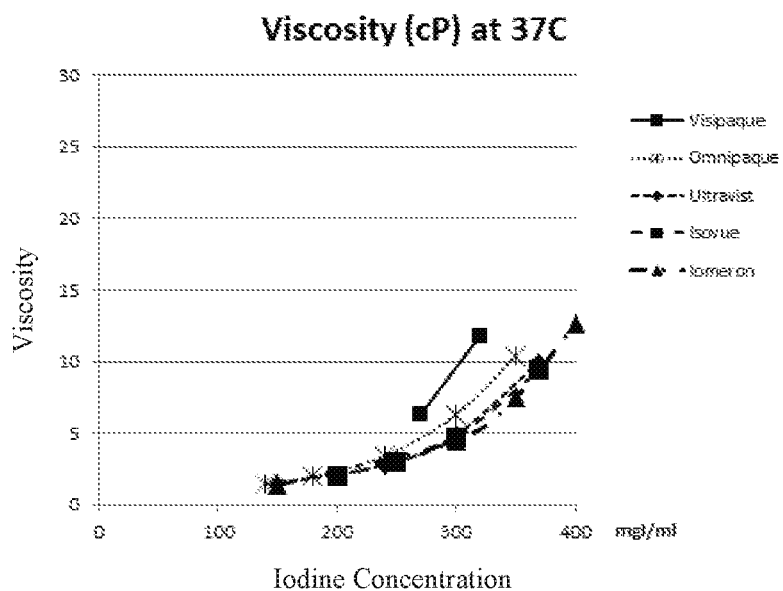
Figure 45:
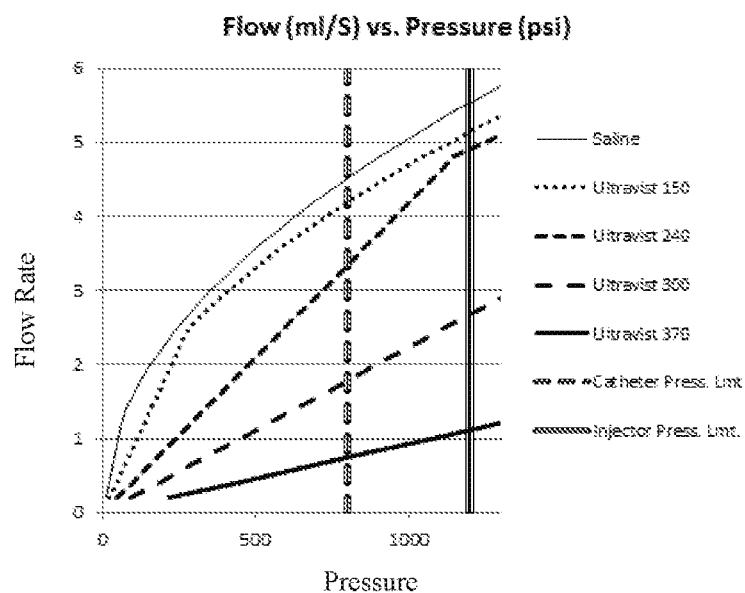
FIGS. 45 and 46 depict the flow rates and iodine delivery rates for various contrast agents over pressure.
Figure 46:
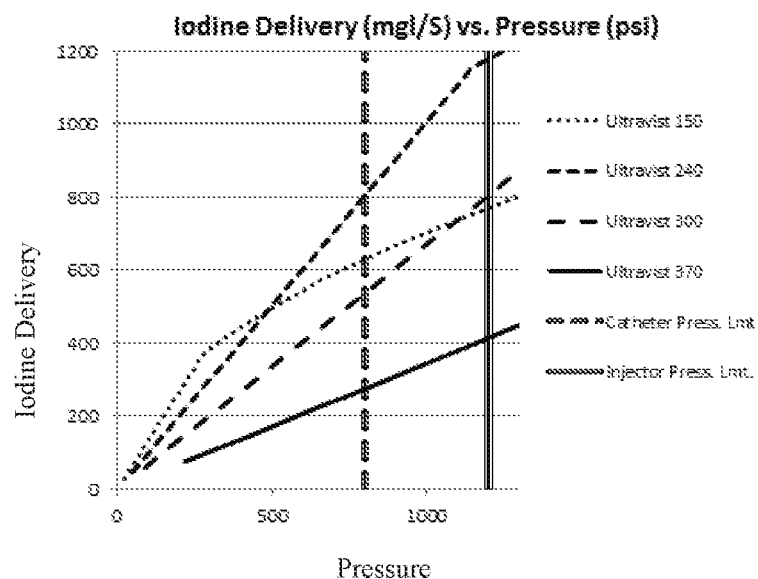
Figure 47:
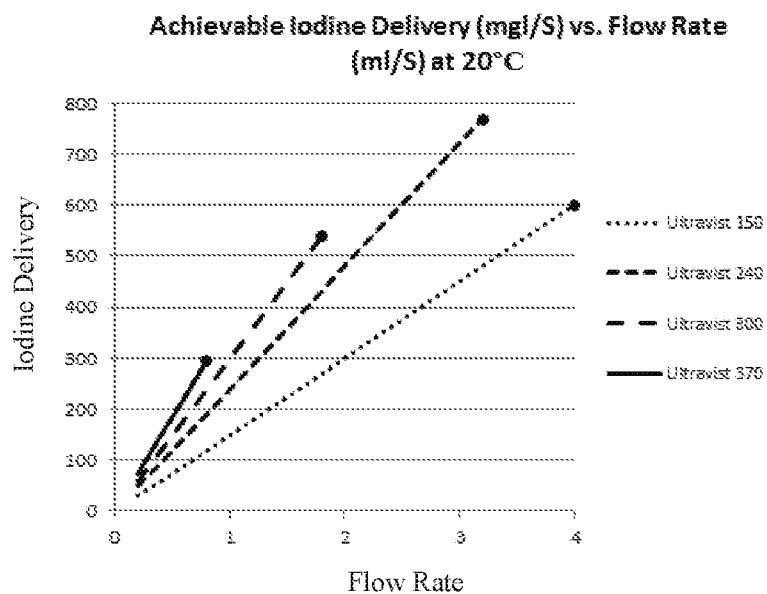
FIG. 47 depicts iodine delivery rate vs. flow rate for various contrast agents.

When using an injection system with two liquids of different viscosities, for example contrast and a flushing solution such as saline, moving from a higher viscosity, higher concentration contrast to low viscosity, lower concentration contrast may counterintuitively enable a higher contrast material delivery rate in milligrams of iodine per second (mgI/S), at a slightly higher volumetric flow rate in milliliters/S (ml/S) because contrast viscosity falls faster with dilution than contrast concentration. This higher iodine delivery rate may be achieved by selecting a different, lower viscosity contrast or by simultaneously delivering contrast and the flushing or diluting solution. The viscosities of various concentration contrasts are plotted against iodine concentration (mgI/ml) in FIGS. 43 and 44. Concentration, temperature, and/or viscosity are examples of an impedance aspect or property which may be provided to the injector control system for use by the controller in this disclosure through a user interface or an interface 503 to other data systems 560 such as, for example, the injector manufacturing company's data communication vehicles, the imaging equipment, the hospital information system, or the internet. In addition, the impedance aspects of various catheters may be provided to the controller. For example, if the length and diameter of a fluid path element, such as a known connector tubing or a catheter are provided, the controller may compute or model the relationships involved, for example between the pressure drop across the fluid path element, flow rate in ml/S, and iodine delivery rate in mgI/S with various fluid properties, including contrast concentrations. FIGS. 45 and 46 show an example set of relationships with various contrasts at 20° C. for a 135 cm Boston Scientific Renegade HI-FLO Fathom catheter which has an 800 psi pressure limit. Flow rates are generally linear with pressure and viscosity under laminar flow conditions but become non-linear under turbulent conditions. Both types of flows may be modeled. From these relationships, the controller may compute the maximum flow rate and achievable iodine delivery rate for each contrast concentration. FIG. 47 displays the iodine delivery rate vs. flow rate with the line ending at the maximum flow at the pressure limit of the catheter. This information may be used to recommend the contrast concentration to give maximum image signal to be used, if the user can estimate the flow rate of the vessel to be opacified or if the flow rate is known from previous injections.

Figure 48:
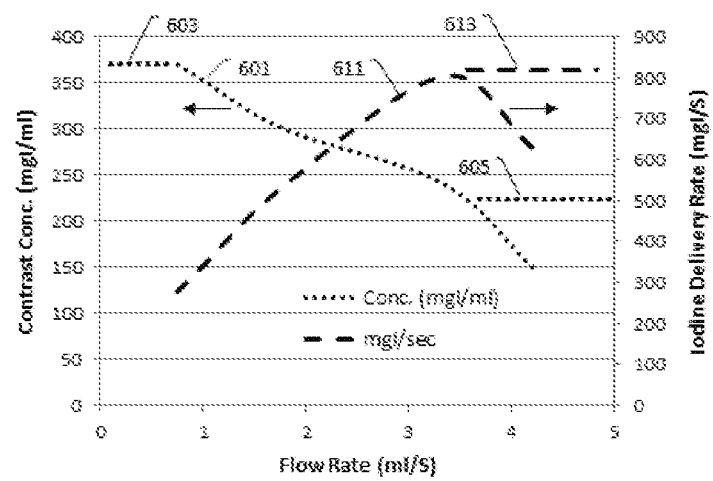
FIG. 48 depicts iodine delivery rate and contrast concentration as compared to flow rate.

Alternatively, this information, as shown in a different format in FIG. 48, may be used to aid in explanation and understanding of this disclosure, and may be used by the controller to recommend or set a contrast concentration (and thus viscosity) to use for an injection. In this example, the contrast concentration in one syringe is Ultravist 370. Curve

601 shows the contrast concentration (referencing the left axis) that gives the maximum iodine delivery rate at the fluid delivery rate chosen (horizontal axis). Below about 0.7 ml/S, the optimum is pure contrast, Ultravist 370, as the iodine delivery rate, curve 611, is not pressure limited but flow rate limited. This use of the most concentrated contrast is illustrated by line 603. Above a flow rate of about 3.3 ml/S, going to concentrations lower than about 220 mgI/ml does not increase the iodine delivery rate, but actually reduces it. Thus for situations that require higher flow rates to fill the vessel, it may actually be better to stick with a concentration of 220 mgI/ml and accept the pressure limiting and dilution by blood in the vessel. This is illustrated by line 605. While this is shown in graphical form for the understanding of the reader, it may be used as data, for example tables, equations, algorithms, subroutines, in the controller to make appropriate recommendations or take actions. For example, if the user initially selects a flow rate that is too high and there is initially backflow retrograde to the catheter tip in the vessel, the user may use a hand controller as part of the user interface to reduce the flow rate or an imaging processing unit may recognize the retrograde flow and signal the injector to reduce the flow. In this case, the injector may in real time increase the concentration to maximize the vessel opacification.

In an alternative embodiment, the controller may also compute the pressure drop across the connector tube which is being used as one of the fluid path elements. The presence and information on the connector tube may be communicated through any of the means known to those skilled in the art. As an example, the connector tube may have a diameter and length such that the pressure drop across it may be about 5% of that of the catheter used in the example above. In addition, the syringe plunger may have a running friction under pressure that starts at about 15 psi and is increased to about 40 psi at a syringe pressure of about 800 psi. The controller of this embodiment may use these aspects of impedance information to optimize its actions to deliver as much contrast as possible through the catheter while keeping the pressure at the catheter inlet below its rated maximum of 800 psi. For example, the controller may use motor current as the sensed property or measurement in the control loop for pressure in the syringe. Alternatively it may use strain in the system mount that holds the syringe in place. A motor current measurement may include both syringe pressure and syringe plunger friction in its measurement. And, as mentioned, there is a pressure drop as fluid flows from the syringe to the catheter input. In a simple, conservative operating mode, the controller limits the motor current to a pressure equivalent to 800 psi and thus the pressure at the catheter input will be about 800-40-40, or 720 psi. In an example of this disclosure of a controller optimizing performance by using impedance information, the controller seeks to limit the catheter pressure to 800 psi, thus the pressure limit at the input of the connector tube is calculated to be 800+5%*800=840 psi. The controller also recognizes that the syringe plunger friction adds the equivalent of 40 psi at this motor current pressure measurement. Thus in this example, the controller will set the motor current pressure limit feedback loop to maintain the pressure limit of 880 psi as measured by motor current and the maximum pressure at the catheter inlet will be 800 psi. Extending this example further, the controller may recognize that the speed of pressure transmission from the syringe to the catheter is further affected by capacitance of the syringe and impedance of the connector tubing, and thus may allow time limited spikes in motor current above the 880 psi level. Utilizing this aspect of the present disclosure may be used to achieve rapid or high rise times.

In an embodiment of this disclosure, when a higher concentration of injectate is desired than can be delivered given the impedances and pressure limit of the catheter, the injector may preload the catheter and/or the connector tube with the highest concentration injectate. This may be done at a slower flow rate, so as to not pressure limit. Once the tube is full of high concentration contrast, the injectate concentration may be reduced and the volumetric flow rate increased. This provides an initially high concentration of injectate which is carried downstream and helps visualize the smallest vessels while less concentrated injectate fills the more proximate, larger parts of the vessel tree.

In one type of angiography called rotational angiography, the image may be reconstructed similar to what is done in CT. In rotational angiography, contrast of a lower concentration is preferred to avoid creating artifacts or inaccuracies in the images. In this procedure, for example, the user may set a maximum iodine concentration or iodine delivery rate, or may program an iodine concentration and flow rate, or iodine delivery rate.

In U.S. 2014/0276550, incorporated herein by reference, a fluid delivery system is provided which incorporates one or more feedback loops utilizing one or more variables and including the ability for different feedback loops to assume control or be the controlling feedback loop or variable during different times or phases throughout the injection. In U.S. 2014/0276550 the feedback loops were not informed about the specific aspects of the system impedance involved, except in the normal feedback loop tuning process. In the present disclosure, one or more of the controllers or conditioners may explicitly incorporate and use information about the impedance of the system and the controlling feedback loop may change during the injection, for example from flow rate, to contrast molecule delivery rate, to pressure, and so on.

A multicomponent impedance model of this disclosure may also be used to check for air or leaks. A multicomponent impedance model expands upon those discussed in WO 2018/089882, which is incorporated herein by reference by providing additional information and more accurate assessment for a wider range of fluids, fluid path elements, and injection conditions.

Using the impedance modeling capability of this disclosure, before an injection, the user may be shown the programmed injection and the actual anticipated injection considering impedance aspects. During and after an injection, the user may be shown the programmed injection, the anticipated injection, and the actual injection, including parameters that are not actually measured but may be estimated through use of the impedance model. This may include the injector system tracking the fluids in the tube, either from priming, from previous deliveries, or from pre-injection delivery to fill the tubing and/or catheter with an initial contrast load. The initial behavior will of course depend upon the fluid(s) that are initially in the fluid path elements.

An additional aspect of impedance that may be considered in one or more embodiments is the mixing of two fluids and the displacement of one fluid by another fluid flowing through a tube or other fluid path element. In a laminar flow situation, the fluid entering a tube flow preferentially down the center of the tube with a parabolic profile. The flow at the center is twice the average flow.

There are several different benefits of and needs for creating a model of specific aspects of a multi-fluid fluid injection system and its impedance. Fluid assessment and confirmation of the fluids within the fluid injection system allow a user to assess different aspects and characteristics of the fluids and to confirm that the desired fluids are being used within the fluid injection system. A model of specific aspects of a multi-fluid fluid injection system and its impedance may also provide an indication of air in a fluid path of the fluid injection system in the event air is inadvertently moved through the fluid path because of the compressibility and ultra low viscosity of a gas compared to a liquid. Gasses are significantly compressible whereas liquids are commonly considered relatively incompressible. In an example, if during operation of the system, filling, priming, delivery of a test bolus, dose delivery, clean up, and/or preparation for next patient, the actual behavior differs from that as expected or predicted by the impedance model, the controller may assess alternative impedance models including the presence of gasses at one or more location in the system and determine if one of these models better fits the actual behavior of the system. If the presence of a gas best fits the actual behavior, then the system may take appropriate action, for example, to continue filling, burp the system, continue priming, inform the user, and/or stop the operation. Additional examples are described by Uber, et al., as set forth in WO2018/089882 which is incorporated herein by reference.

The model may also be used to assess or confirm the fluid path being used in the fluid injection system, for example, a correct syringe size, a correct catheter size, the likelihood of a pressure limiting condition, and/or a correct tubing size. If an incorrect size is detected, the operator may be alerted or the procedure may be stopped. Further, the model may be used by an injector of the fluid injection system for a self-test or diagnostic to ensure the injector is working as intended. A model may also be used to detect fluid path leaks or occlusions, the crack pressures for valves in the fluid injection system, a fluid path valve state (open, closed), and/or the presence of resonance frequencies (flow rates) to avoid such frequencies in a pulsatile pump of the fluid injection system. Based on the assessments, the system may adjust its behavior or alert the operator to a likely event or problem, for example, the likelihood of a pressure limit and delivery of a lower flow rate or volume in a given time than selected or programmed by the operator. This allows the operator to modify the program or modify or select other system components, for example contrast agents, dual flow ratios, or fluid path elements, if desired.

It is also contemplated that a model of specific aspects of a multi-fluid fluid injection system and its impedance provides the user with the ability to compensate for non-idealities in the fluid injection system. The model may allow the fluid injection system to "idealize" the fluid delivery out of the catheter to match a programmed time dependent bolus for the fluid. The model may also ensure that the actual delivery of contrast ejected from the fluid injection system is as similar as possible to the desired or programmed delivery of contrast ejected from the fluid injection system. The ability to compensate for non-idealities is also beneficial if the fluid injection system is using a bolus shape to assess flow or timing of the fluid. Creating a model of specific aspects of a multi-fluid fluid injection system and its impedance also allows the fluid injection system to work more closely to the "edge" in the terms of a rise time related to a catheter whip. It is also contemplated that a model may be used as part of a test or service calibration (standard system "load" conditions) for the fluid injection system. Several non-idealities of the fluid injection system which may be assessed and compensated for include injector head elasticity, syringe mount stiffness, a mechanical slack in a mounting and drive train of the fluid injection system, a fluid path component capacitance, variable resistance over the fluid path combined with variable viscosities of the fluid over time, stopcocks trapping fluid in a pressurized fluid path element or elements (amount being dependent upon pressure), and relief of pressure trapped in a such fluid path elements by a stopcock or high crack pressure valve.

The creation and application of a model of specific aspects of a multi-fluid fluid injection system and its impedance may be beneficial in several different situations. In one example, the model may be beneficial in arteriography, where a sharp bolus from the fluid injection system is needed. The model may also be beneficial when using a microcatheter with a small volume of fluid being delivered over a short duration. The model may be beneficial when the fluid flow may transition from laminar to turbulent flows during the delivery. The model may also be used to ensure bolus shape of fluid to heart, other organs or multiple organs at a single imaging time, are closer to the desired bolus shape of the fluid. The model may also assist in providing a more consistent bolus shape from injection to injection for dynamic imaging. The model may be used to assess if pressure limiting or some other type of performance limiting might be or is occurring and to alert the operator to the same and/or take actions to modify the injection appropriately.

The location at which the injection of fluid is assessed for accuracy may take place at several different locations. In one example, the injection accuracy may be assessed at the tissue being imaged by an imager. It is also contemplated that the injection accuracy may be assessed at another peripheral location of the patient, such as an ear lobe or finger of the patient. The injection accuracy may be assessed in the patient's central circulation system or at a catheter tip. In another example, the injection accuracy may be assessed at an entrance to the catheter or an end of a tubing set of the fluid path. It is also contemplated that the injection accuracy may be assessed by monitoring the motion or displacement along a certain length of the drive train of the fluid injection system, for example, via a potentiometer or an encoder. The motor voltage or motor current may be assessed to determine the injection accuracy. A plunger motion in the fluid injection system may be assessed to determine the injection accuracy. In another example, a motor encoder may be assessed to determine the injection accuracy. It is also contemplated that an output at the luer of a syringe of the fluid injection system may be assessed to determine the injection accuracy.

In view of this disclosure, it has also been determined that several other problems may be reduced or eliminated by the modeling and use of the overall impedance of a fluid injection system. For example, excess whip from a high acceleration of the tubing set or catheter may increase the impedance of a fluid injection system. A first hose effect (or rocket force) from high (steady state) velocity jet of fluid through the fluid injection system may affect the overall impedance of the fluid injection system. A velocity spike for the fluid in the fluid injection system that occurs during a transition from a more viscous fluid to a less vicious fluid may affect the overall impedance of the fluid injection system. A water hammer effect from inertia in the fluid injection system may be affected by the overall impedance of the fluid injection system. In another example, over pressure/velocity for an injector or any fluid path component in the fluid injection system may be affected by the overall impedance of the fluid injection system. In the event an injection lasts significantly longer than expected, the bolus may be broadened. It is also recommended that the need for injections during a characterization test may be avoided by the use of the overall impedance of the fluid injection system. It is also contemplated that undue wear or component stress induced by characterization tests or measurements may be reduced by the use of the overall impedance of the fluid injection system. System aspects that may contribute to the overall impedance of the fluid injection system include position-dependent mechanical capacitance in the fluid injection system, viscosity of the fluids in the fluid injection system changing with a change in temperature, viscosity of the fluids in the fluid injection system changing with a change in fluid (dual-flow fluid injection systems and/or flush interfaces), and differences between a laminar flow of the fluids in the fluid injection system versus a turbulent flow of the fluids in the fluid injection system.

There are many impedance aspects, or properties which may influence impedance aspects, that may be considered by the controller in the creation or use of an impedance model. Various impedance aspects may be related with various exemplary system components including for example, motor and drive train inertia, torque and speed constants, temperature, compliance or elasticity, friction, resistance, and slop or backlash. Some impedance aspects may depend linearly or non-linearly on drive train or piston aspects such as position, length, and speed. Example effects include frictional changes, bending (elasticity) and buckling. Additional impedance aspects related to mounting and seals include for example stiffness, elasticity or compliance, alignment, buckling, friction, wear, and mechanical slop. Mechanical slop or backlash may not be recoverable. The interface of the piston with the plunger and the rubber cover and the behavior of the rubber covers may be susceptible to effects, for example, from being off axis or slanted, gaps, deformation, and frictional effects, for example stiction and sliding friction behavior, with the syringe wall. The radial compression, axial deformation, and stick-slip motion of the plunger against the wall may depend upon the pressure in the syringe, the time, temperature, movement, and lubrication history. For example, plastics and elastomers may creep over time. In an example system, an axial displacement of 0.02285 inches equals 1 milliliter of fluid volume. When a piston stops forward motion, the rubber cover has some retained stress pushing proximally or reward on the piston from the sliding friction to the syringe barrel. If the piston holds its position, the rubber cover may continue to creep forward as that stress is relieved by stick-slip motion of the plunger over the barrel wall. Alternatively, if the piston relaxes at some point in time, the plunger will push backwards to relieve some of this stress, however it will not relieve all of the stress, which may be slowly relieved over time by motion and an accompanying fluid flow.

In some instances, the friction of the plunger may be lower than expected, for example due to double cycles of radiation beam sterilization or other effects. This may be something that the injector system assesses, for example, as it initially moves the plunger forward before filling or rearward during filling. For the syringe itself, a significant effect is compliance or capacitance, sometimes termed swelling, of the barrel when the contents are under pressure. In addition, the volume of swelling is a function of where the plunger is in the syringe. The farther forward the plunger is located, the lower the capacitance. In this case capacitance means the ratio of the swelling volume to the pressure difference from inside to outside. A pressure jacket may be used to reduce this capacitance despite associated complications to the relationship between volume and pressure. Some clearance must exist between the syringe and the pressure jacket so that the syringe, with reasonable dimensional tolerances, may be placed into the pressure jacket, which has its own reasonable dimensional tolerances. With a pressure jacket, the syringe can be thought of to have a multi stage swelling process. First the syringe moves forward to fully engage the pressure jacket, if it is not already so engaged. Another action is that the wall swells, and potentially moves laterally and/or axially until in fills the pressure jacket. Then the pressure jacket swells, although presumably it swells significantly less than the syringe swells, so it has a significantly lower capacitance. Additionally the syringe may bulge through any openings in the pressure jacket.

Tubing and similar fluid path elements have geometric properties such as inner diameters, outer diameters, wall thicknesses which may interact with fluid properties such as viscosity to affect resistive impedance and kinetic energy creation and storage. The geometric properties may also interact with wall material properties and temperature to affect swelling or capacitance and creep or non-elastic swelling. If multiple fluid paths are brought together, the pressure of one syringe may affect the pressure in other syringes, attenuated or delayed by the impedances of the intermediate fluid path elements and the fluids involved. There may be fluid flow due to gravity and such flow may affect the viscosity and thus impedances of the system. If there is not complete mixing when fluids come together, the fluids may remain partially or fully separate and thus impedance may be a combination of the two individual impedances. Fluid path elements such as valves may effectively separate various fluid path elements with their capacitances and other impedance properties. The closing of a valve conducting significant flow may cause an inertial pressure spike, sometimes called a "water hammer." The response time, rise and fall times, and/or linearity of operation for partially opening or linear valves may also affect the impedance mode. Viscosity changes with temperature may affect impedance properties of fluids moving in fluid path elements. There may be significant kinetic energy leaving the catheter and this may be a significant aspect of the system impedance. As viscosity or other properties change, flow in a fluid path element may change from laminar to turbulent or vice versa, which has an effect on the impedance properties of the system.

Compliance or elasticity force and volumes, as well as inertial energy or forces, may be returned or recovered at the end of the injection, for example when the fluids may bleed out of the syringes after the piston slows or stops, provided the piston is held in the stopped position and not allowed to move backwards. Other stored energy or stored volume instances may not be returned, either due to intentional system behavior or due to behavior inherent in system components. For example, when a stopcock closes and the pressure and volume are trapped in a syringe, the trapped volume may not be delivered to the patient unless the system opens the stopcock at some later point in the injection. Alternatively the system may relax the force on the piston, and the pressure in the syringe will drive that piston in a reverse direction. In this case the stored volume is effectively returned to the system and may be accounted for and used in a subsequent injection. The controller may control the way in which the force is relaxed to prevent overdrive of the piston. When the piston is pushed back to the point that it is exerting almost no force on the plunger, there may still be some capacitance retained by the rubber cover, for example because of friction with the side wall, so the pressure in the syringe will not go to zero. A similar phenomenon with a non-recovered, non-returned, or capacitive hysteresis may occur when using a rolling diaphragm syringe. A bladder syringe or other syringe with a very thin wall and minimal sliding or deforming friction will have minimal retained compliance due to plunger friction, depending upon the system design. In another example, a connector tube, commonly made from a plastic such as PVC may stretch during an injection based upon pressure, temperature, and duration of the injection. The relaxation back to its initial state may be so slow or gradual that the volume increase of the tubing is effectively never delivered to the patient. Also, because resistance through a tube is quantified as diameter to the $4^{th}$ power, this creep under pressure may significantly impact impedance in subsequent uses.

To improve and model the overall impedance of the fluid injection system several different considerations regarding the fluid injection system may be analyzed. In one example, an injector head of the fluid injection system may contain certain impedance-related properties and/or limitations that may be assessed for the overall impedance modeling of the fluid injection system. In particular, a motor inductance, resistance, and inertia of the injector head drive components may be considered. It is also contemplated that the system sensors may be elements of the fluid injection system that may be considered for improving the overall modeling of the impedance of the fluid injection system. For example, drive position sensors, force sensors, fluid element pressure sensors, and/or flow measurement sensors may contribute to the creation and use of an overall impedance of the fluid injection system and/or may be assessed to improve the overall impedance of the fluid injection system.

In another example of the present disclosure, the fluid path elements of the fluid injection system may contribute to the overall impedance of the fluid injection system and/or may be assessed to improve the overall impedance of the fluid injection system. For example, a syringe, a plunger, other pumps, tubing, valves at the syringe or downstream of the syringe, connectors (create flow velocity changes and/or restrictions), and/or IV catheters may contribute to the overall impedance modeling of the fluid injection system and/or may be assessed to improve the overall impedance of the fluid injection system. The impedance of a fluid path element may also be assessed in connection with the overall impedance of the fluid injection system. Elasticity (whether position dependent or non-linear) of the fluid path elements may contribute to the overall impedance of the fluid injection system and may be assessed to improve the overall impedance. It is also contemplated that a change in resistance of the fluid path elements due to a change in pressure of the fluid resulting in tube swelling may contribute to the overall impedance of the fluid injection system and may be assessed to improve the overall impedance modeling. Such swelling for example may be time and pressure dependent and only very slowly if at all return to the original shape. Swelling over time or over subsequent injections may affect the system performance if not accounted for in the impedance model. Stopcocks and/or check valves in the fluid path elements may contribute to the overall impedance of the fluid injection system and may be assessed to improve the overall impedance modeling. In another example, nodes or connections for mixing or separating fluids in the fluid path elements may contribute to the overall impedance of the fluid injection system and may be assessed to improve the overall impedance modeling. The cross-sectional shape and size of the fluid path elements, a fluid velocity through the fluid path elements, and/or a type of flow through the fluid path elements may contribute to the overall impedance of the fluid injection system and may be assessed to improve the overall impedance modeling. A total volume of the fluid path elements may contribute to the overall impedance of the fluid injection system and may be assessed to improve the overall impedance modeling. Fluid path element limitations, such as a maximum pressure or flow moving through the fluid path element, may contribute to the overall impedance of the fluid injection system and may be assessed to improve the overall impedance modeling. The sources of fluid to the fluid path elements, such as fluid bottles, bags, or containers, may contribute to the overall impedance of the fluid injection system and may be assessed to improve the overall impedance modeling.

It has also been considered that properties of the fluid injection system may contribute to the overall impedance of the fluid injection system and may be assessed to improve the overall impedance modeling. In one example, the viscosity of the different fluids (for example, contrast, saline, air) moving through the fluid injection system may contribute to the overall impedance of the fluid injection system and may be assessed to improve the overall impedance modeling. An effect of temperature on the viscosity of the fluid(s) moved through the fluid injection system may contribute to the overall impedance of the fluid injection system and may be assessed to improve the overall impedance modeling. The compressibility of the fluid(s) moved through the fluid injection system may contribute to the overall impedance of the fluid injection system and may be assessed to improve the overall impedance modeling. In another example, the existence of multiple phases (for example, multiple liquids or gas) of a fluid in the fluid injection system may contribute to the overall impedance of the fluid injection system and may be assessed to improve the overall impedance modeling. The fluid mass, including inertia or inertance, of the fluid(s) being moved through the fluid injection system may contribute to the overall impedance of the fluid injection system and may be assessed to improve the overall impedance modeling.

It is has been considered that several different non-idealities or circumstances may affect the overall impedance of the fluid injection system. It is contemplated that these non-idealities or circumstances may be taken into account or consideration when assessing the overall impedance of the delivery fluid system and improving the overall impedance modeling of the delivery fluid system. As discussed above in this disclosure, capacitance is a contributing factor to the overall impedance of the fluid injection system. The capacitance of the fluid injection system may be affected by the volume and pressure of the fluid(s) moving through the fluid injection system. Capacitance of the fluid injection system may also be affected by the plunger position within the fluid injection system. It is also contemplated that the capacitance may be affected by the history of the fluid injection system, such as previous swelling of the tubing set or hysteresis. Capacitance of the fluid injection system may also be affected by the temperature of the fluid(s) moving through the fluid injection system or the temperature of the fluid path components in the fluid injection system. Temperature may also affect the rate of swelling of various fluid path elements.

Additional non-idealities or circumstances other than system capacitance may affect the overall impedance of the fluid injection system. For example, flow resistance of the fluid(s) in the fluid injection system, including flow rate and pressure, may contribute to the overall impedance of the fluid injection system and may be assessed to improve the overall impedance modeling. The flow resistance of the fluid may depend on the history of usage of the fluid path tubing in the fluid injection system, which can create tube swelling or hysteresis. The flow resistance may also depend on the temperature of the fluid(s) moving through the fluid injection system and/or the temperature of the fluid path elements in the fluid injection system. A change in diameter of the fluid path elements, for example from swelling, may also affect the flow resistance of the fluid(s). The transition of fluid flow from laminar flow to turbulent flow in the fluid injection system may contribute to the overall impedance of the fluid injection system and may be assessed to improve the overall impedance modeling. This may be affected by fluid path transitions. In another example, a pressure drop due to a change in the type of flow (laminar v. turbulent) of the fluid(s) may contribute to the overall impedance of the fluid injection system and may be assessed to improve the overall impedance modeling. It is also contemplated that acceleration and/or deceleration of the fluid(s) in the fluid injection system may contribute to the overall impedance of the fluid injection system and may be assessed to improve the overall impedance modeling. Conditions or operational states of high-crack pressure valves, check valves, stopcocks, and/or mixing chambers in the fluid injection system may contribute to the overall impedance of the fluid injection system and may be assessed to improve the overall impedance modeling.

It is also contemplated that the overall impedance may be assessed and improved along the entire fluid flow path of the fluid(s) through the fluid injection system, not just as discrete, separate portions of the fluid flow path. In one example, the entire fluid injection system from injector to output of the syringe(s) to the output of the catheter may contribute to the overall impedance of the fluid injection system and may be assessed to improve the overall impedance modeling. In a second example, sections of the fluid injection system may be modeled as discrete elements and others as continuous or multiple elements. In another example, viscosity propagation of the fluid(s) in the fluid injection system and the anticipated effects of the viscosity propagation may contribute to the overall impedance of the fluid injection system and may be assessed to improve the overall impedance modeling. The flow front of the fluid(s) and/or the interfaces or mixing zones of the fluids in the fluid injection system may also be assessed when considering overall impedance of the fluid injection system. The flow front of the fluid(s) is directed to the fluid interaction between fluids with different viscosities that meet one another and move through the fluid injection system. The temperature and/or temperature changes in the fluid(s) moving through the fluid injection system may contribute to the overall impedance of the fluid injection system and may be assessed to improve the overall impedance modeling. It is also contemplated that the catheter size (either input by the user or estimated from a test injection or some part of the injection itself) may contribute to the overall impedance of the fluid injection system and may be assessed to improve the overall impedance modeling. Limitations of the injector head may contribute to the overall impedance of the fluid injection system and may be assessed to improve the overall impedance modeling. Sensor limitations in the fluid injection system may contribute to effective measurement of the overall impedance of the fluid injection system and may be assessed to improve the overall impedance modeling. For example, sensor response speed and measurement of non-idealities in the fluid injection system be assessed and accounted for to improve the overall impedance modeling. It is also contemplated that the bulk modulus of the fluid(s) in the fluid injection system may contribute to the overall impedance of the fluid injection system and may be assessed to improve the overall impedance modeling. For example, saline compresses more when a greater volume of air is dissolved in the saline in the fluid injection system. The patient's blood pressure and viscosity may contribute to the overall impedance of the fluid injection system and may be assessed to improve the overall impedance modeling. In another example, the properties of the motor, for example inertia, controller, and/or piston in the fluid injection system may contribute to the overall impedance of the fluid injection system and may be assessed to improve the overall impedance.

It has also been contemplated that there are several different opportunities or stages during the setup and operation at which to assess the overall impedance and/or improve the overall impedance modeling of the fluid injection system. In one example, the overall impedance of the fluid injection system may be assessed when planning to fill the fluid(s) into the fluid injection system and/or during the filling of fluid(s) into the fluid injection system. The overall impedance of the fluid injection system may be assessed when planning the delivery of the fluid(s) through the fluid injection system to the patient. In another example, the overall impedance of the fluid injection system may be assessed after or during use of a test bolus in the fluid injection system. It is also contemplated that the overall impedance of the fluid injection system may be assessed during delivery of the fluid(s) from the fluid injection system. Feedback and/or a servo on one or more variables of or related to the overall impedance may be supplied to a control system during delivery of the fluid(s). It is also contemplated that anticipated changes in the fluid injection system may be taken into account during delivery of the fluid(s). In another example, the overall impedance of the fluid injection system may be assessed during delivery, during which the performance of the fluid injection system is assessed to determine when the performance is within an anticipated performance range. In another example, the impedance model may be assessed and modified after one injection for use during a subsequent injection. In another example, the overall impedance of the fluid injection system may be assessed during manufacturing of the fluid injection system and its separate components. It is also contemplated that the overall impedance of the fluid injection system may be assessed continuously to indicate when service might be needed, during service of the fluid injection system and/or during a calibration process of the fluid injection system. In another example, the overall impedance of the fluid injection system may be assessed when each new disposable set or each prime, fill, or other operation of the disposable set is performed. It is also contemplated the overall impedance of the fluid injection system may be assessed in real time. The estimates of the overall impedance factors and contributors may be linearized to develop compensation factors in real time for comparison with desired conditions for the fluid injection system to ensure adequate overall impedance modeling, safety, and/or fluid delivery performance. In a further example, the overall impedance of the fluid injection system may be assessed by using the control system of the fluid injection system to plan piston movements of the injector before injection and then adjust the piston movements in relation to that plan in real time during the injection.

To assess and improve the overall impedance modeling of the fluid injection system there are several different methods and techniques for characterizing the fluid injection system to determine how the overall impedance modeling can be improved. The characteristics or conditions of the fluid injection system may be derived from the initial design of the fluid injection system, the specifications of the fluid injection system, the manufacture of the fluid injection system, and/or the pretest conditions of the fluid injection system. In another example, calibrations or various characterizations of the system may be conducted to ensure real-time accuracy of the characteristics of the fluid injection system.

In another example, a test bolus of saline (or contrast or both saline and contrast) may be used to characterize the fluid injection system. It is also contemplated that the resistive and capacitive components of impedance may be computed from an initial ramp-up to determine the fluid injection system characteristics. The pressure of the fluid injection system may be measured without friction from the non-moving/non-delivering saline/contrast syringe. In another example, the friction effect may be corrected in an assessment of pressure via a non-moving syringe. It is also contemplated that various input test functions may be used for the fluid injection system identification, including impulse, step (bolus), ramp, white noise, and colored noise, among other input test functions. In another example, an ultrasonic detector may be used when air is flowing through the fluid injection system, or when fluid(s) is flowing through the fluid injection system to characterize the fluid injection system. The density and viscosity of the fluid(s) may also be used to characterize the fluid injection system.

In another example, a downstream flow sensor of floats or other indicators that move in the fluid injection system may be used to characterize the fluid injection system. It is also contemplated that a disposable flow meter that measures pressure drops in the fluid injection system may be used to characterize the fluid injection system. An image recognition system or the monitoring of sensor features in the fluid injection system may also be used to characterize the fluid injection system. In another example, a plurality of floats or other indicators having different densities may be used to sense viscosity/density changes in the fluid(s), allowing the fluid injection system to compensate for the viscosity/density changes. In another example, a sound sensing element may be used to detect vibrational movement of floats or other indicators that float in the fluid(s) of the fluid injection system. It is also contemplated that the system impedance may be characterized in open and/or closed (short-circuit) conditions using, for example, pinch valves or stopcocks. In another example, the system impedance may be characterized under variable load conditions at system output. Resonant sensors may be used to measure fluid viscosity to characterize the system impedance. In another example, magnetically sense or responsive floats or other indicators may be used to sense a viscosity of the fluid(s) in the fluid injection system to characterize the system impedance. In another example, two pressure transducers and a known flow restrictor may be used to characterize the system impedance. It is also contemplated that many different flow sensor arrangements may be used to characterize the system impedance.

It has also been determined that there are many different locations at which aspects of the system impedance may be measured or characterized. For example, aspects of the system impedance may be measured in a tube set wall and/or a syringe barrel wall. A swell or pressure reading in the tube set wall and/or syringe barrel wall may be used to characterize the system impedance. Stress or swelling in a featured section of the fluid injection system may also be used to characterize the system impedance. In another example, the system impedance may be characterized or measured at a motor control arrangement of the fluid injection system. A speed, current, and/or torque of the motor control arrangement may be measured. It is also contemplated that strain gauges may be used at different locations in the fluid injection system to characterize the system impedance. The system impedance may also be measured with a pressure-sensing tube located at the neck of at least one syringe in the fluid injection system. In the event a certain overall system capacitance is desired, there are several different methods available for achieving the desired overall system capacitance. In one example, certain movements of the contrast piston in the fluid injection system may improve the system impedance. In another example, certain movements of the saline piston in the fluid injection system may improve the system impedance. It is also contemplated that stopcocks in the fluid injection system may be opened and/or closed to improve the system impedance. In another example, at least one of the pistons in the fluid injection system may be moved farther than is typically done so that an added volume of fluid is supplied to the system to compensate for trapped fluid when a stopcock is closed. In another example, one of the syringes in the fluid injection system may be moved or pulled back a certain predetermined distance from the other syringe to reduce the height of the peak pressure or flow through the fluid injection system. In another example, the stopcocks may be opened at a relatively slow rate to adjust pressure rises in the fluid injection system. Analog stopcocks or variable restriction valves may be used in one example. It is also contemplated that the motor arrangement of the fluid injection system may be pulsed and strategically held to ensure the flow passes efficiently and as desired through the fluid injection system.

In another example to obtain a desired system impedance or system behavior or response, the fluid(s) in the fluid injection system may be pre-pressurized before allowing the fluid(s) to flow through the fluid injection system to ensure consistent pressures are experienced throughout the fluid injection system. Pressure in the fluid injection system may also be relieved to obtain a desired fluid injection system pressure. It is also contemplated that the capacitance of the fluid injection system may be minimized to improve the system impedance modeling. It is also contemplated that a specific zero (start) position for the barrel and/or motor arrangement of the fluid injection system may be adjusted. A pressure dependent zero position may also be established to account for rubber cover deformation and syringe movement in the fluid injection system. It is also contemplated that the syringe(s) are only filled with the specific volume of fluid(s) needed for the current protocol to minimize the capacitance at an injection end of the fluid injection system. It is also contemplated that the fluid(s) already in the tube set of the fluid injection system may be taken into account and a rise time of the pressure may be adjusted at the beginning of the injection process to account for the fluid(s) already present in the tube set.

In other examples, a dual or multiple lumen fluid path extending most or all of the way to the patient connection of the fluid injection system may be used to improve the system impedance. It is also contemplated that a smaller lumen on a saline line may be used so the saline line pressure drop is equal to the contrast line. A hydraulic accumulator may also be used in the fluid injection system to control the fluid pressure in the fluid injection system. In another example, analog sensing or servo arrangements may be used in the fluid injection system to reduce time delays between transitions in the fluid injection system.

In other examples, the viscosity of the fluids in the fluid injection system may be matched or more closely matched to reduce the capacitance in the fluid injection system. Heating of one of the fluids may be used to match or more closely match the fluid viscosities. It is also contemplated that a high viscosity flush (or a low viscosity contrast) may be used to reduce the pressure and thus the effect of the capacitance in the fluid injection system. In another example, the contrast may be diluted to decrease the viscosity of the contrast in the fluid injection system. Intermediate mix ratios of the fluids in the fluid injection system may be used to broaden the transition of the fluid through the fluid injection system, thus broadening the change in impedance. In another example, an active and/or controlled clamp on the tubing of the fluid injection system may be used to control the impedance of the fluid injection system. An adjustable restrictor may also be provided at the patient end of the fluid injection system to control the impedance of the fluid injection system.

When attempting to improve the system impedance and impedance modeling of the fluid injection system there are several different limitations to take into consideration. Characteristics of the system components, such as the pressure of fluid path elements and motor current, may be limitations to consider for the system impedance. It is also contemplated that environmental factors may affect the system impedance, such as temperature, noise, vibration, system orientation with respect to gravity, and/or height effects on a pressure head if sensing pressure downstream in the fluid injection system. Variations in system drive and syringe plunger friction (both static and dynamic) may provide limitations on the system impedance consistency and modeling. Variations in fluid system components' elasticity and/or capacitance may provide limitations on or require more sophisticated or involved modeling of the system impedance. For example the dynamic coefficient of friction of the plunger against the syringe barrel may depend upon the pressure of the fluid in the syringe. Similarly, the capacitance of the syringe depends upon plunger position. In general, impedances may not be constant but depend upon one or more variables that are changing as the system delivers the desired fluids to the patients. In another example, drive system inertia (which may limit start/stop ramp time) may provide limitations on the system impedance consistency and modeling.

It is contemplated, based on the limitations discussed above, that there are several different locations/components that may be used in the fluid injection system to improve the system impedance. For example, pressure jackets on the syringe(s), high crack pressure valves, hydraulic compensators, a separate syringe motor, and/or contrast syringe at the patient pushed with a second saline syringe may be used to improve the system impedance and impedance modeling. It is also contemplated that check valves, high crack pressure valves, and/or expansion sections in the fluid path of the fluid injection system may be used to improve the system impedance modeling. Fluid selection and treatment of the fluid(s) in the fluid injection system may be used to improve the system impedance modeling. For example, fluids with similar viscosities and/or multiple viscosities may be used in the fluid injection system.

It is also contemplated that several different system modeling options may be used to model and/or assess the system impedance. For example, linear and/or non-linear system modeling may be used to assess the system impedance. Continuous and/or discrete system modeling may be used to assess the system impedance. Parametric and/or non-parametric system modeling may be used to assess the system impedance. Time and/or frequency domain system modeling may be used to assess the system impedance. Deterministic and/or stochastic system modeling may be used to assess the system impedance. In another example, distributed and/or lumped parameter system modeling may be used to assess the system impedance. When modeling the system impedance, selection of system aspects to consider in the model, based on importance, impact, knowability, and/or practicality, may be used to assess the system impedance. A model of behavior may be developed by accounting for system aspects that are unknown or unknowable, for example, through test, experimentation, and/or approximation and confirmation. A model may be adjusted to a particular instance of the fluid injection system or a fluid injection system used in a particular case. A program fluid system action may be created by taking the model into consideration. A program may be executed that compares actual results to expectations from the model and the model may be adjusted or acted on appropriately. The model may also be optionally updated at various times before, during, and/or after a specific injection program or sequence.

Figure 36:
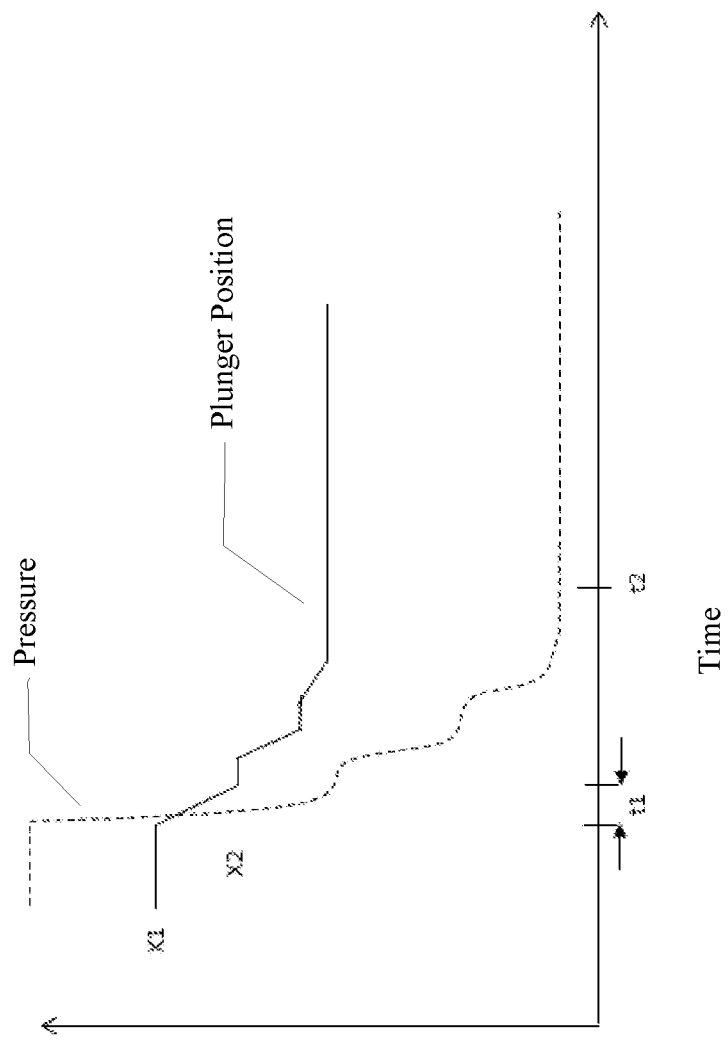
FIG. 36 is a graphical illustration of a pressure relief method used in a fluid injection system according to another example of the present disclosure.

With reference to FIG. 36, according to another example of the present disclosure, a method of improving the overall performance of the fluid injection system is described. This method may include relieving pressure built up in the syringes of the fluid injection system after an injection, either immediately at the end of the desired injection or at some time later if the syringes are isolated in some way, for example, by a stopcock or a high crack pressure valve. By using this method, the pressure in the system may be relieved via the system itself rather than being pushed into the bulk fluid container(s) of the system, and/or remaining in the disposables and tube sets of the system. To effectuate the method, several inputs are provided to the control system of the fluid injection system, which are used to relieve pressure from the system based on the input conditions. In one example, t1 corresponds to the amount of time that the motor arrangement of the fluid delivery system will be powered off. t1 may change from motion to motion of the motor. t2 is the maximum amount of time a pressure relief algorithm is allowed to repeat. These times may be entered into the control system or may be determined by the control system based upon the relevant system impedance parameters. It is contemplated in one example of the present disclosure that the pressure relief method may be conducted at the end of an injection process of the fluid injection system. It may occur immediately after the end of the injection, or as the injection ends.

In one example, the method may include ending an injection process of the fluid injection system and leaving a piston at a first position, X1. Power may then be removed from the motor arrangement of the fluid injection system for a predetermined period of time, t1. When the power is removed from the motor arrangement, the built-up pressure in the fluid injection system pushes the plunger/piston assembly toward a bottom (distal) end of the syringe(s) in the fluid injection system, which may move the motor arrangement in reverse, thereby building up some rotational kinetic energy in the motor. After the predetermined period of time, t1 has passed, power is again supplied to the motor arrangement of the system. At this time, the position of the piston/plunger assembly in the syringe is recorded, X2. In the event there is a position displacement of the piston/plunger assembly in the syringe during power removal, X2-X1>0, power is again removed from the motor arrangement and the above-described process is repeated. Each time the process is repeated the post-power supply position reading (for example, X2) is recorded as the new initial position of the piston/plunger assembly (for example, X1). In one example, the pressure relief method is stopped when there is no further movement of the piston/plunger assembly when power is removed from the motor arrangement. In another example, the pressure relief method is stopped when the predetermined pressure relief algorithm time period, t2, has expired. A benefit of use of a relatively short t1 and/or allowing the pressure relief motion to occur in steps or stages is that it reduces the energy that is transferred from the impedance of the syringe into the inertial component of the impedance of the motor and drive train as rotational kinetic energy. In some instances, when t1 is relatively long, the motor and/or drive train may build up sufficient kinetic energy related to its inertia that it continues to move backward, rearward, or distally even though the pressure in the syringe is at zero. In some instances, this inertial energy stored in the impedance of the motor may create a negative pressure or vacuum in the syringe that could result in the aspiration of blood from the patient or unanticipated fluid from the fluid reservoir. In some instances this over-travel in the reverse direction may induce mechanical slop or other impedance complications into the system and power may be needed to be applied in order to stop such movements.

The pressure relief method discussed above is advantageous for fluid injection systems in which pressure held within the system cannot be dissipated due to particular fluid path elements used in the system. For example, in certain fluid injection systems, pressure may be trapped within stopcock valves in the syringe(s). It is also contemplated that there are alternative pressure relief methods that may be used. For example, a compliance-based movement of the piston/plunger assembly may be used to relieve a known amount of pressure from the system. In the event the compliance of at least a portion of the fluid injection system is known, the pressure relief method may be used to relieve a predetermined amount of pressure based on the compliance of the at least one portion of the system. In another example of the method, instead of conducting the pressure relief method for a maximum predetermined time period, t2, the pressure relief method is conducted until a strain gauge positioned in the system reads a desired pressure for the system. In another example, the forward force of the motor may be gradually reduced over a specific time so that the reverse rotation speed is kept within a desired range.

The designation of first fluid, second fluid, third fluid and so on is for reference and understanding only. Generally the system is loaded with one or more fluids in an arbitrary order. During loading, the fluid path is generally filled with saline first to remove air because it is cheaper and less messy than contrast. There may also be a test injection to check patency. This may be done with contrast or saline, so the fluid in the various fluid path elements distal to the confluence or joining of the fluid flows may differ depending upon the fluid flows and injections that have happened prior to that point. Also, the injection may start with any of the fluids and any of the other fluids may follow in an order dictated by the procedure, not position or number. In one example, the injection system assesses and stores these flow properties so that it can use the correct fluid physical properties in its model of how the fluid path will respond to a particular drive motion, and thus adjust drive motions to achieve the desired fluid outputs.

In the hydraulics discipline, which is directed to the flow of fluids, it is well known to consider various significant aspects of total system impedance in analysis of fluid flow and system performance with various models. For example, there may be either a discrete or lumped parameter model or one utilizing continuous equations such as the Navier Stokes equation. Hybrid models may also be used. However, in most hydraulic systems, only a single fluid is utilized. In the devices, systems, and method of the present disclosure, two or more fluids are considered with one or more significant differences in their fluid properties. This occurs in some medical fluid injection systems when two liquids of different viscosities are delivered and/or when the presence of air is assessed throughout the medical fluid injection system.

Relating Pressure to Flow Rate by Hydraulic Resistance—Introduction and Description of Variables The following equations enable the various methods of modeling, assessing, predicting, utilizing and/or controlling the impedance of a fluid injection system as set forth throughout this disclosure. It is important to use consistent units when describing fluid flow with mathematical relationships. Subscripts are used with the variables to identify them and are defined in the table below.

TABLE 2

| Subscript | Definition |
| --- | --- |
| i | time[second] |
| j | Subscript j is not a number but is a qualitative variable that identifies a component or system or components. For example, j = A refers to syringe A. Subscript j may also be more descriptive. For example, j = TOTAL describes a sum of two other variables such as $\dot{Q}_{TOTAL,i} = \dot{Q}_{A,i} + \dot{Q}_{B,i}$ where $\dot{Q}_{TOTAL,i}$ is the sum of flow rates out of syringes A and B at time = i. If a variable is not present for j, then the variable is common to one or more components. An example is pressure at time i given as $P_i$ that is common to multiple syringes that are not isolated with a valve. |

Pressure $P_i$ in a syringe is the product of volume flow rate $\dot{Q}_{TOTAL,i}$ out of that syringe, and total resistance $R_{TOTAL,i}$ to the flow rate at time i. Variables are defined with Equation 1 in consistent, English, units:

$$P_i \left[ \frac{pound - force}{inch^2} \right] = R_{TOTAL,i} \left[ \frac{pound - force - second}{inch^5} \right] \dot{Q}_{TOTAL,i} \left[ \frac{inch^3}{second} \right]. \quad \text{(Equation 1)}$$

Methods of Describing the Pressure-Resistance-Flow Rate Relationship

The relationship shown in Equation 1 is often determined empirically for a given system where pressure is typically plotted versus flow rate. Some of these plots are modified for particular disciplines. For example, industries that utilize pipes (for example, gas pipelines) present pressure loss per length of pipe as a function of flow rate with separate curves for each diameter and fluid combination.

Many references present data that show a local relationship between pressure and flow rate of fluid passing through a particular geometric feature such as an orifice or pipe bend. Hydraulic resistance can be calculated at any point on the plot by the ratio of pressure to flow rate. Density of the fluid is a factor for local descriptions of pressure depending on flow rate.

Hydraulic resistance can also be calculated using several factors. All factors for calculating hydraulic resistance $R_{TOTAL,i}$ in the work described in this disclosure are both outside and downstream of the syringe volume. Pressure $P_i$ is assumed constant throughout the syringe volume but varies along the fluid path in the tubing and catheter. Variation of pressure in the tubing and catheter will not be discussed in detail in this disclosure because the total sum of hydraulic resistances can be used here without influence on the results. If individual hydraulic resistance factors change fluid mixing such that the fluid delivery response is measurably influenced then those individual effects must be quantified in the calculations presented.

Geometric factors influencing calculations for hydraulic resistance to fluid flow $R_{TOTAL,i}$ include length, curvature, and inner diameter of both the tubing and catheter. Properties of fluids including density, bulk modulus, and viscosity are additional variables for calculating hydraulic resistance.

Mass Flow Versus Volume Flow

Volume flow rate $\dot{Q}_{j,i}$ can also be defined using mass instead of volume and is given as $\dot{Q}_{M,j,i}$. Mass flow rate is necessary for gaseous fluids because increasing pressure measurably reduces volume of a gas.

Pure liquid fluids are not measurably reduced in volume until pressure exceeds 145,000 psig (1 GPa). Liquids often contain air that significantly reduces pressure required to significantly change the volume. Liquid fluids with entrained, mixed, or adsorbed air are more accurately modeled by accounting for the volume change due to pressure. Accounting for air in liquids will be discussed later but most of the work described here uses volume flow rate with $$\text{units} \left[\frac{inch^3}{second}\right].$$

Hydraulic Resistance

There are multiple mechanisms for hydraulic resistance. Below are two mechanisms that are common for tubing and catheters.

Hydraulic resistance due to laminar, viscous, flow in circular cross-sections like the tubing or catheter is the first mechanism and is given in Equation 2 as $R_{viscous}$:

$$R_{viscous}\left[\frac{pound-force-second}{inch^5}\right] = \frac{128\mu\left[\frac{pound-force-second}{inch^2}\right]L[inch]}{\pi\varnothing^4[inch^4]} \quad \text{(Equation 2)}$$

where $$\mu\left[\frac{pound-force-second}{inch^2}\right]$$

is the absolute viscosity, and $L$ [inch] and $\varnothing$ [inch] are the length and diameter, respectively, of the conduit for fluid flow. Note that diameter $\varnothing$ is raised to the fourth power in Equation 2 and is very influential.

Local flow restrictions include the opening of a catheter or entrance to the tubing connector at the end of the syringe. Equation 3 calculates the second mechanism of hydraulic resistance $R_{density}$ that is related to density $$\rho\left[\frac{pound-force-second^2}{inch^4}\right],$$

diameter $\varnothing$ [inch], and flow rate $$\dot{Q}\left[\frac{inch^3}{second}\right]:$$

$$R_{density}\left[\frac{pound-force-second}{inch^5}\right] = \frac{8\rho\left[\frac{pound-force-second^2}{inch^4}\right]}{\pi^2\varnothing^4[inch^4](Constant)^2}\dot{Q}_{TOTAL,i}\left[\frac{inch^3}{second}\right]. \quad \text{(Equation 3)}$$

The Constant is related to local geometry details. Note that $R_{density}$ is a function of flow rate $\dot{Q}_{TOTAL,i}$ resulting in a non-linear relationship between pressure and flow rate.

Increasing density, viscosity, length of conduit, and severity of the local restriction all increase hydraulic resistance. Decreasing flow conduit diameter exponentially increases flow resistance. Pressure required for a given flow rate increases with resistance due to the mechanical to thermal energy transformation that results in pressure loss along the fluid path.

Finite element computational fluid dynamic (CFD) methods can be extended to the fluid components in order to characterize hydraulic resistance. Techniques include smoothed particle hydrodynamics (SPH), Combined Lagrangian Eulerian (CLE), and Euler and Lagrangian methods. Specific modelling considerations to the finite element discretization must be used to implement such methods in an injector with limited computational ability. Benefits to flow rate control are realized with CFD when hydraulic resistance is hyper sensitive to variation in nominal values for variables such as the actual size of a catheter with a relatively small diameter and mixing of two different fluids requires discretization only possible with such numerical methods.

Mixed Fluids and Hydraulic Resistance

Mixed fluids have properties that are calculated by the characteristics of mixing. Homogeneous mixing may yield property values proportional to the ratio of the mixture. For example, a homogeneous mixture of contrast and saline that is 40% contrast by volume will have a mixed density $\rho_{mix}$ is given by Equation 4:

$$\rho_{mix}=0.4\rho_{contrast}+(1-0.4)\rho_{saline} \quad \text{(Equation 4)}.$$

Some mixture representative volumes must be determined with respect to the specific characteristics of the mixed volume. An example is a reported phenomenon of catheters that have 100% contrast followed by 100% saline in a multiphase injection. At the start of the saline injection there is a period of time that the saline flows inside of an annular, conical, volume of contrast; the annular volume of contrast decreases with time until flow is 100% saline. Mixed viscosity $$\mu_{mix}\left[\frac{pound-force-second}{inch^2}\right]$$

will likely be determined empirically with experiments because determining $\mu_{mix}$ with calculations like those of computational fluid dynamics may not be practical since a microscopic scale model is required. The annular volume phenomena described above has potential to occur in both the tubing and catheter.

Total Hydraulic Resistance

Total hydraulic resistance $R_{TOTAL,i}$ in the entire system using the examples above is quantified in Equation 5 by $$R_{total,i} = \sum_{j=1}^{n} \frac{128\mu_j\left[\frac{pound-force-second}{inch^2}\right]L_j[inch]}{\pi\phi_j^4[inch^4]} + $$

$$\dot{Q}_{TOTAL,i}\left[\frac{inch^3}{second}\right]\sum_{k=1}^{m}\frac{8\rho_k\left[\frac{pound-force-second^2}{inch^4}\right]}{\pi^2\phi_k^4[inch^4](Constant)^2} +$$

Additional Terms.

For many injector configurations n=2 for viscous resistances and m=1 for local, density, resistance is adequate.

Additional terms accounting for different geometry, turbulent flow, etc. can be added to $R_{TOTAL,i}$ as appropriate. Equations for hydraulic resistance demonstrate that changes to viscosity, density, and inner diameter result in change to flow rate and/or pressure are implicit i.e., they occur without respect to time. Such changes occur by opening or closing a valve or suddenly injecting a different liquid with an additional syringe that is connected to the fluid path of the first syringe. Nearly instantaneous changes in flow rate occur without modification to the velocity of the piston or pistons displacing the fluid or fluids. Pressure is not instantaneously changed in typical radiology applications for reasons that will be described later.

Note that $R_{TOTAL,i}$ can be simplified as $$R_{TOTAL,i} = R_0 + R_1\dot{Q}_{TOTAL,i} \quad \text{(Equation 6)}.$$

This equation format will be of use in solving for $\dot{Q}_{total,i}$.

Fluid-Structure Interaction of Mechanical Parts and Fluids—Rigid Mechanical Parts If an injector piston in a syringe labeled j with a plunger of cross-sectional area $A_{0j,i}$ [inches²] like that in FIG. 2 moves an amount $\Delta y_{j,i}$ [inches] in time increment i then the volume of fluid theoretically displaced by the piston equals the volume of fluid injected at rate $\dot{Q}_{j,i}$ and is related to pressure $P_i$ and $R_{TOTAL,i}$ through the Equation 1 and Equation 7 below:

$$A_{0j,i}\frac{\Delta y_{j,i}}{\Delta t}\left[\frac{inch^3}{second}\right] = \quad \text{(Equation 7)}$$

-continued $$\dot{Q}_{j,i}\left[\frac{inch^3}{second}\right] = \frac{P_i\left[\frac{pound-force}{inch^2}\right]}{R_{TOTAL,i}\left[\frac{pound-force-second}{inch^5}\right]}$$

Subscript 0 for cross-sectional area $A_{0j,i}$ represents area of both the plunger and syringe at zero pressure. Area $A_{0j,i}$ is not the total surface area of the plunger but rather the projected area that is perpendicular to the syringe axis of motion.

Equation 7 above reflects that none of the mechanical parts are elastic and do not deform when subjected to forces associated with pressure or acceleration of the fluids. Volume displacement of the plunger equals volume of fluid expelled from syringe j and injected. As material stiffness, assembly precision, and section size increase, actual response of a real system can approach that of the theoretical system.

Another valid application for Equation 7 occurs when elastic components do not undergo a change in their current state of deformation because pressure and other sources of energy are constant. Equation 7 is valid during a steady state for pressure $P_{STEADY\ STATE}$ and flow rate $\dot{Q}_{j,STEADY\ STATE}$ such that volume displaced by $\Delta y_{j,i}$ is equal to volume injected at rate $\dot{Q}_{j,i}$.

Steady state flow rate $\dot{Q}_{j,STEADY\ STATE}$ is equal to $$A_{j,i-\Delta t}\frac{\Delta y_{j,i}}{\Delta t}.$$

Note that the subscripts for cross-sectional area $A_{j,i-\Delta t}$ do not have a zero. The reason is that the inner diameter of the syringe and plunger diameter are elastic and vary with pressure. Magnitude of the area variation is on the order of 1.0%. Also note that the area used for flow rate at time i is the area at time i−Δt to account for the pressure variation due to the pressure resulting from volume displacement.

Elasticity in Structural Parts and Fluids

Contemporary injectors used for radiology are made with many thermoplastic and thermoset polymer parts that are linear-elastic, flex under load, and have assembly clearances that measurably influence actual flow rate. Polymer rubber parts that are hyper-elastic are also part of the typical assembly, have stiffness significantly lower than many thermoplastic polymers, and further influence the real injection rate by orders of magnitude.

Polymers relax and deform under load given enough time. Many polymers used in radiology applications relax and deform in elapsed time that is of short duration. Time-dependence of materials influences their performance during injection.

Polymers have a relatively high coefficient of thermal expansion as compared to that of other materials. Increasing thermal gradients consequently increase variation of component size and sometimes shape such that the change can influence fluid delivery results. Thermal effects can be quantified so that compensation is feasible during injection.

Mechanical properties are a function of temperature. In general, stiffness and strength both decrease with temperature. Compensation for mechanical property variation is possible if the temperature-property relationship is characterized and part of the injector algorithm.

Knowledge of the temperature is required for compensation for both dimensional change and property variation.

Heat sources are often part of the injector system and have the greatest potential to induce elastic thermal effects.

Plasticity in Structural Parts

Some syringe components like the rolling diaphragm illustrated in FIG. 4 may deform permanently with plastic deformation. Appropriate relationships for plastic strain must be used in algorithms used to for fluid delivery using components that tolerate plastic deformation.

Hydraulic Capacitance Due to Elasticity

Pressure change during delivery of fluid changes potential, elastic, and strain energy of the system. Increasing pressure increases overall internal volume of system components and/or compressive forces on system components resulting in their contraction, as discussed herein.

Kinetic energy of pressurized, flowing, fluid further affects overall performance of the fluid delivery system. For example, inertial forces of moving contrast material and elastic expansion of the structural parts, containers, and/or tubing and catheter associated with the system may cause a lag or time delay between movement of the syringe piston within the injector and proportional movement of contrast or saline material out of the catheter and into the patient.

Mass of the fluid is always conserved and at the pressure range used in radiology volume of fluid is conserved as long as air is not contained in the fluid. Lag is only relative to the desired output; fluid is just moving in an area where it shouldn't flow and/or not moving at the desired velocity.

As injection pressure increases, fluid fills any extra_capacity created by dilation or compression of various components of the fluid delivery system such as the syringes, tubing connected to the patient, and components of the fluid injector. Maximum pressure is on the order of 1,200 psig for some angiographic procedures. Volume of this capacity of fluid in both the syringe and tubing subtracts from the desired quantity to be delivered in the injection procedure until conditions including pressure are such that flow out of the capacity is favorable. Such increase in the quantity of fluid in capacity occurs due to system hydraulic capacitance $$C_{h,TOTAL,i}\left[\frac{inches^5}{pound-force}\right].$$

If one or more of the treatment fluids contains or accumulates air that is entrained, mixed, or adsorbed, then the fluid bulk modulus $$\beta_{j,i}\left[\frac{pound-force}{inches^2}\right]$$

may be decreased such that changes in treatment pressure measurably change the fluid volume due to increased capacitance.

Capacitance Variables

Hydraulic capacitance $C_{h,j,i}$ (also referred to as compliance or elasticity) is the product of a volume j at zero pressure and time i labeled $V_{0j,i}$ [inches$^3$] and the effective volume dilatability $$K_{effective,j}\left[\frac{inches^2}{pound-force}\right]$$

given by Equation 8:

$$C_{h,j,i}\left[\frac{inches^5}{pound-force}\right] = [V_{0j,i}[inches^3]]K_{effective,j,i}\left[\frac{inches^2}{pound-force}\right] \quad \text{(Equation 8)}$$

Hydraulic capacitance is not a volume but rather a potential for volume change due to pressure change.

Note that $V_{0j,i}$ is the volume of syringe j without any deformation. It is important to recognize that $V_{0j,i}$ is not a constant for the syringe but instead varies with each piston displacement increment $\Delta y_{j,i}$. As the injection proceeds the theoretical volume $V_{0j,i}$ decreases by the volume of the square of the syringe inner diameter multiplied by $\Delta y_{j,i}$ as described by Equation 9:

$$V_{0j,i} = V_{0j,i-\Delta t} - \Delta_{0j,i}\Delta y_{j,i} \quad \text{(Equation 9)}$$

An example for dilatability is given in Equation 10 for a long tube that neglects end effects:

$$K_{effective,tube,i}\left[\frac{inches^2}{pound-force}\right] \cong \frac{1}{E_{tube}} \quad \text{(Equation 10)}$$

where $E_{tube}$ is the modulus of elasticity of the tube material. For example, a steel tube will dilate less than a plastic tube at a given internal pressure since $E_{steel} \cong 80 E_{plastic}$ Volume in capacitance at time i is residual volume $V_{residual,j,i}$ [inches$^3$]) that is due to elastic swelling and/or elastic shape change of the components of the fluid delivery system resulting from pressure $P_i$ applied to those components:

$$V_{residual,j,i}[inches^3] = C_{h,j,i}\left[\frac{inches^5}{pound-force}\right]P_i\left[\frac{pound-force}{inch^2}\right] \quad \text{(Equation 11)}$$

which leaves at total syringe volume $V_{j,i}$:

$$V_{j,i} = V_{0j,i} + V_{residual,j,i} \quad \text{(Equation 12)}$$

It is important to distinguish between residual volume in capacitance and flow into or out of capacitance. Flow into or out of capacitance occurs when pressure changes and/or $V_{0j,i} \neq V_{0j,i+\Delta t}$. Recall that the piston increment $\Delta y_j$ changes $V_{0j,i}$. Flow into or out of capacitance due to pressure change subtracts or adds, respectively, to fluid displaced by the piston displacement $\Delta y_{j,i}$.

Total Effects in Fluid-Structure Interaction

Table 2 includes subscript notation for total effects. For example, syringes that are not isolated with a valve will have a cumulative flow rate given by Equation 13:

$$\dot{Q}_{TOTAL,i} = \dot{Q}_{A,i} + \dot{Q}_{B,i} \quad \text{(Equation 13)}$$

Capacitance must also be considered as a cumulative variable when syringes are not isolated with a valve that is closed as described in Equation 14:

$$C_{h,TOTAL,i} = C_{h,A,i} + C_{h,B,i} \quad \text{(Equation 14)}$$

Capacitance and Syringe Flow Rate

Decreasing pressure results in flow out of capacitance that is in the opposite direction to flow into capacitance since the same components that dilate and/or compress with increasing pressure contract and/or extend with decreasing pressure. Effect of flow to and from capacitance is added to the right-hand side of the equation above to account for the volume rate of piston displacement:

$$A_{j,i-\Delta t}\Delta \frac{y_{j,i}}{\Delta t}\left[\frac{inch^3}{second}\right] = \quad \text{(Equation 15)}$$

$$\frac{P_i\left[\frac{pound-force}{inch^2}\right]}{R_{TOTAL,i}\left[\frac{pound-force-second}{inch^5}\right]} +$$

$$C_{h,TOTAL,i}\left[\frac{inches^5}{pound-force}\right]\left(\frac{P_i - P_{i-1}}{\Delta t}\right)\left[\frac{pound-force}{inch^2-second}\right]$$

Observe that total capacitance must be used in Equation 15 if the syringes are not isolated with a closed valve. For a syringe labeled j, recall that flow into or out of capacitance subtracts from or adds to, respectively, the volume displacement due to $\Delta y_{j,i}$. This can be expressed as Equation 16 for flow rate out of syringe j at time i equal to $\dot{Q}_{j,i}$:

$$\dot{Q}_{j,i} = \frac{P_i\left[\frac{pound-force}{inch^2}\right]}{R_{TOTAL,i}\left[\frac{pound-force-second}{inch^5}\right]} = \quad \text{(Equation 16)}$$

$$A_{j,i-\Delta t}\frac{\Delta y_{j,i}}{\Delta t}\left[\frac{inch^3}{second}\right] - C_{h,TOTAL,i}\left[\frac{inches^5}{pound-force}\right]$$

$$\left(\frac{P_i - P_{i-1}}{\Delta t}\right)\left[\frac{pound-force}{inch^2-second}\right].$$

Equations 15 and 16 reflect three mathematical details important for conservation of volume during flow into or out of capacitance. The first detail is that hydraulic capacitance is proportional to theoretical volume $V_{0,j,i}$ that is a product of the zero-volume syringe cross-sectional area $A_{0,j,i}$.

The second detail is that theoretical flow rate in syringe j at time i is a function of the actual syringe cross-sectional area $A_{j,i-\Delta t}$ at the start of time increment i and is the product $$A_{j,i-\Delta t}\Delta \frac{y_{j,i}}{\Delta t}.$$

The third mathematical detail is that flow into or out of capacitance is a function of the change in pressure $(P_i-P_{i-\Delta t})$. Recognizing these three details accounts for the residual volume $C_{h,j,i}(P_i-P_{i-\Delta t})$ displaced by the piston that contributes to the flow rate out of the syringe $\dot{Q}_{j,i}$ and total values $C_{h,TOTAL,i}(P_i-P_{i-\Delta t})$ and $\dot{Q}_{TOTAL,i}$. If $(P_i-P_{i-\Delta t})=0$ then flow rate in or out of capacitance is zero except for the residual volume in capacitance displaced by piston motion $\Delta_{j,i}$ equal to $\Delta_{j,i-\Delta t}\Delta y_{j,i}$ which reflects steady state flow rate and pressure. The present disclosure gives methods to maintain constant flow rate during transitions from one fluid to another when fluid is also flowing into and out of capacitance. Calculating flow rate and pressure during these transitions requires additional calculations.

Clearance Between Components and Piston Displacement $\Delta y_{j,i}$

Potential for clearance between parts was discussed earlier to allow for assembly. Such clearance adds or subtracts from $\Delta y_{j,i}$ if dimension tolerance conditions in mechanical linkage allow displacement that results in $\Delta y_{j,i}$ being effectively changed by such clearances.

Conditions resulting in actual piston displacement varying from that of theoretical include overcoming a threshold friction force, deformation over a range that excludes contact until a threshold value of deformation is exceeded, and other discontinuities or step changes in the load-deformation relationship.

Empirical relationships often reveal effects and ordinate values of pressure and piston position of these thresholds and steps. Changes in curves that relate variables like piston displacement or pressure to response variables like capacitance, pressure, and flow rate are often mathematically discontinuous because of the steps and thresholds. Note that pressure can be either a dependent or independent variable.

Compensation for such clearance can be calculated or empirically determined. The clearance data can be used to modify piston displacement $\Delta y_{j,i}$ accordingly in order to further optimize fluid delivery control.

Determination of Capacitance and Residual Volume

Empirical determination of capacitance and residual volume is often more efficient and accurate than calculation. Many parameters used in calculation must still be obtained empirically. A combination of the two methods is typically used.

Accurately calculating capacitance $C_{h,j,i}$ and residual volume $V_{residual,j,i}$ [inches$^3$] requires hyper-elasticity and assembly compliance and clearance to avoid concluding a response that is too stiff that under estimates capacitance. Recall from Equation 11 that capacitance is the product of zero-stress volume $V_{0,j,i}$ at time i and elasticity relating volume change to pressure with $K_{effective,j,i}$.

Residual volume $V_{residual,j,i}$ was given in Equation 12.

One means of calculating capacitance and residual volume utilizes mechanics of materials to determine the unit dimension change in [inches] of one or more components that create the fluid cavity or conduit of volume $V_{0,j,i}$ [inches$^3$] per a change in pressure $$P_i\left[\frac{pound-force}{inches^2}\right].$$

It is important to recognize that neither volume nor mass will be conserved if there are errors in either the mechanical properties or mechanics of materials formulae.

An example of mechanics of materials models the syringe using a cylinder j of internal diameter $\varphi_{j,i=0}$ and length $L_{Sj,i=0}$ with the end that has the tubing connection assumed closed. The syringe modeled with a cylinder j that has elastic modulus $E_S$, Poisson's Ratio $v_S$, and wall thickness $t_S$ can dilate/contract and expand/compress by both diameter change and length change $\Delta L_{Sj,i}$ respectively, due to pressure $P_i$ at time i as described in Equations 17 and 18:

$$\varphi_{j,i}[inches] = \varphi_{j,0} + \frac{P_i\varphi_{j,0}^2}{2E_S t_S}\left\{1 - \frac{v_S}{2}\right\} \quad \text{(Equation 17)}$$

$$\Delta L_{Sj,i}[inches] = \frac{P_i\varphi_{j,i}L_{Sj,0}}{2E_S t_S}\left\{\frac{1}{2} - v_S\right\} \quad \text{(Equation 18)}$$

$A_{j,i}$ is cross-sectional area of the syringe at time i and pressure $P_i$:

$$A_{j,i}[inches^2] = \frac{\pi}{4}\varphi_{j,i}^2 \quad \text{(Equation 19)}$$

Diameter of the hyper-elastic plunger is assumed equal to that of the syringe. Piston length change $\Delta L_{Pj,i}$ at pressure $P_i$ is calculated by $$\Delta L_{P,j,i}[\text{inches}] = \frac{P_i L_{P,j,0}}{A_{j,i} E_{PL,i}}. \quad \text{(Equation 20)}$$

Hyper-elasticity must be accounted for in the plunger elastic modulus $E_{PL,i}$:

$$E_{PL,i}\left[\frac{\text{pound-force}}{\text{inches}^2}\right] = E_0 + f(P_i) \quad \text{(Equation 21)}$$

where $E_0$ is constant and $f(P_i)$ is the function of pressure $P_i$ that relates the hyper elasticity to the stress state of the plunger. $E_{PL,i}$ increases with stress that results from pressure $P_i$. If plasticity occurs such as in the rolling diaphragm then a similar, non-linear, mathematical technique like that in Equation 21 must be considered in order to correctly model the response Syringes are not always filled to their capacity so a fill volume $V_{FILL,j}$ [inches$^3$] is defined at zero pressure that allows calculation of a length of the syringe that is filled, $L_{FILL,j}$:

$$L_{FILL,j}[\text{inches}] = \frac{V_{FILL,j}}{\frac{\pi}{4}\varphi_{j,i=0}^2} \quad \text{(Equation 22)}$$

An actual fluid length that accounts for total deformation and piston displacement $\Delta y_{j,i}$ at time i is given by:

$$\text{Fluid Length}_{j,i} = L_{FILL,j}[\text{inches}] + \Delta L_{PJ,i} + \Delta L_{Sj,i} - \sum_{i=1}^{n}\Delta y_{j,i} \quad \text{(Equation 23)}$$

Theoretical volume of the syringe at time i and zero pressure using mechanics of materials is given by $$V_{0,j,i}[\text{inches}^3] = \frac{\pi\varphi_{j,0}^2}{4}\left[L_{FILL,j} - \sum_{i=1}^{n}\Delta y_{j,i}\right] \quad \text{(Equation 24)}$$

Actual fluid volume of the syringe at time i and pressure $P_i$ is given by $$V_{ACTUAL,j,i}[\text{inches}^3] = A_{j,i}\text{Fluid Length}_{j,i} \quad \text{(Equation 25)}$$

Residual volume in syringe j at time i calculated below in Equation 26 as a function of capacitance is also calculated from mechanics of materials:

$$V_{residual,j,i}[\text{inches}^3] = V_{ACTUAL,j,i} - V_{0,j,i} \quad \text{(Equation 26)}$$

Note that the volume displaced at time i by $\Delta y_{j,i}$ uses the syringe area $A_{j,i-\Delta t}$ that uses pressure from the prior increment. The reason for using area at time i–$\Delta t$ is because pressure results from flow rate.

Capacitance is calculated using this format since residual volume is proportional to capacitance:

$$C_{h,j,i}\left[\frac{\text{inches}^5}{\text{pound-force}}\right] = \frac{V_{residual,j,i}}{P_i - P_0} \cong \frac{dV}{dP} \quad \text{(Equation 27)}$$

where $P_0$ is typically zero.

Flow rate in or out of the residual volume of syringe j capacitance at time i is then calculated as a function of the incremental change in pressure as it was in Equation 16:

$$\dot{Q}_{cap,j,i}\left[\frac{\text{inches}^3}{\text{second}}\right] = C_{h,j,i}\left(\frac{P_i - P_{i-\Delta t}}{\Delta t}\right) \quad \text{(Equation 28)}$$

Flow out of capacitance supplements flow from piston displacement $\Delta y_{j,i}$ such that $$\dot{Q}_{j,i} = A_{j,i}\frac{\Delta y_{j,i}}{\Delta t} - \dot{Q}_{cap,j,i} \quad \text{(Equation 29)}$$

Flow out of capacitance is negative by the sign convention used in Equation 28 so flow out of capacitance adds to that in Equation 29 from piston displacement $\Delta y_{j,i}$. Equations 28 and 29 rely on pressure defined as a function of time which can be calculated, acquired from real-time data, or accessed from a database.

A related but more precise means of calculating residual volume discretizes the component geometry into finite elements and uses typical potential energy methods like those of either Rayleigh-Ritz or Galerkin to relate pressure and fluid dynamics to stress and strain in the injector components that are subsequently used to determine residual volume. Finite element models assuming two-dimensional axisymmetry including both hyper-elasticity and contact can be processed quickly to provide data at a rate sufficient to modify the piston velocity and control flow rate using computational capability on contemporary injectors.

Syringes designed as a rolling diaphragm may benefit from finite-element modeling for capacitance calculations and fluid structure interaction since the shape of the capacitance volume is more complicated than that for a syringe made with a separate plunger. Capacitance includes, for example, the annular volume that surrounds the rolling diaphragm and is bounded by the pressure jacket.

Empirical Determination of Capacitance and Residual Volume

Total system capacitance is inherent to each fluid delivery system and to the various fluid path elements thereof, and depends on a plurality of factors beyond pressure and volume of fluid remaining in the system, including, without limitation, injector construction, mechanical properties of materials used to construct the syringe, plunger, pressure jacket surrounding the syringe, interaction between molecules of different liquids that changes their specific volumes, and fluid lines delivering the fluid to the patient; size of the syringe, plunger, pressure jacket; length and diameter of tubing; and local geometry changes such as orifices and bends through which the fluid must pass under pressure; and fluid properties, such as temperature change, temperature gradients, viscosity, and density.

Variables and relationships given above for calculating capacitance and residual volume reveal difficult challenges.

Figure 52A:
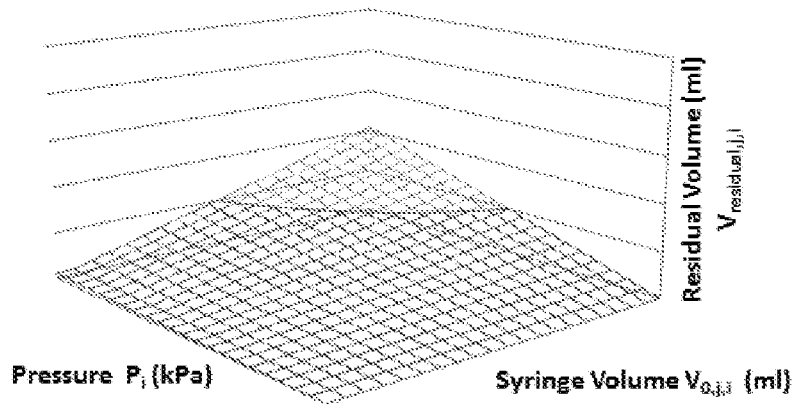
FIGS. 52A and 52B are graphs of three-dimensional surfaces showing a residual volume of undelivered fluid in a syringe with respect to injection volume and pressure.
Figure 52B:
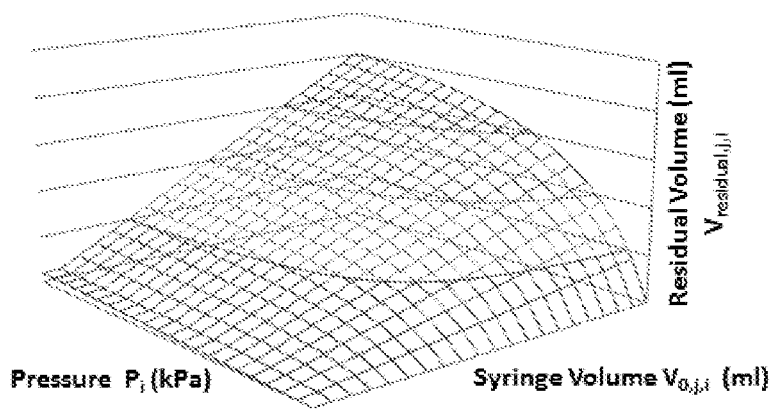

Empirical determination is typically used at least in part to produce capacitance and residual volume data. More specifically, the curved surface in FIGS. 52A and 52B illustrates exemplary proportional relationships between residual volume in a syringe as a function of both volume remaining in the syringe and pressure in the syringe. Equation 30 is an approximate fit for residual volume for syringe j at time i:
Residual Volume Equation:

$$V_{residual,j,i}[inches^3] = \left(\frac{1}{E_0 + E_1 P_i}\right) P_i V_{0,j,i} \quad \text{(Equation 30)}$$

Variables:

$E_0\left[\frac{\text{pound-force}}{inch^2}\right]$ = constant for elastic modulus $E_1$ = coefficient for pressure to account for non-linear deformation $P_i\left[\frac{\text{pound-force}}{inch^2}\right]$ = Pressure at time $i$ $V_{0,j,i}[inches^3]$ = Remaining syringe volume at zero pressure at time $i$.

Capacitance is calculated in Equation 31 by dividing residual volume by pressure:

$$C_{h,j,i}\left[\frac{inches^5}{\text{pound-force}}\right] = \frac{V_{residual,j,i}}{P_i} \quad \text{(Equation 31)}$$

Other numerical and statistical methods may be used to characterize data for Equation 30. If syringes are not isolated with a closed valve then all volumes must be considered in these relationships.

FIG. 52A plots a surface assuming linear elasticity. FIG. 52B plots a surface that includes non-linear deformation. Increasing non-linear response as a function of pressure and overall greater residual volume in FIG. 52B illustrates the effect of these variables as compared to the linear elastic response in FIG. 52A.

A mathematical discontinuity between actual and calculated residual volume and capacitance values occurs at zero syringe volume $V_{0,j,i}$. The plots correctly illustrate that residual volume is an independent function of pressure at zero pressure syringe volume $V_{0,j,i}$ since pressure independently deforms individual parts that cumulatively create volume as indicated in Equations 17 through 23.

The data given at zero pressure syringe volume $V_{0,j,i}$ is an estimate and is only for illustration. Empirical results for specific injector configurations specifically define the exemplary surfaces shown in FIGS. 52A and 52B.

Figure 51:
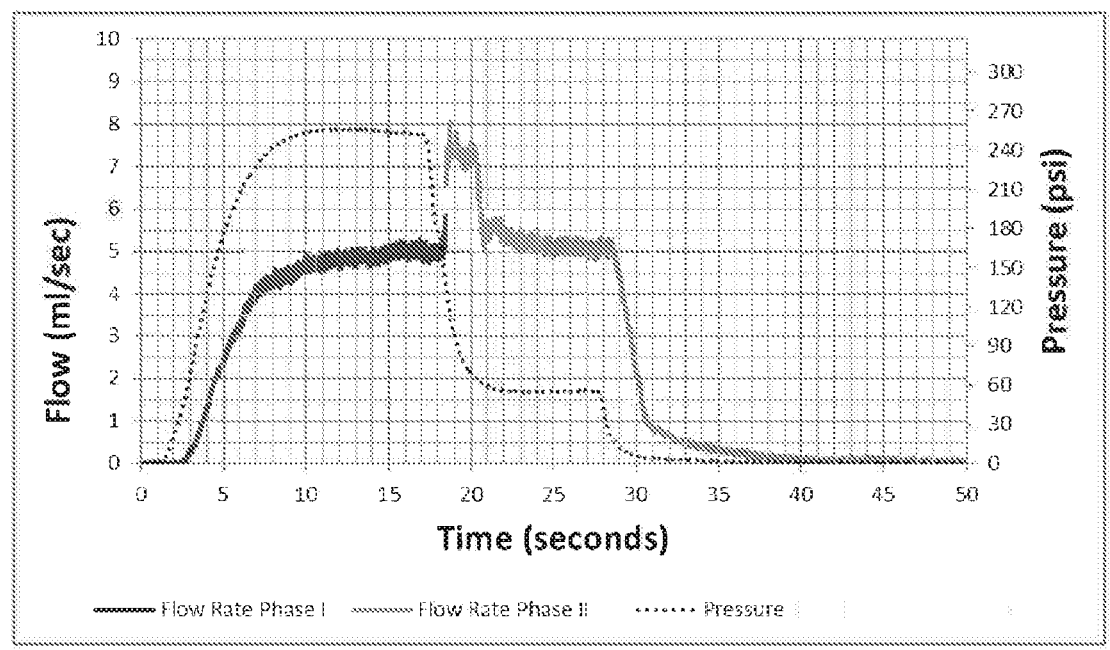
FIG. 51 is a graph illustrating flow rate with respect to time for a multiphase injection.

Flow Rate and Pressure During Transitions Without Correction of Overrate—Time to Steady State Conditions Equations above demonstrate that flow into or out of residual volume of hydraulic capacitance occurs when the pressure changes. Equation 16 quantifies the difference between volume that piston motion displaces and that flow into or out of capacitance subtracts or adds to the volume that is injected. FIG. 51 illustrates the effect of suddenly changing hydraulic system fluid properties and characteristics like viscosity, density, valve position, etc. These changes proportionately and instantaneously change both resistance to flow and flow rate while the pressure changes at an exponential rate governed by a time constant $\tau_i$ that is the product of hydraulic capacitance and hydraulic resistance. Calculation of $\tau_i$ is given below in Equation 32:

$$\tau_i[\text{second}] = R_{TOTAL,i}\left[\frac{\text{pound-force-second}}{inch^5}\right] C_{h,TOTAL,i}\left[\frac{inches^5}{\text{pound-force}}\right] \quad \text{(Equation 32)}$$

Units for factors for $\tau_i$ $R_{TOTAL,i}$ and $C_{h,TOTAL,i}$ yield time as a product because increasing hydraulic resistance increases time for a given volume to flow into a volume of magnitude governed by the capacitance. Time constant $\tau_i$ increases proportional to $V_{0,j,i}$, the zero pressure volume at time i. Decreasing component stiffness also increases $\tau_i$ since a deformable volume dilates more for a given pressure increase as stiffness decreases. Note that component stiffness is the inverse of $K_{effective,j}$.

Sources of Pressure Data During Transition from Contrast to Saline

Ideally pressure $P_i$ is available as real-time acquired data or accessed from a database. If pressure data is not available, then $P_i$ can be calculated over the transition time range if steady state values and initial conditions are given. An example of calculations required to analytically determine transient pressure is presented below.

Equation 16 gave the flow rate from syringe j at time i and is copied below for convenience in Equation 33. The example in Equation 33 considers both total capacitance for multiple syringes that are not isolated with valves and the total hydraulic resistance:

$$\dot{Q}_{j,i} = \quad \text{(Equation 33)}$$

$$\frac{P_i\left[\frac{\text{pound-force}}{inch^2}\right]}{R_{TOTAL,i}\left[\frac{\text{pound-force-second}}{inch^5}\right]} = A_{j,i-\Delta t}\frac{\Delta y_{j,i}}{\Delta t}\left[\frac{inch^3}{\text{second}}\right] -$$

$$C_{h,TOTAL,i}\left[\frac{inches^5}{\text{pound-force}}\right]\left(\frac{P_i - P_{i-1}}{\Delta t}\right)\left[\frac{\text{pound-force}}{inch^2\text{-second}}\right].$$

Determining pressure during a transition such as when syringe A finishes injecting contrast and syringe B begins injecting saline requires manipulation of Equation 33 so that time constant $\tau_i$ can be calculated and subsequently used to define pressure and flow rate through the transition. Derivation of the equations is given below without units for clarity.

$$A_{j,i-\Delta t}\frac{\Delta y_{j,i}}{\Delta t}\left[\frac{inch^3}{\text{second}}\right] = \frac{P_i\left[\frac{\text{pound-force}}{inch^2}\right]}{R_{TOTAL,i}\left[\frac{\text{pound-force-second}}{inch^5}\right]} + \quad \text{(Equation 34)}$$

$$C_{h,TOTAL,i}\left[\frac{inches^5}{\text{pound-force}}\right]\left(\frac{P_i - P_{i-\Delta t}}{\Delta t}\right)\left[\frac{\text{pound-force}}{inch^2\text{-second}}\right]$$

Where $$\frac{dP}{dt} = \left(\frac{P_i - P_{i-\Delta t}}{\Delta t}\right) \quad \text{(Equatioin 35)}$$

and $$\dot{Q}_{STEADY\ STATE,j} = A_{j,i-\Delta t}\frac{\Delta y_{j,i}}{\Delta t} \quad \text{(Equation 36)}$$

from Equation 34. Steady state flow rate $\dot{Q}_{STEADY\ STATE,j}$ is also the programmed flow rate neglecting small errors. Steady state pressure $P_{STEADY\ STATE,j}$ is typically determined empirically although it can be calculated with knowledge of hydraulic resistance and the steady state flow rate using Equation 1.

Substituting $\frac{dP}{dt}$ and $\dot{Q}_{STEADY\ STATE,j}$:

$$\dot{Q}_{STEADY\ STATE,j} = \frac{P_i}{R_{TOTAL,i}} + C_{h,TOTAL,i}\frac{dP}{dt} \quad \text{(Equation 37)}$$

Multiplying both sides by $R_{TOTAL,i}$ gives $$R_{TOTAL,i}\dot{Q}_{STEADY\ STATE,j} = P_i + R_{TOTAL,i}C_{h,TOTAL,i}\frac{dP}{dt} \quad \text{(Equation 38)}$$

Where $$\tau_i = R_{TOTAL,i}C_{h,TOTAL,i} \text{ and } P_{STEADY\ STATE,j} = R_{TOTAL,i}\dot{Q}_{STEADY\ STATE,j}. \quad \text{(Equation 39)}$$

Substituting gives $P_{STEADY\ STATE,j} = P_i + \tau_i\frac{dP}{dt}$

Manipulating to prepare for integration gives $$(P_{STEADY\ STATE,j} - P_i) = \tau_i\frac{dP}{dt} \quad \text{(Equation 40)}$$

$$dt(P_{STEADY\ STATE,j} - P_i) = \tau_i dP \quad \text{(Equation 41)}$$

$$\frac{dt}{\tau_i} = \frac{dP}{(P_{STEADY\ STATE,j} - P_i)} \quad \text{(Equation 42)}$$

Multiplying both sides by (−1) so $P_i$ is positive $$\frac{-dt}{\tau_i} = \frac{dP}{(P_i - P_{STEADY\ STATE,j})} \quad \text{(Equation 43)}$$

Distinguishing $P$ from $P'$ for mathematical clarity and the integrating gives $$\int_{P_{i-\Delta t}}^{P_i}\frac{dP'}{(P'_i - P_{STEADY\ STATE,j})} = \frac{-1}{\tau_i}\int_{t=(i-\Delta t)}^{t=i}dt \quad \text{(Equation 44)}$$

Substituting the limits of integration $$\ln(P'_i - P_{STEADY\ STATE,j})\big|_{P_{i-\Delta t}}^{P_i} = \frac{-1}{\tau_i}t\big|_{t=(i-\Delta t)}^{t=i} \quad \text{(Equation 45)}$$

$$\ln(P_i - P_{STEADY\ STATE,j}) - \ln(P_{i-\Delta t} - P_{STEADY\ STATE}) = \frac{-\Delta t}{\tau_i}. \quad \text{(Equation 46)}$$

Simplifying

Where $\Delta t = i - (i - \Delta t)$ (Equation 47)

$$\ln\frac{(P_i - P_{STEADY\ STATE,j})}{(P_{i-\Delta t} - P_{STEADY\ STATE,j})} = \frac{-\Delta t}{\tau_i} \quad \text{(Equation 48)}$$

$$e^{\ln\frac{(P_i - P_{STEADY\ STATE,j})}{(P_{i-\Delta t} - P_{STEADY\ STATE,j})}} = e^{\frac{-\Delta t}{\tau_i}} \quad \text{(Equation 49)}$$

$$\frac{(P_i - P_{STEADY\ STATE,j})}{(P_{i-\Delta t} - P_{STEADY\ STATE,j})} = e^{\frac{-\Delta t}{\tau_i}} \quad \text{(Equation 50)}$$

$$(P_i - P_{STEADY\ STATE,j}) = (P_{i-\Delta t} - P_{STEADY\ STATE,j})e^{\frac{-\Delta t}{\tau_i}} \quad \text{(Equation 51)}$$

If resistivity, capacitance, and piston velocity were constant during the contrast to saline transition then five multiples of $\tau_i$ [seconds] would be required to reach 99% of steady state pressure $P_{STEADY\ STAT,jE}$ after starting from initial pressure $P_{initial} = P_{i-\Delta t}$ as described by the step-function, exponential, relationship below:

$$P_i = P_{STEADY\ STATE,j} + \quad \text{(Equation 52)}$$
$$(P_{i-\Delta t} - P_{STEADY\ STATE,j})e^{\frac{-\Delta t}{R_{TOTAL,i}C_{h,TOTAL,i}}}$$

Initial pressure $P_{i-\Delta t}$ for the first iteration is either the steady state pressure for the contrast or the maximum contrast pressure if steady state pressure is not achieved for contrast. Steady state may not be achieved due to a low volume injection that did not allow time for steady state conditions or a limit for pressure on the injector was exceeded.

Since $R_{Density}$ is a function of flow rate and there is a mixture of fluids during the transition, both $P_j$ and $\tau_j$ must be solved iteratively by updating all of the variables in Equation 52, i.e., they are variable coefficients. Recall piston displacement influences capacitance since it directly changes theoretical volume $V_{0,j,i}$ which is the reason that capacitance is labeled $C_{h,j,i}$ to indicate that it varies with time if piston velocity is not equal to zero. High-volume injections have more initial capacitance and longer initial time constants than a lesser fill volume in the same syringe.

Flow rate $\dot{Q}_{j,i}$ must also be solved iteratively since it is a factor in $R_{Density}$. The algorithm to calculate $\dot{Q}_{j,i}$ follows in the next section.

Iterative Equations for Flow Rate During Transition from Contrast to Saline

Pressure lags the flow rate transition as theory predicts and FIG. 51 illustrates in systems with capacitance as contrast injection ends and saline injection begins. If pressure is not available as a database or real-time data, then it can be calculated incrementally during the transition from contrast to saline. The key is to calculate pressure at time i, $P_i$, using the prior flow rate $\dot{Q}_{i-\Delta t}$ as a factor for the time constant labeled $\tau_i$:

$$P_i = P_{STEADY\ STATE,j} + (P_{i-\Delta t} - P_{STEADY\ STATE,j})e^{\frac{-\Delta t}{\tau_i}} \quad \text{(Equation 53)}$$

where $$\tau_i = R_{TOTAL,i-\Delta t}C_{h,TOTAL,i} \text{ and} \quad \text{(Equation 54)}$$

$$R_{TOTAL,i} = \sum_{j=1}^{n}\frac{\left[\frac{128\mu_{saline,j}}{pound-force-second}\right]L_j[inch]}{\pi\phi_j^4[inch^4]} + \quad \text{(Equation 55)}$$

$$\dot{Q}_{TOTAL,i-\Delta t}\left[\frac{inch^3}{second}\right]\sum_{k=1}^{m}\frac{\left[\frac{8\rho_{saline,k}}{pound-force-second^2}\right]}{\pi^2\phi_k^4[inch^4](Constant)^2}$$

Note that for many injections n=2 and m=1. Simplifying equation 55 for subsequent calculations gives:

$$R_{TOTAL,i} = R_0 + R_1\dot{Q}_{TOTAL,i-\Delta t} \quad \text{(Equation 56)}$$

Format of Equation 56 for $R_{TOTAL,i}$ will be of use in solving for $\dot{Q}_{j,i}$. Flow rate may also be available as a function of pressure although this is less likely in the transition range. Several numerical techniques can be used to calculate flow rate, such as the one below.

To find $\dot{Q}_{j,i}$, substitute $P_i$ and $(R_0+R_1\dot{Q}_{j,i})$ into Equation 1:

$$P_i = R_{TOTAL,i}\dot{Q}_{j,i} = (R_0+R_1\dot{Q}_{j,i})\dot{Q}_{j,i} = R_0\dot{Q}_{j,i} + R_1\dot{Q}_{j,i}^2, \quad \text{(Equation 57)}$$

Modify the format to find the positive root $\dot{Q}_{j,i}$:

$$R_1\dot{Q}_{j,i}^2 + R_0\dot{Q}_{j,i} - P_i = 0 \quad \text{(Equation 58)}$$

$$\dot{Q}_{j,i} = \frac{-R_0 \pm \sqrt{R_0^2 - 4R_1 P_i}}{2R_1} \quad \text{(Equation 58')}$$

where the uncorrected flow rate is the positive square root in Equation 58'.

Transition Behavior at Beginning and End of Treatment

In the absence of real time data or a database, the exponential relationships in Equations 33 through 58' quantifying pressure and flow rate through the transition from contrast to saline also describe the period to steady state at both the beginning and end of the treatments. An example calculation follows for a contrast injection flowed by a saline injection where the two syringes are not isolated with a valve.

Initial and boundary conditions simplify the calculations for pressure and flow rate to steady state both at the beginning of an injection and at the end of an injection. At the beginning of the injection. $\dot{Q}_{STEADY\ STATE,j}$ is the programmed rate and pressure $P_{STEADY\ STATE,j}$ is either determined by experiment or estimated by $$P_{STEADY\ STATE,j} = CA_{j,0}\frac{\Delta y_{j,i}}{\Delta t}R_{TOTAL,i} \quad \text{(Equation 59)}$$

where C is a constant used to estimate the final diameter due to $P_{STEADY\ STATE,j}$. Recall that this elastic diameter influence is on the order of 1.0% and may be neglected with little influence depending on the precision required. Pressure and flow rate are calculated with the exponential relationships below using the same algorithm presented above:

$$P_i = P_{STEADY\ STATE,j} + (P_{i-\Delta t} - P_{STEADY\ STATE,j})e^{\frac{-\Delta t}{R_{TOTAL,i}C_{h,TOTAL,i}}} \quad \text{(Equation 60)}$$

$$\dot{Q}_{j,i} = \dot{Q}_{STEADY\ STATE,j} + (\dot{Q}_{j,i-\Delta t} - \dot{Q}_{STEADY\ STATE,j})e^{\frac{-\Delta t}{R_{TOTAL,i}C_{h,TOTAL,i}}} \quad \text{(Equation 61)}$$

After either reaching steady state or the end of the injection, Equation 16 may be used to complete the treatment. Note that subscript j identifies the individual syringe and that $V_{0,j,i}$ varies with both fill volume $L_{FILL,j}$ and piston displacement $\Delta y_{j,i}$.

The end of the treatment similarly uses the exponential relationships for both pressure and flow rate. Steady state values for both pressure and flow rate are zero; initial conditions are the values at the end of piston displacement for the saline. In addition to pressure and flow rate calculations at the end of the treatment, the sum of time increments to reach zero determines how long fluid will continue to flow out of the catheter due only to flow out of capacitance, $\dot{Q}_{j,i} = \dot{Q}_{CAP,i}$.

Controlling Flow Rate

Iteration continues through the criteria of time and/or stroke length increments. As a new syringe B with the saline begins injection, fluid properties including density and viscosity will be those of the mixture $\mu_{mix}$ and $\mu_{mix}$ in the tubing which is of minimal influence since its only about 1 ml.

Injection with a different fluid is the point in the algorithm where if $(\dot{Q}_{j,i} > \dot{Q}_{STEADY\ STATE,j})$ then a decrease in piston displacement $\Delta y_{j,i}$ occurs incrementally as needed to limit flow rate $\dot{Q}_{j,i} < \dot{Q}_{STEADY\ STATE,j}$.

It is important to recognize that the passive response of the syringe that does not have specified piston displacement contributes to total flow and pressure such that its flow rate, pressure, and capacitance change. For example, if $\Delta y_{A,i} > 0$ and $\Delta y_{B,i} = 0$, then flow $\dot{Q}_{B,i}$ will be into residual volume of capacitance $C_{h,B,i}$ of syringe B such that $$\dot{Q}_{B,i} = -C_{h,B,i}\left[\frac{inches^5}{pound-force}\right] \quad \text{(Equation 62)}$$

$$\left(\frac{P_i - P_{i-\Delta t}}{\Delta t}\right)\left[\frac{pound-force}{inch^2-second}\right] \text{ due to}$$

Fluid $Length_{B,i} = L_{FILL,B}[inches] + \Delta L_{P,B,i} + \Delta L_{S,B,i}$ and $\quad$ (Equation 63)

$$A_{j,i}[inches^2] = \frac{\pi}{4}\varphi_{j,i}^2 \quad \text{(Equation 64)}$$

since both fluid length and diameter are proportional to pressure $P_i$. Total flow rate is reduced by $\dot{Q}_{B,i}$ in this scenario since $\dot{Q}_{B,i}$ is less than zero:

$$\dot{Q}_{B,i} < 0 \quad \text{(Equation 65).}$$

The present disclosure utilizes control of piston displacement $\Delta y_{j,i}$ to vary both flow rate and capacitance in order to maintain programmed flow rates. Recall that $\Delta y_{j,i}$ directly influences flow rate $\dot{Q}_{j,i}$ by volume displacement and capacitance $C_{h,j,i}$ by changing fluid length both of which change pressure $P_i$ and the resulting total flow rate $\dot{Q}_{TOTAL,i}$.

Methods for Reducing Overrate

As discussed herein, a multiphase injection can include a contrast or first phase followed by a second or saline flush phase. At the start of the saline flush phase, the conduit or fluid path is full of contrast, which is typically a highly viscous fluid that is also of higher density and higher bulk modulus of elasticity than saline. As the injection proceeds, saline introduced to the conduit or fluid path begins to displace the contrast remaining in the fluid path. When the saline flush reaches the end of the conduit and the catheter, pressure $P_i$ begins to decrease significantly due to the hydraulic resistance difference between the saline and the contrast. As a result, flow rate $\dot{Q}_{TOTAL,i}$ at the early part of the second phase increases because $P_i > P_{STEADY\ STATE,j}$. This flow rate increase can be referred to as "a fluid flow spike" as shown in FIG. 51.

As an example of the mechanism for the difference in hydraulic resistance is that the viscosity ratio of contrast to saline can be 10:1, 20:1, or 26:1. Density ratio of contrast to saline can be 1.4:1. It is noted that the flow rate does not increase by a factor 10, 20, or 26 during the saline flush phase, because a significant amount of pressure is required to accelerate fluid through narrow catheters for delivery to the patient resulting in the density resistance being a function of the flow rate. In a similar manner, due to residual volume in hydraulic capacitance of the syringes and other fluid path elements, the pressure does not drop instantly since it takes a proportional amount of time for residual volume to flow out of capacitance proportional to the time constant $\tau_i$.

In some examples, during the injection, potential energy or pressure can be converted into the kinetic energy (e.g., fluid velocity). In many fluid systems, this kinetic energy can be recovered in a properly designed diffuser. However, in fluid delivery applications, the narrowest element is usually the catheter. In that case, high velocity fluid may dissipate its energy in the patient's vessel. The smaller the catheter, the more significant the effect of acceleration compared to that of the viscosity.

Figure 50:
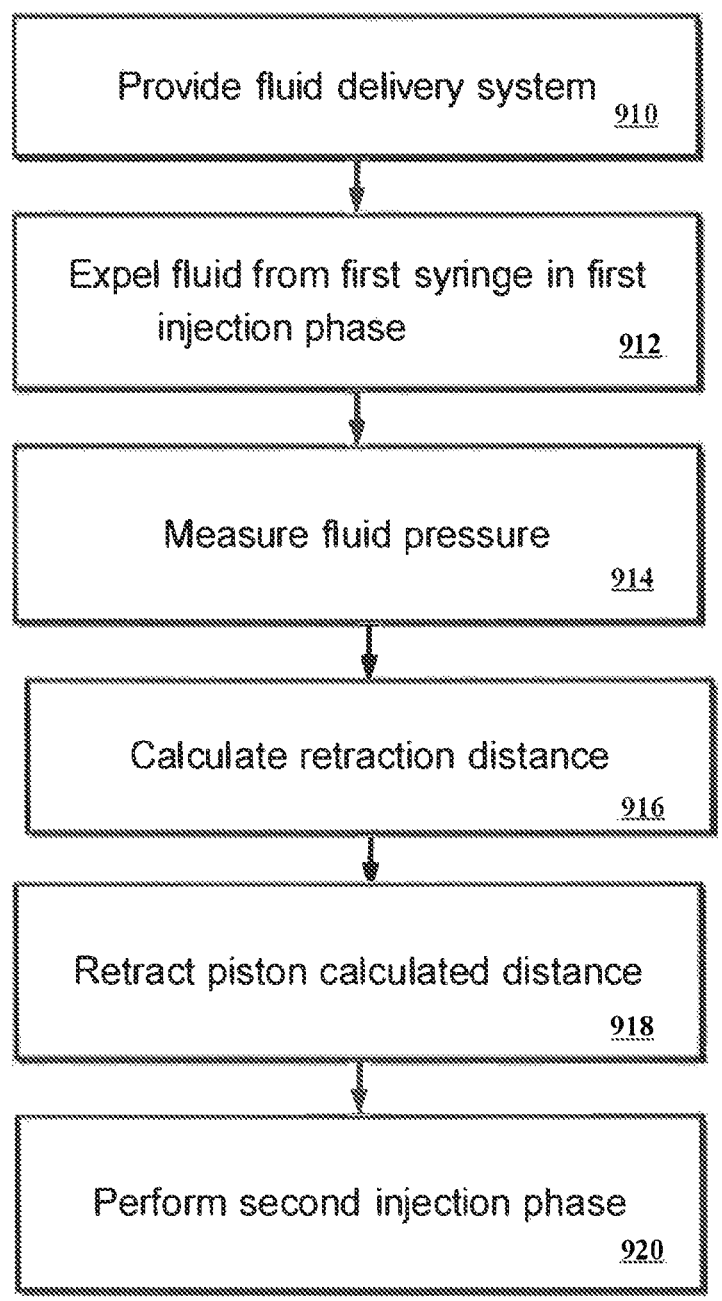
FIG. 50 is a flow chart of a fluid delivery process for a multiphase injection which reduces flow overrate according to an example of the present disclosure.

With reference to FIG. 50, a method for performing an injection with a fluid delivery system which addresses fluid velocity increases caused by differences in fluid density or viscosity and which reduces fluid overrate or fluid flow spike in a multiphase injection is illustrated. The method is adapted to maintain a substantially constant fluid flow rate, flow volume, and pressure throughout a multiphase injection and, in particular, to address discontinuities in flow rate, fluid pressure, or volume, which can occur at transitions between phases of an injection for fluids of different densities and/or viscosities, such as a phase transition between contrast and saline.

As indicated at 910, a multiphase fluid delivery system is provided. The multiphase fluid delivery system can include a first syringe containing a first fluid and a second syringe containing a second fluid. In other embodiments, different pump-types with at least first and second fluids, such as piston pumps, peristaltic pumps, or combinations of different pumps may be utilized in multiphase fluid delivery injections, where fluid flow rates and phase transitions may be controlled using calculation processes and various methods described herein. In general, the first fluid delivered as part of the disclosed method is contrast and the second fluid is saline. In some examples, the first fluid is denser than the second fluid. In other examples, the first syringe and the second syringe may both contain contrast agents of the same or different concentrations. In some examples, the first syringe and the second syringe contain the same type and concentration of fluid. The fluid delivery system can also include a fluid conduit for conducting fluid from the first syringe and the second syringe to a patient. For example, the conduit can be a fluid path set as described in connection with FIGS. 1-6. The system also includes an injector having a first piston for expelling fluid from the first syringe and a second piston for expelling fluid from the second syringe. In some examples, the syringes are conventional disposable or reusable syringes configured to be inserted into a front loading injector and including a moveable plunger configured to be driven by the piston, as shown in FIG. 1. In other examples, rolling diaphragm syringes can be used for the injection procedures described herein. In other examples, other pumping mechanisms, such as piston pumps, peristaltic pumps, and combinations of these with syringes may be used for the injection procedures described herein.

As indicated at 912, an injection procedure is initiated by, for example, advancing the first piston to expel fluid from the first syringe into the conduit during a first injection phase. As the first injection phase occurs, as indicated at 914, fluid pressure in the first syringe and/or the second syringe is measured. Syringe pressure can be measured in various ways, for example via motor current, a strain gauge, a pressure gauge, or another suitable device associated with a syringe barrel or fluid conduit. Any change in pressure represents a change in the amount of fluid leaving the syringe.

It is understood, however, that the implementation of this approach depends upon whether the syringes are open to each other or separated by check valves or stopcocks. For example, if there are stopcocks on the output of each syringe, once the transition is made from contrast to saline and the respective check valve or stopcock is closed, only the saline syringe pressure is monitored and the saline plunger is moved accordingly. The contrast syringe is isolated from the fluid path. If the two syringes are connected through open tubes, then both pressures are preferably monitored and both plungers are preferably moved. For example, the contrast plunger may be moved backward at a rate such that no fluid flows out of the contrast syringe and the saline plunger may be moved backward or forward such that the desired saline flow rate is achieved. If the two syringes are connected with one or more check valves, again both pressures are preferably monitored and both plungers will need to be moved to prevent flow dribble of contrast out into the saline flush phase; however, the contrast syringe plunger may be moved or allowed to move backwards even more quickly because the check valve prevents any flow of saline into the contrast syringe.

As shown at 916, displacement distance that ranges over both a positive and negative direction for a syringe piston is calculated based on the measured or calculated pressure and a target fluid flow rate. In some cases, the distance is calculated only for the second or saline syringe. In other examples, a distance can be calculated for both syringes to relieve pressure in each syringe. For example, the distance or displacement can be calculated based on a relationship between the time course of the pressure in a syringe labeled B syringe and the fluid volume leaving, as expressed by a discrete time equation, referred to herein as the "Impedance model equation", shown below in Equation 66:

$$Q_{B,i} = A_{B,i-\Delta t} \frac{\Delta y_{B,i}}{\Delta t} - \left\{ C_{h,B,i} + \frac{V_{0,B,i}}{\beta_{B,i}} \right\} \frac{P_i - P_{i-\Delta t}}{\Delta t} \qquad \text{(Equation 66)}$$

Note that Equation 66 above accounts for residual volume from both capacitance $C_{h,B,i}$ and compression of the fluid volume $V_{0,B,i}$ divided by the fluid bulk modulus $\beta_{B,i}$. Fluid compression is negligible in radiology applications unless air is present in the fluid.

Equation 66 also indicates that syringe B is isolated from syringe A and other syringes since capacitance excludes that of syringe A. In this case, $Q_{B,i}=Q_{TOTAL,i}$: total flow rate is equal only to that from syringe B.

Derivation of Equation 66 is described in Equations 1 through 65. In Equation 66, $Q_{B,i}$ is the volumetric flow rate (with dimensions of length$^3$ per unit time (e.g., $L^3 t^{-1}$)) for fluid volume leaving the second or saline syringe at a given time i. $A_{B,i-\Delta t}$ is a cross-sectional area of the syringe. $\Delta y_{B,i}$ is the incremental displacement of the piston B at time i with units L. The value $C_{h,B,i}$ is a pressure and position dependent incremental, hydraulic, capacitance of syringe B in the fluid delivery system (e.g., the conduit or fluid path set and syringe). Specifically, $C_{h,B,i}$ is r change in volume of syringe B per unit pressure and has dimensions of length$^5$ per unit force (e.g., $L^5 F^{-1}$). For example, syringe capacitance can be characterized by the three-dimensional curves FIG. 52A and FIG. 52B showing proportional changes in injection volume and pressure with respect to undelivered volume in the syringe. Two different materials are used in FIG. 52A and FIG. 52B; in FIG. 52A the representative components are more stiff and directly proportional to pressure than those material properties in FIG. 52B, so both capacitance of components represented by FIG. 52A and time to respond are both less than those same variables represented in FIG. 52B.

Dimensional changes in the components due to thermal gradients and temperature changes influence the relationship between pressure and flow rate. Knowledge of the coefficient of thermal expansion for both fluids and components allows calculated strain and resulting dimensional changes to be added to the strain and dimensional changes due to pressure.

Time-dependent material properties of the components commonly called creep, stress relaxation, and viscoelasticity are significant in many of the polymer components used for injector components and measurably influence variables contributing the pressure-flow rate relationship. Adding time-dependent material data enables calculations used to modify piston speed to account for the time dependence. As shown by Equation 66, as pressure of the syringe starts to decrease, the syringe capacitance adds a volume-dependent value $$\left(\frac{V_{0,B,i}}{\beta_{B,i}}\right)$$

related to compressibility of fluid contained in the syringe to the piston dependent displacement of fluid $$\left(\frac{\Delta y_{j,i}}{\Delta t}\right).$$

In the volume-dependent value, $V_{0,B,i}$ is a theoretical, zero-pressure, volume of the syringe at time i and $\beta_{B,i}$ is a bulk modulus of the fluid contained in the syringe having dimensions of force per unit area (e.g., $FL^{-2}$). For liquids, which have a comparative large bulk modulus $\beta_{B,i}$, the impact of the volume-dependent value $$\left(\frac{V_{0,B,i}}{\beta_{B,i}}\right)$$

will generally be rather small. However, for a gas or a solution containing a substantial quantity of air the contribution of the volume-dependent value $$\left(\frac{V_{0,B,i}}{\beta_{B,i}}\right)$$

will be greater. Air in the fluid can be accumulated during injection which explains the time increment i assigned to $\beta_{B,i}$.

As discussed above, the change in pressure $(P_i - P_{i-\Delta t})$ is determined by (1) measuring fluid pressure during injection, (2) accessing a database of pressure versus time or (3) using fluid mechanics models common for servo hydraulics to predict pressure as a function of the component geometry, fluid properties, and desired flow rate. If pressure is calculated or accessed from a database, then the piston rate profile can be calculated to correct for overrate a priori. Accordingly, Equation 66 can be solved to determine a change in distance $(\Delta y_{j,i})$ needed to produce a desired fluid volume flow rate $(Q_{j,i})$. The change in distance or plunger displacement can be used for controlling movement of the injector piston. Piston displacement for any syringe or fluid can be calculated using Equation 66. However, the bulk fluid and syringe compliance constants must be updated to accurately represent the components, fluids, and associated properties.

As shown at 918, the piston displacement $\Delta y_{j,i}$ is modified with the calculated distance. In some examples, the piston is permitted to passively retract due to a pressure difference between pressure in the syringe barrel and atmosphere. In other examples, the piston can be (1) actively drawn back by the injector at a controlled rate, (2) drawn back by a controlled amount to more rapidly reduce the stored volume and energy, or (3) moved at specific positive increments such that flow rate does not exceed the programmed rate. Check valves in the system help to prevent any blood from being retracted into the fluid path upon piston retraction. Mixing of fluids that is not desired is also controlled with valves. Then, as shown at 920, a second injection phase of the injection is performed by advancing the second piston from the retracted position through at least a portion of the second syringe to expel fluid from the second syringe and into the conduit. In some examples, changes in pressure in the syringe(s) can continue to be monitored during the second phase of the injection. If an identified pressure change indicates that a flow rate spike may occur, the piston can be retracted or otherwise reduced in displacement rate, as described herein, to relieve pressure buildup.

Conditions may also evolve that require the piston displacement to be increased to meet the specified fluid flow rate. The relationships described herein all support such required responses.

Figure 49:
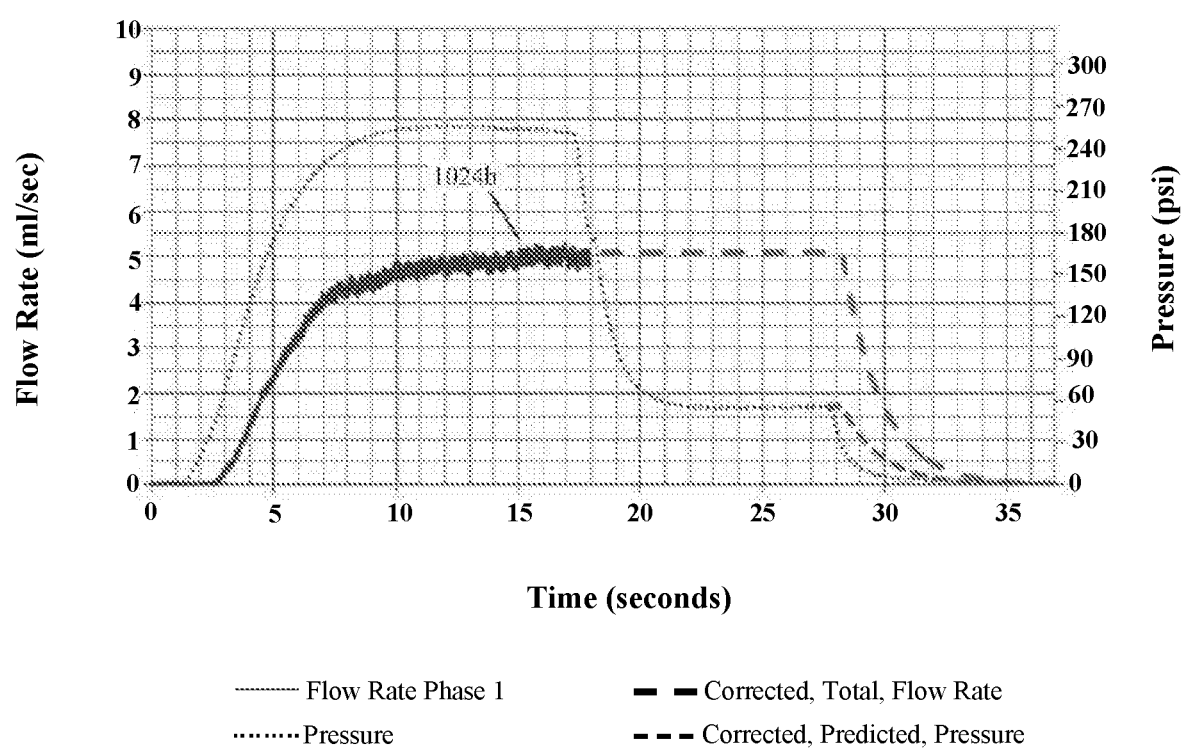
FIG. 49 is a graph illustrating flow rate with respect to time for a multiphase injection with motor control of the piston to avoid saline overrate according to an example of the disclosure.

The graph in FIG. 49 shows total flow rate 1024b and pressure for an injection performed both uncorrected and with motor control of the piston, as occurs in the method of FIG. 50. As shown in FIG. 49, total flow rate 1024b is generally constant at about $$5 \frac{ml}{second}.$$

The total flow rate 1024b does not include a flow rate spike at the transition between contrast and saline which is evident in FIG. 51.

Another parameter captured by the fluid-structure model presented here is total time for the injection. Controlling overrate of flow means that less fluid is injected over a given time. FIG. 49 illustrates both uncorrected and corrected pressure. Observe the increase for flow at steady state pressure and the longer time for pressure to reach the final steady state value of zero.

This method of reducing fluid overrate is preferred because it addresses fluid overrate while allowing a fluid injection to continue the saline flush at the programmed rate. Furthermore, the method shown in FIG. 50 does not require any knowledge or estimate of the impedance downstream of the syringe except to assume that there is little capacitive storing of energy downstream from the syringe. As such, more complex calculations based on geometry or material properties of the conduit, fluid path set, catheter, or syringes are not required. Note that downstream information is required unless an empirical relationship is available.

As discussed above, Equation 66 includes several values that may be temperature dependent. Since contrast is heated in some instances prior to being injected, variations in temperature can occur between delivered contrast and saline. For example, the constant value $K_{effective,j}$ which relates to the incremental capacitance of the fluid delivery system, may vary based on temperature or material degradation of the syringes and other system components. In a similar manner, syringe volume $V_{0,B,i}$ can vary based on temperature and pressure and be time dependent. While different syringe and tubing materials may react differently to temperature changes, material deformation and changes in material properties tend to become more pronounced as temperature and pressure increase. As such, in some examples, material deformation at increased pressure or temperature may need to be considered when calculating piston displacement.

Figure 53:
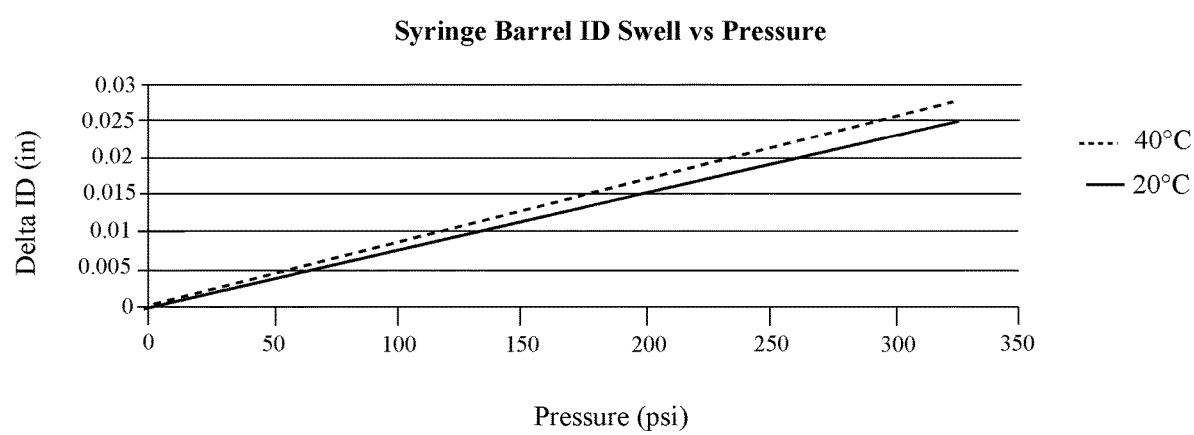
FIG. 53 is a graph illustrating syringe barrel diameter with respect to pressure during an injection at different temperatures.

A graph showing effects of temperature and pressure on a polycarbonate syringe is shown in FIG. 53. The graph illustrates an example relationship between syringe barrel swell and pressure in the syringe. Because the swell is small compared to the inner diameter (ID) of the syringe barrel, the increase in volume is proportional to delta ID and to the length of the syringe between the plunger and the syringe tip. Since the slope of delta ID vs. pressure is relatively linear; the capacitance may be modeled as a constant with pressure which is dependent upon plunger position. For this relationship between pressure and volume, capacitance may be used in the control of the syringe plungers discussed herein.

More specifically, the graph in FIG. 53 illustrates that the syringe barrel diameter increases as temperature and pressure increase. The swell of the syringe becomes more pronounced at higher pressures and temperatures as a result of the elastic modulus decreasing with temperature, a phenomena common to most materials. As a result, compliance and resulting capacitance of the syringe would also be expected to increase along with the increase in temperature and pressure. Material degradation with time and temperature can chronically reduce stiffness and strength over the entire temperature range. In view of such changes to syringe barrel diameter and compliance based on temperature and pressure, it may be beneficial to monitor the syringe or fluid delivery system and to update or recalculate constant values for the impedance module equation periodically to account for pressure and temperature changes or material degradation of the syringe or fluid path set. Relationships are determined before injection and are stored in readable media accessible to the injector. During injection, piston position and speed are updated to account for the change in volume stiffness or its inverse, compliance.

Other processes for reducing phase spikes or fluid overrate based on measured pressure can also be performed. For example, rather than retracting the piston by the calculated distance, it is possible to stop the piston motion until the pressure in the saline syringe stops decreasing or stabilizes as set forth above. Once the fluid pressure in the saline syringe stabilizes, movement of the piston to expel fluid from the syringe can continue.

In another example, the piston can be pushed back to a zero position or to a position corresponding to some minimal pressure, rather than attempting to calculate a retraction distance. Once the piston is retracted to the zero position or minimum pressure position, the piston can then be advanced to expel fluid from the syringe. This option has the benefit of absolutely minimizing the saline overrate event. However, retracting the piston to the zero position would likely cause a momentary dip in the saline flush delivery into the patient.

In other examples, a saline over-velocity or overrate could be reduced either through a reduced flow phase or by setting a saline pressure limit that is below the contrast pressure. Alternatively, a time when a transition (e.g., a transition between contrast and saline) will occur can be calculated, since a volume of the fluid path to the catheter is known. Accordingly, the saline flow or flush may be reduced or stopped just prior to the calculated time, so that any stored pressure produced by saline traveling through the fluid path set bleeds off more quickly. The amount of the halt, preferably in volume, can be estimated based on a pressure vs. volume of expansion curves or equations of the various fluid path elements. The volume of expansion curve for a fluid path set can be determined experimentally or derived mathematically from fluid path element geometries and material properties.

It would also be possible to take no action to compensate for system impedance, meaning that the piston would continue to move forward at a constant rate. However, this approach would produce the largest deviation from an ideal or programmed delivery. Accordingly, as shown in FIG. 51, fluid spike or fluid overrate would be expected to occur at a transition between contrast and saline phases of an injection.

Derivation of the Impedance Model Equation

An example of the impedance model, which may be computed and used by a fluid delivery system controller, is shown in Equations 1 through 65. In some examples, the model may be used in an iterative computer program to determine an actual volumetric flow rate $Q_{j,i}$ for fluid flowing out of syringe j at time i. As described in the model, fluid flow is the sum of two effects, namely motion of the piston $$\frac{\Delta y_{j,i}}{\Delta t}$$

and change in pressure of the syringe $(P_i - P_{i-\Delta t})$, which influences flow into or out of the capacitive component of the impedance of the syringe.

As will be appreciated by one of ordinary skill in the art, separate aspects of the models may model each of the syringes. Further, the overall impedance model may include multiple models of various subsystems or system aspects. The model may be operated in real time, optionally in an iterative way, such that as the pressure changes in the syringe and/or flow out of the syringes may be calculated. In some examples, calculated values may be used by a fluid delivery system controller to make the actual flow closer to the desired flow by moving the syringe plunger $\Delta y_{j,i}$ appropriately.

Derivation of the impedance model for Syringe A (containing a first fluid) and Syringe B (containing a second fluid) is shown in Equations 1 through 65. As shown in Equation 13, total volumetric flow rate ($Q_{TOTAL,i}$) is equal to the volumetric flow rate for Syringe A ($Q_{A,i}$) and Syringe B ($Q_{B,i}$).

At any time i, total flow rate $\dot{Q}_{TOTAL,i}$ is given by the Impedance Equation, Equation 67:

$$Q_{TOTAL,i} = A_{A,i} \frac{\Delta y_{j,i}}{\Delta t} + A_{B,i} \frac{\Delta y_{B,i}}{\Delta t} - \left\{ C_{A,i} + C_{B,i} + \frac{V_{A,i}}{\beta_{A,i}} + \frac{V_{B,i}}{\beta_{B,i}} \right\} \frac{(P_i - P_{i-\Delta t})}{\Delta t} = \frac{P_i}{R_{TOTAL,i}} = \tag{Equation 67}$$

$$\frac{P_{STEADY\ STATE,j} + (P_{i-\Delta t} - P_{STEADY\ STATE,j})e^{\frac{-\Delta t}{R_{TOTAL,i}C_{h,TOTAL,i}}}}{R_0 + R_1 \dot{Q}_{TOTAL,i-\Delta t}} =$$

-continued $$P_{STEADY\ STATE,j} + \frac{(P_{i-\Delta t} - P_{STEADY\ STATE,j})e^{\frac{-\Delta t}{R_{TOTAL,i}C_{h,TOTAL,i}}}}{\sum_{j=1}^{n}\frac{128\mu_{saline,j}L_j}{\pi\phi_j^4} + \dot{Q}_{TOTAL,i-\Delta t}\sum_{k=1}^{m}\frac{8\rho_{saline,k}}{\pi^2\phi_k^4(\text{Constant})^2}}$$

Equation 14 shows that total capacitance $C_{h,TOTAL,i} = C_{A,i} + C_{B,i}$ in Equation 67 is the sum of all of the capacitance in the system. Note the variations in Equation 67 that can be used depending on the sources of input data including hydraulic resistance, elastic response of the materials that create capacitance, pressure, and flow rate.

If pressure and flow rate are being calculated throughout the iterations of the injection, the algorithms using equations 1 to 65 must be utilized at each increment. Adjusting $\Delta y_{j,i}$ requires that iterations must continue until the sum of the iterations of $\Delta y_{j,i}$ equals the total length that corresponds to the injection volume for each syringe. Additional increments are required to allow fluid to flow from residual volume in capacitance after all pistons have stopped.

Note that as pressure decreases $P_i < P_{i-\Delta t}$, flow is out of capacitance, which is the mechanism for overrate. In some examples, the pressure value $P_i$ is determined based on real time data acquisition. For example, pressure sensors in the fluid delivery system can measure pressure of Syringe A, Syringe B, or a combined pressure for the system. In other examples, $P_i$ can be determined a priori based on volumetric flow rate and a friction model factor defined according to Equations 1 through 65 and equations using knowledge of steady state pressure and flow rates described previously. For example, Equations 17-23 illustrate calculations for changes in syringe diameter over time, changes to syringe cross sectional area with respect to time, changes in length of the syringe and fluid, and changes to fluid volume with respect to time as a function of pressure and piston position.

Equations 13 and 16 show that the sum of flow from all syringes is $Q_{TOTAL,i}$. The calculated value is compared to a set point or target value as described above in FIG. 50. Based on the results of the comparison, a necessary change of position or retraction ($\Delta y_{A,i}$ and/or $\Delta y_{B,i}$) of the pistons can be calculated and carried out. In some examples, a position of both pistons can be modified. In other examples, only a position of the saline piston is modified. Further, the calculations can be repeatedly carried out by the system and the position of the piston(s) adjusted or moved as needed to control flow rate in the system.

Computer pseudocode for implementing aspects of these calculations is shown in FIG. 54. In the pseudocode, control for the saline piston is related to the values for DELTAZB and ZADJUSTB, which are related to rotation of an injector motor (e.g., a motor that turns ball screw(s) of a drive assembly mechanism). As will be evident to one of ordinary skill in the art, communication to the motor controller current can be performed using syntax in the same program used for the fluid flow. For example, communication with the motor controller can be over one or more of analog, RS-232, RS-485, TCP and/or Ethernet connections. As shown in FIG. 54, the DO UNTIL loop does not execute unless the initial calculation for a respective increment predicts flow rate in excess of the predetermined limit (e.g., SyringeBFlow ratesetpoint).

While several examples of a fluid injection system are shown in the accompanying figures and described hereinabove in detail, other examples will be apparent to, and readily made by, those skilled in the art without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive. Although the disclosure has been described in detail for the purpose of illustration based on what is currently considered to be the most practical and preferred examples, it is to be understood that such detail is solely for that purpose and that the disclosure is not limited to the disclosed examples but, on the contrary, is intended to cover modifications and equivalent arrangements.

What is claimed is:

1. A method of improving fluid delivery performance of a fluid injection system, the method comprising:
   prior to initiating delivery of one or more fluids, modeling one or more factors that affects impedance of the fluid injection system based upon one or more known, estimated or measured parameters, wherein the modeling is based on an adjustable model for predicting future performance of the fluid injector system;
   initiating delivery of at least a first fluid of the one or more fluids to a patient at a first flow rate;
   measuring one or more characteristics of the fluid delivery;
   modeling one or more factors that affects impedance of the fluid injection system based upon one or more measurements of the one or more characteristics of the fluid delivery; and
   adjusting one or more characteristics of the fluid injection system based upon the one or more factors that affects impedance of the fluid injection system modeled on the one or more known, estimated or measured parameters or modeled on the one or more measurements of the one or more characteristics of the fluid delivery to improve fluid delivery performance.

2. The method of claim 1, further comprising initiating delivery of at least a second fluid to the patient at a second flow rate.

3. The method of claim 1, wherein an operator of the fluid injection system is notified of at least one adjustment made or suggested by the one or more factors that affects impedance of the fluid injection system modeled on the one or more known, estimated or measured parameters or modeled on the one or more measurements of the one or more characteristics of the fluid delivery.

4. The method of claim 1, further comprising adjusting the one or more characteristics of the fluid injection system based upon the one or more factors that affects impedance of the fluid injection system modeled on the one or more known, estimated or measured parameters prior to delivery of fluid to the patient.

5. A method of improving fluid delivery performance of a fluid injection system, the method comprising:
   prior to initiating delivery of one or more fluids, modeling one or more factors that affects impedance of the fluid injection system based upon one or more known, estimated or measured parameters, wherein the modeling is based on an adjustable model for predicting future performance of the fluid injector system;

initiating delivery of at least a first fluid of the one or more fluids to a patient at a first flow rate;

measuring one or more characteristics of the fluid delivery;

modeling one or more factors that affects impedance of the fluid injection system based upon one or more measurements of the one or more characteristics of the fluid delivery; and adjusting, during delivery of the first fluid, one or more characteristics of the fluid injection system based upon the one or more factors that affects impedance of the fluid injection system modeled on the one or more known, estimated or measured parameters or modeled on the one or more measurements of the one or more characteristics of the fluid delivery to improve fluid delivery performance.

6. The method of claim 5, further comprising initiating delivery of at least a second fluid to the patient at a second flow rate and adjusting the one or more characteristics of the fluid injection system based upon the one or more factors that affects impedance of the fluid injection system modeled on the one or more known, estimated or measured parameters or modeled on the one or more measurements of the one or more characteristics of the fluid delivery during delivery of one of the first or second fluid to improve fluid delivery performance.

7. The method of claim 1, wherein the one or more parameters is temperature, viscosity, pressure, bulk modulus, concentration, catheter size, hydraulic resistance, desired flow rate, and system capacitance.

8. The method of claim 1, wherein the one or more characteristics of the fluid delivery is temperature, viscosity, pressure, bulk modulus, hydraulic resistance, actual flow rate, and system capacitance.

9. The method of claim 6, wherein the adjustment of the one or more characteristics of the fluid injection system based upon the one or more factors that affects impedance of the fluid injection system modeled on the one or more known, estimated or measured parameters or modeled on the one or more measurements of the one or more characteristics of the fluid delivery occurs during delivery of both the first and second fluids.

10. A method of improving fluid delivery performance of a fluid injection system, the method comprising:

prior to initiating delivery of one or more fluids, modeling one or more factors that affects impedance of the fluid injection system based upon one or more known, estimated or measured parameters, wherein the modeling is based on an adjustable model for predicting future performance of the fluid injector system;

initiating delivery of at least a first fluid of the one or more fluids to a patient at a first flow rate;

measuring one or more characteristics of the fluid delivery;

modeling one or more factors that affects impedance of the fluid injection system based upon the one or more measurements of the one or more characteristics of the fluid delivery;

adjusting, during delivery of the first fluid, one or more characteristics of the fluid injection system based upon the one or more factors that affects impedance of the fluid injection system modeled on the one or more known, estimated or measured parameters or modeled on the one or more measurements of the one or more characteristics of the fluid delivery;

re-measuring one or more characteristics of the fluid delivery;

re-modeling one or more factors that affects impedance of the fluid injection system based upon one or more known, estimated or measured parameters or one or more re-measurements of the one or more characteristics of the fluid delivery; and re-adjusting, during delivery of the first fluid, the one or more characteristics of the fluid injection system based upon the one or more factors that affects impedance of the fluid injection system remodeled on the one or more known, estimated or measured parameters or re-modeled on the one or more re-measurements of the one or more characteristics of the fluid delivery to improve fluid delivery performance.

11. A method of improving fluid delivery performance of a fluid injection system, the method comprising:

prior to initiating delivery of one or more fluids, modeling one or more factors that affects impedance of the fluid injection system based upon one or more known, estimated or measured parameters, wherein the modeling is based on an adjustable model for predicting future performance of the fluid injector system;

initiating delivery of at least a first fluid of the one or more fluids to a patient at a first flow rate during a first phase of an injection with a first pressure limit;

measuring one or more characteristics of the fluid delivery;

modeling one or more factors that affects impedance of the fluid injection system based upon the one or more measurements of the one or more characteristics of the fluid delivery;

adjusting one or more characteristics of the fluid injection system based upon the one or more factors that affects impedance of the fluid injection system modeled on the one or more known, estimated or measured parameters or modeled on the one or more measurements of the one or more characteristics of the fluid delivery;

initiating delivery of at least a second fluid to the patient at a second flow rate and during a subsequent phase of an injection with a second pressure limit;

re-measuring one or more characteristics of the fluid delivery;

re-modeling one or more factors that affects impedance of the fluid injection system based upon one or more known, estimated or measured parameters or one or more re-measurements of the one or more characteristics of the fluid delivery; and re-adjusting, during delivery of the first fluid or the second fluid, the one or more characteristics of the fluid injection system based upon the one or more factors that affects impedance of the fluid injection system remodeled on the one or more known, estimated or measured parameters or re-modeled on the one or more re-measurements of the one or more characteristics of the fluid delivery to improve fluid delivery performance.

12. The method of claim 11, wherein the re-adjustment of the one or more characteristics of the fluid injection system based upon the one or more factors that affects impedance of the fluid injection system modeled on the one or more known, estimated or measured parameters or modeled on the one or more re-measurements of the one or more characteristics of the fluid delivery occurs during delivery of both the first and second fluids.

13. The method according to claim 12, further comprising deriving the second pressure limit from at least one of a table or an equation or pressure measured during the first phase.

14. The method according to claim 13, wherein the pressure limit is derived according to at least one or more of characteristics of the first fluid, characteristics of the second fluid, a catheter gauge, a predetermined desired flow rate, a position of a piston in a syringe of the fluid injector, and combinations thereof.

15. The method of claim 5, wherein an operator of the fluid injection system is notified of at least one adjustment made or suggested by the one or more factors that affects impedance of the fluid injection system modeled on the one or more known, estimated or measured parameters or modeled on the one or more measurements of the one or more characteristics of the fluid delivery.

16. The method of claim 5, further comprising adjusting, prior to delivery of fluid to the patient, the one or more characteristics of the fluid injection system based upon the one or more factors that affects impedance of the fluid injection system modeled on the one or more known, estimated or measured parameters.

17. The method of claim 5, wherein the one or more parameters is at least one of temperature, viscosity, pressure, bulk modulus, concentration, catheter size, hydraulic resistance, desired flow rate, and system capacitance.

18. The method of claim 5, wherein the one or more characteristics of the fluid delivery is at least one of temperature, viscosity, pressure, bulk modulus, hydraulic resistance, actual flow rate, and system capacitance.

* * * * *

UNITED STATES PATENT AND TRADEMARK OFFICE
CERTIFICATE OF CORRECTION

PATENT NO. : 11,141,535 B2
APPLICATION NO. : 16/621822
DATED : October 12, 2021
INVENTOR(S) : Uber, III et al.

Page 1 of 2

It is certified that error appears in the above-identified patent and that said Letters Patent is hereby corrected as shown below:

In the Specification
In Column 11, Line 49, delete "volume saline" and insert -- volume of saline --, therefor.
In Column 11, Line 56, delete "volume saline" and insert -- volume of saline --, therefor.
In Column 17, Line 59, delete "500/0-50%" and insert -- 50%-50% --, therefor.
In Column 24, Line 47, delete "C6" and insert -- $C_6$ --, therefor.
In Column 32, Line 12, delete "Pressure (psi) = 13.07 × $FR$ + 8.8" and insert -- *Pressure (psi)* = 13.07 × *FR* + 18.8 --, therefor.
In Column 32, Line 22, delete "40" and insert -- 40% --, therefor.
In Column 44, Line 62, delete "vicious fluid" and insert -- viscous fluid --, therefor.
In Column 46, Line 12, delete "until in" and insert -- until it --, therefor.
In Column 61, Line 7, delete "used to for" and insert -- used for --, therefor.
In Column 62, Line 19, delete "$V_{0j,i}=V_{0j,i-\Delta t}-A_{0j,i}\Delta y_{j,i}$" and insert -- $V_{0j,i} = V_{0j,i-\Delta t} - A_{0j,i}\Delta y_{j,i}$ --, therefor.
In Column 62, Line 31, delete "$V_{residual,j,i}$ [inches$^3$])" and insert -- $V_{residual,j,i}$ [inches$^3$] --, therefor.
In Column 63, Line 45, delete "$A_{j,i-\Delta t}\Delta \frac{y_{j,i}}{\Delta t}$" and insert -- $A_{j,i-\Delta t}\frac{\Delta y_{j,i}}{\Delta t}$ --, therefor.
In Column 63, Line 55, delete "$A_{j,i-\Delta t}\Delta y_{j,i}$" and insert -- $A_{j,i-\Delta t}\Delta y_{j,i}$ --, therefor.
In Column 65, Line 8, delete "$\Delta L_{P,j,i}[\text{inches}] = \frac{P_i L_{P,j,0}}{A_{j,i}E_{PL,i}}$" and insert -- $\Delta L_{Pj,i}[\text{inches}] = \frac{P_i L_{Pj,0}}{A_{j,i}E_{PL,i}}$ --, therefor.
In Column 65, Line 40, delete "Fluid $Length_{j,i} = L_{FILL,j}[\text{inches}] + \Delta L_{PJ,i} + \Delta L_{Sj,i} - \sum_{i=1}^{n}\Delta y_{j,i}$" and insert -- Fluid $Length_{j,i} = L_{FILL,j}[\text{inches}] + \Delta L_{Pj,i} + \Delta L_{Sj,i} - \sum_{i=1}^{n}\Delta y_{j,i}$ --, therefor.
In Column 69, Line 39, delete "the" and insert -- then --, therefor.

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,141,535 B2

In Column 69, Line 40, delete "$\int_{P_{i-\Delta r}}^{P_i} \frac{dP'}{(P'_i - P_{STEADY\ STATE,j})} = \frac{-1}{\tau_i} \int_{t=(i-\Delta t)}^{t=i} dt$" and insert -- $\int_{P_{i-\Delta t}}^{P_i} \frac{dP'}{(P'_i - P_{STEADY\ STATE,j})} = \frac{-1}{\tau_i} \int_{t=(i-\Delta t)}^{t=i} dt$ --, therefor.

In Column 69, Line 67, delete "$P_{STEADY\ STAT,jE}$" and insert -- $P_{STEADY\ STATE,j}$ --, therefor.

In Column 71, Line 47, delete "$\dot{Q}_{j,i} = \dot{Q}_{STEADY\ STATE,j} + (\dot{Q}_{j,i-\Delta t} - \dot{Q}_{STEADY\ STATE,j})e^{\frac{-\Delta t}{R_{TOTAL,i}C_{h,TOTAL,i}}}$" and insert -- $\dot{Q}_{j,i} = \dot{Q}_{STEADY\ STATE,j} + (\dot{Q}_{j,i-\Delta t} - \dot{Q}_{STEADY\ STATE,j})e^{\frac{-\Delta t}{R_{TOTAL,i}C_{h,TOTAL,i}}}$ --, therefor.

In Column 72, Line 2, delete "$\mu_{mix}$ and $\mu_{mix}$" and insert -- $\rho_{mix}$ and $\mu_{mix}$ --, therefor.

In Column 75, Line 30, delete "$\left(\frac{\Delta y_{j,i}}{\Delta t}\right)$" and insert -- $\left(\frac{\Delta y_{B,i}}{\Delta t}\right)$ --, therefor.

In Column 78, Lines 57-60, delete "$\dot{Q}_{TOTAL,i} = A_{A,i}\frac{\Delta y_{j,i}}{\Delta t} + A_{B,i}\frac{\Delta y_{B,i}}{\Delta t} - \left\{C_{A,i} + C_{B,i} + \frac{V_{A,i}}{\beta_{A,i}} + \frac{V_{B,i}}{\beta_{B,i}}\right\}\frac{(P_i - P_{i-\Delta t})}{\Delta t} = \frac{P_i}{R_{TOTAL,i}} = \frac{P_{STEADY\ STATE,j} + (P_{i-\Delta t} - P_{STEADY\ STATE,j})e^{\frac{-\Delta t}{R_{TOTAL,i}C_{h,TOTAL,i}}}}{R_0 + R_1\dot{Q}_{TOTAL,i-\Delta t}} =$" and insert -- $\dot{Q}_{TOTAL,i} = A_{A,i}\frac{\Delta y_{A,i}}{\Delta t} + A_{B,i}\frac{\Delta y_{B,i}}{\Delta t} - \left\{C_{A,i} + C_{B,i} + \frac{V_{A,i}}{\beta_{A,i}} + \frac{V_{B,i}}{\beta_{B,i}}\right\}\frac{(P_i - P_{i-\Delta t})}{\Delta t} = \frac{P_i}{R_{TOTAL,i}} =$ --, therefor.